US010844389B2

(12) United States Patent
Ainley et al.

(10) Patent No.: US 10,844,389 B2
(45) Date of Patent: *Nov. 24, 2020

(54) FAD2 PERFORMANCE LOCI AND CORRESPONDING TARGET SITE SPECIFIC BINDING PROTEINS CAPABLE OF INDUCING TARGETED BREAKS

(71) Applicants: Dow AgroSciences LLC, Indianapolis, IN (US); Sangamo Therapeutics, Inc., Richmond, CA (US)

(72) Inventors: W. Michael Ainley, Carmel, IN (US); Steven R. Webb, Westfield, IN (US); Jayakumar P. Samuel, Carmel, IN (US); Dmitry Y. Guschin, Gyeonggi-do (KR); Jeffrey C. Miller, Richmond, CA (US); Lei Zhang, Richmond, CA (US)

(73) Assignees: Dow AgroSciences LLC, Indianapolis, IN (US); Sangamo Therapeutics, Inc., Richmond, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/392,217

(22) Filed: Apr. 23, 2019

(65) Prior Publication Data
US 2019/0316141 A1    Oct. 17, 2019

Related U.S. Application Data

(60) Continuation of application No. 15/292,774, filed on Oct. 13, 2016, now Pat. No. 10,287,595, which is a
(Continued)

(51) Int. Cl.
*C12N 15/82* (2006.01)
*A01H 6/54* (2018.01)
(Continued)

(52) U.S. Cl.
CPC ..... *C12N 15/8216* (2013.01); *C12N 15/8247* (2013.01); *C12N 15/902* (2013.01); *A01H 5/10* (2013.01); *A01H 6/542* (2018.05)

(58) Field of Classification Search
None
See application file for complete search history.

(56) References Cited

U.S. PATENT DOCUMENTS

| 4,769,061 A | 9/1988 | Comai |
| 4,810,648 A | 3/1989 | Stalker |

(Continued)

FOREIGN PATENT DOCUMENTS

| EP | 0 242 246 | 11/1992 |
| GB | 2338237 | 8/1998 |

(Continued)

OTHER PUBLICATIONS

Ainley et al., "Trait Stacking via Targeted Genome Editing," *Plant Biotechnol. J.* 11(9):1126-1134 (2013).
(Continued)

*Primary Examiner* — Matthew R Keogh
(74) *Attorney, Agent, or Firm* — Dahna S. Pasternak; Pasternak Patent Law

(57) ABSTRACT

Methods and compositions for gene disruption, gene editing or gene stacking within a FAD2 loci by cleaving, in a site directed manner, a location in a FAD2 gene in a soybean cell, to generate a break in the FAD2 gene and then optionally integrating into the break a nucleic acid molecule of interest is disclosed.

13 Claims, 12 Drawing Sheets

Specification includes a Sequence Listing.

Related U.S. Application Data division of application No. 14/019,293, filed on Sep. 5, 2013, now Pat. No. 9,493,779.

(60) Provisional application No. 61/697,886, filed on Sep. 7, 2012.

(51) Int. Cl.
*A01H 5/10* (2018.01)
*C12N 15/90* (2006.01)

(56) References Cited

U.S. PATENT DOCUMENTS

| | | |
|---|---|---|
| 4,940,835 A | 7/1990 | Fraley et al. |
| 4,975,374 A | 12/1990 | DasSarma et al. |
| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas et al. |
| 6,200,759 B1 | 3/2001 | Dove et al. |
| 6,242,568 B1 | 6/2001 | Barbas et al. |
| 6,248,876 B1 | 6/2001 | Barry et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox et al. |
| 6,599,692 B1 | 6/2003 | Case et al. |
| 6,689,558 B2 | 2/2004 | Case |
| 6,794,136 B1 | 9/2004 | Eisenberg et al. |
| 6,903,185 B2 | 6/2005 | Kim et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,153,949 B2 | 12/2006 | Kim et al. |
| 7,253,273 B2 | 8/2007 | Collingwood |
| 7,262,054 B2 | 8/2007 | Jamieson et al. |
| 7,361,635 B2 | 4/2008 | Miller et al. |
| 8,420,782 B2 | 4/2013 | Bonas et al. |
| 8,440,431 B2 | 5/2013 | Voytas et al. |
| 9,493,779 B2 * | 11/2016 | Ainley ............... C12N 15/8247 |
| 2003/0232410 A1 | 12/2003 | Liljedahl et al. |
| 2005/0026157 A1 | 2/2005 | Baltimore et al. |
| 2005/0064474 A1 | 3/2005 | Holmes et al. |
| 2005/0208489 A1 | 9/2005 | Carroll et al. |
| 2005/0267061 A1 | 12/2005 | Martin |
| 2006/0188987 A1 | 8/2006 | Guschin et al. |
| 2006/0246440 A1 | 11/2006 | Joung et al. |
| 2007/0059795 A1 | 3/2007 | Moore et al. |
| 2007/0134796 A1 | 6/2007 | Holmes et al. |
| 2007/0218528 A1 | 9/2007 | Miller |
| 2008/0131962 A1 | 6/2008 | Miller |
| 2008/0182332 A1 | 7/2008 | Cai |
| 2009/0068164 A1 | 3/2009 | Barbas et al. |
| 2009/0117617 A1 | 5/2009 | Holmes et al. |
| 2009/0205083 A1 | 8/2009 | Gupta et al. |
| 2009/0263900 A1 | 10/2009 | DeKelver et al. |
| 2010/0047805 A1 | 2/2010 | Wang |
| 2010/0199389 A1 | 8/2010 | Butler et al. |
| 2011/0293785 A1 | 1/2011 | Franklin et al. |
| 2011/0041195 A1 | 2/2011 | Doyon |
| 2011/0123509 A1 | 5/2011 | Jantz et al. |
| 2011/0145940 A1 | 6/2011 | Voytas et al. |
| 2011/0167521 A1 | 7/2011 | DeKelver et al. |
| 2011/0189775 A1 | 8/2011 | Ainley et al. |
| 2011/0201055 A1 | 8/2011 | Doyon et al. |
| 2011/0207221 A1 | 8/2011 | Cost et al. |
| 2011/0239315 A1 | 9/2011 | Bonas et al. |
| 2011/0281361 A1 | 11/2011 | DeKelver et al. |
| 2011/0301073 A1 | 12/2011 | Gregory et al. |
| 2012/0102587 A1 | 4/2012 | Anai et al. |
| 2013/0326645 A1 | 12/2013 | Cost et al. |

FOREIGN PATENT DOCUMENTS

| | | |
|---|---|---|
| WO | WO 93/19181 | 9/1993 |
| WO | WO 95/19431 | 7/1995 |
| WO | WO 96/06166 | 7/1995 |
| WO | WO 96/30517 | 2/1996 |
| WO | WO 98/37186 | 2/1996 |
| WO | WO 98/53057 | 8/1998 |
| WO | WO 98/53058 | 11/1998 |
| WO | WO 98/53059 | 11/1998 |
| WO | WO 98/53060 | 11/1998 |
| WO | WO 98/54311 | 11/1998 |
| WO | WO 00/27878 | 12/1998 |
| WO | WO 01/60970 | 11/2001 |
| WO | WO 01/88197 | 11/2001 |
| WO | WO 02/016536 | 2/2002 |
| WO | WO 02/077227 | 10/2002 |
| WO | WO 02/099084 | 12/2002 |
| WO | WO 03/016496 | 2/2003 |
| WO | WO 03/080802 | 10/2003 |
| WO | WO 05/012515 | 2/2005 |
| WO | WO 05/028630 | 5/2005 |
| WO | WO 05/107437 | 11/2005 |
| WO | WO 07/014275 | 2/2007 |
| WO | WO 07/053482 | 5/2007 |
| WO | WO 10/079430 | 7/2010 |
| WO | WO 2011/005998 | 1/2011 |
| WO | WO 2011/049627 | 4/2011 |
| WO | WO 2011/146121 | 11/2011 |
| WO | WO 2014/039692 | 3/2014 |
| WO | WO 2014/141147 | 9/2014 |

OTHER PUBLICATIONS

Alt, et al., "Phenotypic and Molecular Analysts of Oleate Content in the Mutant Soybean Line M23," *Crop Science: A Journal Serving The International Community of Crop Scientists* 45(5):1997-2000 (2005).
ATCC Accession No. 39256 (printed on Dec. 5, 2014).
ATCC Accession No. 53435 (printed on Dec. 5, 2014).
ATCC Accession No. 67441 (printed on Dec. 5, 2014).
ATCC Accession No. 67442 (printed on Dec. 5, 2014).
Beerli et al., Toward Controlling Gene Expression at Will: Specific Regulation of the ERBB-2/HER-2 Promoter by Using Polydactyl Zinc Finger Proteins Constructed From Modular Building Blocks, *PNAS USA* 95(25):14628-14633 (1998).
Beerli et al., "Engineering Polydactyl Zinc-Finger Transcription Factors," *Nature Biotechnol.* 20:135-141(2002).
Bibikova et al., "Stimulation of Gomologous Recombination Through Targeted Cleavage by Chimeric Nucleases," *Mol. Cell. Biol.* 21(1):289-297 (2001).
Bibikova et al., "Enhancing Gene Targeting With Designed Zinc Finger Nucleases," *Science* 300(5620):764 (2003).
Bilinate et al., "FOKI Dimerization is Required for DNA Cleavage," *PNAS USA* 95:10570-10575 (1998).
Bones el al., "Genetic and Structural Characterization of the Avirulence Gene AVRBS3 From *Xanthomonas Campestris* pv. Vesicatori," *Mol. Gen. Genet.* 218:127-136 (1989).
Buhr, et al., "Ribozyme Termination of RNA Transcripts Down-Regulate Seed Fatty Acid Genes in Transgenic Soybean," *The Plant Journal* 30(2):155-163 (2002).
Cai et al., Targeted Transgene Integration in Plant Cells Using Designed Zinc Finger Nucleases, *Plant Mol. Biol.* 69(6):699-709 (2009).
Chi et al., "Genome-Wide Analysis of Fatty Acid Desaturases in Soybean (Glycine Max)," *Plant Mol. Biol. Rep.* 29:769-783 (2011).
Choo et al., Advances in Zinc Finger Engineering, *Curr, Opin. Struct. Biol.* 10:411-416 (2000).
Curtin et al., "Targeted Mutagenesis of Duplicated Genes in Soybean With Zinc-Fenger Nucleases," *Plant Physiology* 156:466-473 (2011).

(56) References Cited

OTHER PUBLICATIONS

D'Halluin et al., "Homologous Recomblnation: A Basis for Targeted Genome Optimization in Crop Species Such as Maize," *Plant Biotechnology Journal* 6(1):93-102 (2008).
DeGreef et al., "Evaluation of Herbicide Resistance in Transgenic Crops Under Field Conditions," *Bio/Technology* 7:61-64 (1989).
Devinder, et al., "Enhanced OLEIC Acid Content in the Soybean Mutant M23 is Associated With the Deletion in the FAD2-1A Gene Encoding a Fatty Acid Desaturase," *J. Amer. Oil Chem. Soc.* 84:229-235 (2007).
Dierkirkg, et al., "New Sources of Soybean Seed Meal and Oil Composition Traits Identified Through Tilling," *BMC Plant Biology* 9:89 (2009).
Elliott et al., "Isolation and Characterization of Fruit Vacuolar Invertase Genes From Two Tomato Species and Temporal Differences in MRNA Levels During Fruit Ripening" *Plant Molec. Biol.* 21:515-524 (1993).
Fisher et al., Starch Branching Enzyme II From Maize Endosperm , *Plant Physiol.* 102:1045-1046 (1993).
Geiser et al., "The Hypervariable Region in the Genes Coding for Entomopathogenic Crystal Proteins of *Bacillus thuringiensis*: Nucleotide Sequence of the Kurhdi Gene of Subsp. Kurstaki HD1," *Gene* 48:109 (1986).
Genbank AB188250, "Glycine-Max GMFAD2-1A Gene for Mocrosomal OMEGA-6 Fatty Acid Desaturase" (2011).
Haft et al., "A Guild of 45 CRISPR-Associated (CAS) Protein Families and Multiple CRISP/CAS Subtypes Exist in Prokaryotic Genomes," *PLoS Comput. Biol.* 1:e60 (2005) <http://www.jcvi.org/cms/nc/publications/listing/browse/3/article//Haft/#sthash.bXXP6pOi.dpuf>.
Hauschild, et al, "Efficient generation of a biallelic knockout in pigs using zinc-finger nucleases," *PNAS USA*, 108(29): 12013-12017 (2011).
Hayes et al., "Molecular Cloning and Heterologous Expression of a CDNA Encoding a Mouse Glutathione S-Transferase YC Subunit Possessing High Catalytic Activity for Aflatoxin B1-8,9-Epoxide," *Biochem. J.* 285:173-180 (1992).
Heppard, et al., "Developmental and Growth Temperature Regulation of Two Different Microsomal Omega-6 Desaturase Genes in Soybeans," *Plant Physiol.* 110:311-319 (1996).
Heuer et al., "Repeat Domain Diversity of AVRBS3-Like Genes in Ralstonia Solanacearum Strains and Association With Host Preferences in the Field," Appl. And Envir. Micro. 73(13):4379-4384 (2007).
Isalan et al., "A Rapid, Generally Applicable Method to Engineer Zinc Fingers Illustrated by Targeting the HIV-1 Promoter," *Nature Biotechnol.*19:656-660 (2001).
Jansen et al., "Identification of Genes That are Associated With DNA Repeats in Prokaryotes," *Mol. Microbiol.* 43:1565-1575 (2002).
Jones et al., "Isolation of the Tomato CF-9 Gene for Resistance to Cladosporiu Fulvum by Transposon Tagging," *Science* 266:789-793 (1994).
Kay et al., "A Bacterial Effector Acts as a Plant Transcription Factor and Induces a Cell Size Regulator," *Science* 318:648-651 (2007).
Kim et al., "Insertion and Deletion Mutants of FOKI Restriction Endonuclease," *Biol. Chem.* 269:31,978-41,982 (1994b).
Kim et al., "Chimeric Restrictin Endonuclease," *Proc. Natl. Acad. Sci. USA* 91:883-887 (1994a).
Kim el al., "Getting a Handhold on DNA: Design of Poly-Zinc Finger Proteins With Femtomolar Dissociation Constants," *PNAS USA* 95:2812-2817 (1998).
Knutson et al., "Modification of Brassica Seed Oil by Antisense Expression of a Stearoyl-Acyl Carrier Protein Desaturase Gene," *Proc. Natl. Acad. U.S.A.* 89:2624-2628 (1992).
Kumar et al., "Controlling Transgene Integration in Plants," *Trends Plant Sci.* 6:155-159(2001).
Le et al., "Simultaneous Generation and Germline Transmission of Multiple Gene Mutations in Rat Using CRISPR-CAS Systems," *Nature Biotechnology* 31:684-686 (2013).

Lee et al., "The Molecular Basis of Sulfonylurea Herbicide Resistance in Tobacco," *EMBO J.* 7(5):1241 (1988).
Li et al., "Alteration of Tile Cleavage Distance of FOK I Restriction Endonuclease by Insertion Mutagenesis," *Proc. Natl. Acad. Sci. USA* 90:2764-2768 (1993).
Li et al., "Functional Domains in FOK I Restriction Endonuclease," *Proc. Natl. Acad. Sci. USA* 89:4275-4279 (1992).
Liu et al., "Design of Polydactyl Zinc-Finger Proteins for Unique Addressing Within Complex Genomes," *PNAS USA* 94:5525-5530 (1997).
Makarova et al., "A Putative RNA-Interference-Based Immune System Inprokaryotes: Computational Analysis of the Predicted Enzymatic Machinery, Functional Analogies With Eukaryotic RNAI, and Hypothetical Mechanisms of Action," *Biol. Direct.* 1:7 (2006).
Makariva et al., "A DNA Repair System Specific for the Thermophilic Archaea and Bacteria Predicted by Genomic Context Analysis," *Nucleic Acids Res.* 30:482-496 (2002).
Mani et al., "Design, Engineering, and Characterilation of Zinc Finger Nucleases," *Biochem. Biophys. Res. Commun.* 334:1191-1197 (2005).
Marshall et al., Allelic Mutations in Acetyl-Coenzyme a Carbodxylase Confer Herbicide Tolerance in Maize, *Theor. Appl. Genet.* 83:435-442 (1992).
Martin et al., "MAP-Based Cloning of a Protein Kinase Gene Conferring Disease Resistance to Tomato," *Science* 262:1432-1436 (1993).
Miki et al., "Transformation of *Brassica napus* Canola Cultivars with *Arabodpsis Thaliana* Acetohydroxyacid Synthase Genes and Analysis of Herbicide Resistance," *Theor. Appl. Genet.* 80:449 (1990).
Mindrinos et al., "The *A. thaliana* Disease Resistance Gene RPS2 Encodes a Protein Containing a Nuclotide-Binding Site and Leucine-Rich Repeats," *Cell* 78:1089 (1994).
Moehle et al., "Targeted Gene Addition Into a Specified Location in the Human Genome Using Designed Zinc Finger Nucleases," *Proc. Natl. Acad. Sci. USA* 104(9):3055-3060 (2007).
Nekrasov et al., "Targeted Mutagenesis in the Model Plant Nicotiana Benthamiana Using CAS9 RNA-Guided Endonuclease," *Nature Biotechnology* 31:691-593 (2013).
Paho et aL, "Design and Selection of Novel CYS2HIS2 Zincfinger Proteins," *Ann. Rev. Biochem.* 70:313-340 (2001).
Paszkowaki et al., "Gene Targeting Inplaints," *EMBO J.* 7:4021-4026(1988).
Pen et al., "Production of Active Bacillus Licheniformis Alpha-Amylase in Tobacco and Its Application in Starch Liquefaction," *Bio/Technology* 10:292 (1992).
Pham, et al., "Mutant Alleles of FAD2-1A and FAD2-1BCombine to Produce Soybeans With the High OLEIC Acid Seed Oil Trait," *BMC Plant Biology* 10:195, p. 1-13 (2010).
Przibilla et al., "Site-Specific Mutagenesis of the D1 Subunit of Photosystem II in Wild-Type Chlamydomona," *Plant Cell* 3:169-174 (1991).
Puchta et al., "Homologous Recombination in Plant Cells is Enhanced by In Vivo Induction of Double Strand Breaks Into DNA by a Site-Specific Endonuclease," *Nucleic Acid Research* 21:5034-5040 (1993).
Raboy et al., "A Survey of Maize Kernel Mutants for Variation in Phytic Acid," *Maydica* 35:383-390 (1990).
Roberts et al., "Rebase: Restriction Enzymes and Methyltransferases," *Nucleic Acids Res.* 31:418-420 (2003).
Schierholt et al., "Inheritance of High OLEIC Acid Mutations in Winter Oilseed Rape (*Brassica napus* L.)" *Crop Sci.* 41:1444-1449 (2001).
Schomack et al., "Gene-For-Gene-Mediated Recognition of Nuclear-Targeted AVRBS3-Like Bacterial Effector Proteins," *J. Plant Physiol.* 163(3):256-272 (2006).
Segal, "Custom DNA-Binding Proteins Come of Age: Polydactyl Zinc-Finger Proteins," *Curr. Opin. Biotechnol.* 12:632-637 (2001).
Shan et al., "Targeted Genome Modification of Crop Plants Using a CRISPR-CAS System," *Nature Biotechnology* 31:686-680 (2013).
Shiroza et al., "Sequence Analysis of the Streptococcus Mutans Fructosyltransferase Gene and Flanking Regions," *J. Bacteriol.* 170(2):810-816 (1988).

(56) References Cited

OTHER PUBLICATIONS

Shukla et al., "Precise Genome Modification in Tile Crop Species *Zea mays* Using Zinc-Finger Nucleases," *Nature* 459:437-441 (2009).
Siebert and Puchta, "Efficient Repair of Genomic Double-Strand Breaks by Homologous Recombination Between Directly Repeated Sequences in the Plant Genome," *Plant Cell* 14:1121-1131 (2002).
Smith et al., "Requirements for Double-Strand Cleavage by Chimeric Restriction Enzymes With Zinc Finger DNA-Recognition Domains," *Nucleic Acids Res.* 28:3361-3369 (2000).
Sogaard et al., "Site-Directed Mutagenesis of Histidine 93, Aspartic Acid 180, Glutamic Acid 205, Histidine 290, and Aspartic Acid 291 at the Active Site and Tryptophan 279 at the Raw Starch Binding Site in Barley A-Amylase 1," *J. Biol. Chem.* 268:22480 (1993).
Steinmetz et al., "The DNA Sequence of the Gene for the Secreted *Bacillus subtilis* Enzyme Levansucrase and Its Genetic Control Sites," *Mol. Gen. Genet.* 20:220 (1985).
Tanhuanpaa et al., "Mapping and Cloning of EAD2 Gene to Develop Allele-Specific PCR for OLEIC Acid in Spring Turnip Rape (*Brassica rapa* ssp. Oleifera)," *Mol. Breed.* 4:543-550 (1998).
Terada et al., "Efficient Gene Targeting by Homologous Recombination in Rice," *Nat. Biotechnol.* 20(10):1030 (2002).
Terada et al., "Gene Targeting by Homologous Recombination as a Biotechnological Tool for Rice Functional Genomics," *Plant Physiol.* 144(2):846 (2007).
Urnov et al., "Genome Editing With Engineered Zinc Finger Nucleases," *Nature* 435(7042):646-651(2010).
Urnov et al., "Highly Efficient Endogenous Human Gene Correction Using Designed Zinc-Finger Nucleases," *Nature* 435:646-651 (2005).
Van Hartingsveldt et al., "Cloning, Characterization and Overexpression of the Phytase-Encoding Gene (PHYA) of *Aspergillus niger*," *Gene* 127:87-94 (1993).
Wah et al., "Structure of FOKI has Implications for DNA Cleavage," *PNAS USA* 95:10564-10569 (1998).
Wu et al., "Custom-Designed Zinc Finger Nucleases: What is Next?," *Cell. Mol. Life Sci.* 64:2933-2944.
Database Genbank Accession No. EU908062.1 https://www.ncbi.nlm.nih.gov/nuccore/EU908062.1/>Aug. 25, 2008.

* cited by examiner

Figure 1A: Alignment of the FAD2 2.3 sequences (41-1140 bp of coding sequence) from Williams 82 (SEQ ID NO:4), Westag (SEQ ID NO:5), X5(SEQ ID NO:6), Jack (SEQ ID NO:7), and Maverick (SEQ ID NO:8).

```
                            1                                                  50
2.3 Jack       (1)   GGAAGAAGCCTCTCTCAAGGGTTCCAAACACAAAGCCACCATTCACTGTT
2.3 Mav        (1)   GGAAGAAGCCTCTCTCAAGGGTTCCAAACACAAAGCCACCATTCACTGTT
2.3 W82        (1)   GGAAGAAGCCTCTCTCAAGGGTTCCAAACACAAAGCCACCATTCACTGTT
2.3 Wes        (1)   GGAAGAAGCCTCTCTCAAGGGTTCCAAACACAAAGCCACCATTCACTGTT
2.3 X5         (1)   GGAAGAAGCCTCTCTCAAGGGTTCCAAACACAAAGCCACCATTCACTGTT
                            51                                                100
2.3 Jack       (51)  GGCCAACTCAAGAAAGCAATTCCACCACACTGCTTTCAGCGCTCCCTCCT
2.3 Mav        (51)  GGCCAACTCAAGAAAGCAATTCCACCACACTGCTTTCAGCGCTCCCTCCT
2.3 W82        (51)  GGCCAACTCAAGAAAGCAATTCCACCACACTGCTTTCAGCGCTCCCTCCT
2.3 Wes        (51)  GGCCAACTCAAGAAAGCAATTCCACCACACTGCTTTCAGCGCTCCCTCCT
2.3 X5         (51)  GGCCAACTCAAGAAAGCAATTCCACCACACTGCTTTCAGCGCTCCCTCCT
                            101                                               150
2.3 Jack       (101) CACTTCATTCTCCTATGTTGTTTATGACCTTTCATTTGCCTTCATTTTCT
2.3 Mav        (101) CACTTCATTCTCCTATGTTGTTTATGACCTTTCATTTGCCTTCATTTTCT
2.3 W82        (101) CACTTCATTCTCCTATGTTGTTTATGACCTTTCATTTGCCTTCATTTTCT
2.3 Wes        (101) CACTTCATTCTCCTATGTTGTTTATGACCTTTCATTTGCCTTCATTTTCT
2.3 X5         (101) CACTTCATTCTCCTATGTTGTTTATGACCTTTCATTTGCCTTCATTTTCT
                            151                                               200
2.3 Jack       (151) ACATTGCCACCACCTACTTCCACCTCCTTCCTCAACCCTTTTCCCTCATT
2.3 Mav        (151) ACATTGCCACCACCTACTTCCACCTCCTTCCTCAACCCTTTTCCCTCATT
2.3 W82        (151) ACATTGCCACCACCTACTTCCACCTCCTTCCTCAACCCTTTTCCCTCATT
2.3 Wes        (151) ACATTGCCACCACCTACTTCCACCTCCTTCCTCAACCCTTTTCCCTCATT
2.3 X5         (151) ACATTGCCACCACCTACTTCCACCTCCTTCCTCAACCCTTTTCCCTCATT
                            201                                               250
2.3 Jack       (201) GCATGGCCAATCTATTGGGTTCTCCAAGGTTGCCTTCTCACTGGTGTGTG
2.3 Mav        (201) GCATGGCCAATCTATTGGGTTCTCCAAGGTTGCCTTCTCACTGGTGTGTG
2.3 W82        (201) GCATGGCCAATCTATTGGGTTCTCCAAGGTTGCCTTCTCACTGGTGTGTG
2.3 Wes        (201) GCATGGCCAATCTATTGGGTTCTCCAAGGTTGCCTTCTCACTGGTGTGTG
2.3 X5         (201) GCATGGCCAATCTATTGGGTTCTCCAAGGTTGCCTTCTCACTGGTGTGTG
                            251                                               300
2.3 Jack       (251) GGTGATTGCTCACGAGTGTGGTCACCATGCCTTCAGCAAGTACCAATGGG
2.3 Mav        (251) GGTGATTGCTCACGAGTGTGGTCACCATGCCTTCAGCAAGTACCAATGGG
2.3 W82        (251) GGTGATTGCTCACGAGTGTGGTCACCATGCCTTCAGCAAGTACCAATGGG
2.3 Wes        (251) GGTGATTGCTCACGAGTGTGGTCACCATGCCTTCAGCAAGTACCAATGGG
2.3 X5         (251) GGTGATTGCTCACGAGTGTGGTCACCATGCCTTCAGCAAGTACCAATGGG
                            301                                               350
2.3 Jack       (301) TTGATGATGTTGTGGGTTTGACCCTTCACTCAACACTTTTAGTCCCTTAT
2.3 Mav        (301) TTGATGATGTTGTGGGTTTGACCCTTCACTCAACACTTTTAGTCCCTTAT
2.3 W82        (301) TTGATGATGTTGTGGGTTTGACCCTTCACTCAACACTTTTAGTCCCTTAT
2.3 Wes        (301) TTGATGATGTTGTGGGTTTGACCCTTCACTCAACACTTTTAGTCCCTTAT
2.3 X5         (301) TTGATGATGTTGTGGGTTTGACCCTTCACTCAACACTTTTAGTCCCTTAT
                            351                                               400
2.3 Jack       (351) TTCTCATGGAAAATAAGCCATCGCCGCCATCACTCCAACACAGGTTCCCT
2.3 Mav        (351) TTCTCATGGAAAATAAGCCATCGCCGCCATCACTCCAACACAGGTTCCCT
2.3 W82        (351) TTCTCATGGAAAATAAGCCATCGCCGCCATCACTCCAACACAGGTTCCCT
2.3 Wes        (351) TTCTCATGGAAAATAAGCCATCGCCGCCATCACTCCAACACAGGTTCCCT
2.3 X5         (351) TTCTCATGGAAAATAAGCCATCGCCGCCATCACTCCAACACAGGTTCCCT
                            401                                               450
2.3 Jack       (401) TGACCGTGATGAAGTGTTTGTCCCAAAACCAAAATCCAAAGTTGCATGGT
2.3 Mav        (401) TGACCGTGATGAAGTGTTTGTCCCAAAACCAAAATCCAAAGTTGCATGGT
2.3 W82        (401) TGACCGTGATGAAGTGTTTGTCCCAAAACCAAAATCCAAAGTTGCATGGT
```

Figure 1B

```
2.3 Wes    (401) TGACCGTGATGAAGTGTTTGTCCCAAAACCAAAATCCAAAGTTGCATGGT
2.3 X5     (401) TGACCGTGATGAAGTGTTTGTCCCAAAACCAAAATCCAAAGTTGCATGGT
                 451                                              500
2.3 Jack   (451) TTTCCAAGTACTTAAACAACCCTCTAGGAAGGGCTGTTTCTCTTCTCGTC
2.3 Mav    (451) TTTCCAAGTACTTAAACAACCCTCTAGGAAGGGCTGTTTCTCTTCTCGTC
2.3 W82    (451) TTTCCAAGTACTTAAACAACCCTCTAGGAAGGGCTGTTTCTCTTCTCGTC
2.3 Wes    (451) TTTCCAAGTACTTAAACAACCCTCTAGGAAGGGCTGTTTCTCTTCTCGTC
2.3 X5     (451) TTTCCAAGTACTTAAACAACCCTCTAGGAAGGGCTGTTTCTCTTCTCGTC
                 501                                              550
2.3 Jack   (501) ACACTCACAATAGGGTGGCCTATGTATTTAGCCTTCAATGTCTCTGGTAG
2.3 Mav    (501) ACACTCACAATAGGGTGGCCTATGTATTTAGCCTTCAATGTCTCTGGTAG
2.3 W82    (501) ACACTCACAATAGGGTGGCCTATGTATTTAGCCTTCAATGTCTCTGGTAG
2.3 Wes    (501) ACACTCACAATAGGGTGGCCTATGTATTTAGCCTTCAATGTCTCTGGTAG
2.3 X5     (501) ACACTCACAATAGGGTGGCCTATGTATTTAGCCTTCAATGTCTCTGGTAG
                 551                                              600
2.3 Jack   (551) ACCCTATGATAGTTTTGCAAGCCACTACCACCCTTATGCTCCCATATATT
2.3 Mav    (551) ACCCTATGATAGTTTTGCAAGCCACTACCACCCTTATGCTCCCATATATT
2.3 W82    (551) ACCCTATGATAGTTTTGCAAGCCACTACCACCCTTATGCTCCCATATATT
2.3 Wes    (551) ACCCTATGATAGTTTTGCAAGCCACTACCACCCTTATGCTCCCATATATT
2.3 X5     (551) ACCCTATGATAGTTTTGCAAGCCACTACCACCCTTATGCTCCCATATATT
                 601                                              650
2.3 Jack   (601) CTAACCGTGAGAGGCTTCTGATCTATGTCTCTGATGTTGCTTTGTTTTCT
2.3 Mav    (601) CTAACCGTGAGAGGCTTCTGATCTATGTCTCTGATGTTGCTTTGTTTTCT
2.3 W82    (601) CTAACCGTGAGAGGCTTCTGATCTATGTCTCTGATGTTGCTTTGTTTTCT
2.3 Wes    (601) CTAACCGTGAGAGGCTTCTGATCTATGTCTCTGATGTTGCTTTGTTTTCT
2.3 X5     (601) CTAACCGTGAGAGGCTTCTGATCTATGTCTCTGATGTTGCTTTGTTTTCT
                 651                                              700
2.3 Jack   (651) GTGACTTACTCTCTCTACCGTGTTGCAACCCTGAAAGGGTTGGTTTGGCT
2.3 Mav    (651) GTGACTTACTCTCTCTACCGTGTTGCAACCCTGAAAGGGTTGGTTTGGCT
2.3 W82    (651) GTGACTTACTCTCTCTACCGTGTTGCAACCCTGAAAGGGTTGGTTTGGCT
2.3 Wes    (651) GTGACTTACTCTCTCTACCGTGTTGCAACCCTGAAAGGGTTGGTTTGGCT
2.3 X5     (651) GTGACTTACTCTCTCTACCGTGTTGCAACCCTGAAAGGGTTGGTTTGGCT
                 701                                              750
2.3 Jack   (701) GCTATGTGTTTATGGGGTGCCTTTGCTCATTGTGAACGGTTTTCTTGTGA
2.3 Mav    (701) GCTATGTGTTTATGGGGTGCCTTTGCTCATTGTGAACGGTTTTCTTGTGA
2.3 W82    (701) GCTATGTGTTTATGGGGTGCCTTTGCTCATTGTGAACGGTTTTCTTGTGA
2.3 Wes    (701) GCTATGTGTTTATGGGGTGCCTTTGCTCATTGTGAACGGTTTTCTTGTGA
2.3 X5     (701) GCTATGTGTTTATGGGGTGCCTTTGCTCATTGTGAACGGTTTTCTTGTGA
                 751                                              800
2.3 Jack   (751) CTATCACATATTTGCAGCACACACTTTGCCTTGCCTCATTACGATTCA
2.3 Mav    (751) CTATCACATATTTGCAGCACACACTTTGCCTTGCCTCATTACGATTCA
2.3 W82    (751) CTATCACATATTTGCAGCACACACTTTGCCTTGCCTCATTACGATTCA
2.3 Wes    (751) CTATCACATATTTGCAGCACACACTTTGCCTTGCCTCATTACGATTCA
2.3 X5     (751) CTATCACATATTTGCAGCACACACTTTGCCTTGCCTCATTACGATTCA
                 801                                              850
2.3 Jack   (801) TCAGAATGGGACTGGCTGAAGGGAGCTTTGGCAACTATGGACAGAGATTA
2.3 Mav    (801) TCAGAATGGGACTGGCTGAAGGGAGCTTTGGCAACTATGGACAGAGATTA
2.3 W82    (801) TCAGAATGGGACTGGCTGAAGGGAGCTTTGGCAACTATGGACAGAGATTA
2.3 Wes    (801) TCAGAATGGGACTGGCTGAAGGGAGCTTTGGCAACTATGGACAGAGATTA
2.3 X5     (801) TCAGAATGGGACTGGCTGAAGGGAGCTTTGGCAACTATGGACAGAGATTA
                 851                                              900
2.3 Jack   (851) TGGGATTCTGAACAAGGTGTTTCATCACATAACTGATACTCATGTGGCTC
2.3 Mav    (851) TGGGATTCTGAACAAGGTGTTTCATCACATAACTGATACTCATGTGGCTC
2.3 W82    (851) TGGGATTCTGAACAAGGTGTTTCATCACATAACTGATACTCATGTGGCTC
```

Figure 1C

```
  2.3 Wes   (851)  TGGGATTCTGAACAAGGTGTTTCATCACATAACTGATACTCATGTGGCTC
  2.3 X5    (851)  TGGGATTCTGAACAAGGTGTTTCATCACATAACTGATACTCATGTGGCTC
                   901                                              950
  2.3 Jack  (901)  ACCATCTCTTCTCTACAATGCCACATTACCATGCAATGGAGGCAACCAAT
  2.3 Mav   (901)  ACCATCTCTTCTCTACAATGCCACATTACCATGCAATGGAGGCAACCAAT
  2.3 W82   (901)  ACCATCTCTTCTCTACAATGCCACATTACCATGCAATGGAGGCAACCAAT
  2.3 Wes   (901)  ACCATCTCTTCTCTACAATGCCACATTACCATGCAATGGAGGCAACCAAT
  2.3 X5    (901)  ACCATCTCTTCTCTACAATGCCACATTACCATGCAATGGAGGCAACCAAT
                   951                                             1000
  2.3 Jack  (951)  GCAATCAAGCCAATATTGGGTGAGTACTACCAATTTGATGACACACCATT
  2.3 Mav   (951)  GCAATCAAGCCAATATTGGGTGAGTACTACCAATTTGATGACACACCATT
  2.3 W82   (951)  GCAATCAAGCCAATATTGGGTGAGTACTACCAATTTGATGACACACCATT
  2.3 Wes   (951)  GCAATCAAGCCAATATTGGGTGAGTACTACCAATTTGATGACACACCATT
  2.3 X5    (951)  GCAATCAAGCCAATATTGGGTGAGTACTACCAATTTGATGACACACCATT
                   1001                                            1050
  2.3 Jack (1001)  TTACAAGGCACTGTGGAGAGAAGCGAGAGAGTGCCTCTATGTGGAGCCAG
  2.3 Mav  (1001)  TTACAAGGCACTGTGGAGAGAAGCGAGAGAGTGCCTCTATGTGGAGCCAG
  2.3 W82  (1001)  TTACAAGGCACTGTGGAGAGAAGCGAGAGAGTGCCTCTATGTGGAGCCAG
  2.3 Wes  (1001)  TTACAAGGCACTGTGGAGAGAAGCGAGAGAGTGCCTCTATGTGGAGCCAG
  2.3 X5   (1001)  TTACAAGGCACTGTGGAGAGAAGCGAGAGAGTGCCTCTATGTGGAGCCAG
                   1051                                            1100
  2.3 Jack (1051)  ATGAAGGAACATCCGAGAAGGGCGTGTATTGGTACAGGAACAAGTATTGA
  2.3 Mav  (1051)  ATGAAGGAACATCCGAGAAGGGCGTGTATTGGTACAGGAACAAGTATTGA
  2.3 W82  (1051)  ATGAAGGAACATCCGAGAAGGGCGTGTATTGGTACAGGAACAAGTATTGA
  2.3 Wes  (1051)  ATGAAGGAACATCCGAGAAGGGCGTGTATTGGTACAGGAACAAGTATTGA
  2.3 X5   (1051)  ATGAAGGAACATCCGAGAAGGGCGTGTATTGGTACAGGAACAAGTATTGA
```

Figure 2A: Alignment of the FAD2 2.6 sequences (40-1140 bp of coding sequence) from Williams 82 (SEQ ID NO:9), Westag (SEQ ID NO:10), X5(SEQ ID NO:11), Jack (SEQ ID NO:12), and Maverick (SEQ ID NO:13).

```
                       1                                                  50
2.6 Jack     (1)       CAGAAGAAGCCTCTCTCAAGGGTTCCAAACACAAAGCCACCATTCACTGT
2.6 Mav      (1)       CAGAAGAAGCCTCTCTCAAGGGTTCCAAACACAAAGCCACCATTCACTGT
2.6 W82      (1)       CAGAAGAAGCCTCTCTCAAGGGTTCCAAACACAAAGCCACCATTCACTGT
2.6 Wes      (1)       CAGAAGAAGCCTCTCTCAAGGGTTCCAAACACAAAGCCACCATTCACTGT
2.6 X5       (1)       CAGAAGAAGCCTCTCTCAAGGGTTCCAAACACAAAGCCACCATTCACTGT
                       51                                                 100
2.6 Jack     (51)      TGGCCAACTCAAGAAAGCCATTCCACCGCACTGCTTTCAGCGTTCCCTCC
2.6 Mav      (51)      TGGCCAACTCAAGAAAGCCATTCCACCGCACTGCTTTCAGCGTTCCCTCC
2.6 W82      (51)      TGGCCAACTCAAGAAAGCCATTCCACCGCACTGCTTTCAGCGTTCCCTCC
2.6 Wes      (51)      TGGCCAACTCAAGAAAGCCATTCCACCGCACTGCTTTCAGCGTTCCCTCC
2.6 X5       (51)      TGGCCAACTCAAGAAAGCCATTCCACCGCACTGCTTTCAGCGTTCCCTCC
                       101                                                150
2.6 Jack     (101)     TCACTTCATTGTCCTATGTTGTTATGACCTTTCATTGGCTTTCATTTTC
2.6 Mav      (101)     TCACTTCATTGTCCTATGTTGTTATGACCTTTCATTGGCTTTCATTTTC
2.6 W82      (101)     TCACTTCATTGTCCTATGTTGTTATGACCTTTCATTGGCTTTCATTTTC
2.6 Wes      (101)     TCACTTCATTGTCCTATGTTGTTATGACCTTTCATTGGCTTTCATTTTC
2.6 X5       (101)     TCACTTCATTGTCCTATGTTGTTATGACCTTTCATTGGCTTTCATTTTC
                       151                                                200
2.6 Jack     (151)     TACATTGCCACCACCTACTTCCACCTCCTCCCTCACCCCTTTTCCTCAT
2.6 Mav      (151)     TACATTGCCACCACCTACTTCCACCTCCTCCCTCACCCCTTTTCCTCAT
2.6 W82      (151)     TACATTGCCACCACCTACTTCCACCTCCTCCCTCACCCCTTTTCCTCAT
2.6 Wes      (151)     TACATTGCCACCACCTACTTCCACCTCCTCCCTCACCCCTTTTCCTCAT
2.6 X5       (151)     TACATTGCCACCACCTACTTCCACCTCCTCCCTCACCCCTTTTTCCTCAT
                       201                                                250
2.6 Jack     (201)     TGCATGGCCAATCTATTGGGTTCTCCAAGGTTGCATTCTTACTGGCGTGT
2.6 Mav      (201)     TGCATGGCCAATCTATTGGGTTCTCCAAGGTTGCATTCTTACTGGCGTGT
2.6 W82      (201)     TGCATGGCCAATCTATTGGGTTCTCCAAGGTTGCATTCTTACTGGCGTGT
2.6 Wes      (201)     TGCATGGCCAATCTATTGGGTTCTCCAAGGTTGCATTCTTACTGGCGTGT
2.6 X5       (201)     TGCATGGCCAATCTATTGGGTTCTCCAAGGTTGCATTCTTACTGGCGTGT
                       251                                                300
2.6 Jack     (251)     GGGTGATTGCTCACGAGTGTGGTCACCATGCCTTCAGCAAGTACCCATGG
2.6 Mav      (251)     GGGTGATTGCTCACGAGTGTGGTCACCATGCCTTCAGCAAGTACCCATGG
2.6 W82      (251)     GGGTGATTGCTCACGAGTGTGGTCACCATGCCTTCAGCAAGTACCCATGG
2.6 Wes      (251)     GGGTGATTGCTCACGAGTGTGGTCACCATGCCTTCAGCAAGTACCCATGG
2.6 X5       (251)     GGGTGATTGCTCACGAGTGTGGTCACCATGCCTTCAGCAAGTACCCATGG
                       301                                                350
2.6 Jack     (301)     GTTGATGATGTTGTGGGTTTGACCGTTCACTCAGCACTTTTAGTCCCTTA
2.6 Mav      (301)     GTTGATGATGTTGTGGGTTTGACCGTTCACTCAGCACTTTTAGTCCCTTA
2.6 W82      (301)     GTTGATGATGTTGTGGGTTTGACCGTTCACTCAGCACTTTTAGTCCCTTA
2.6 Wes      (301)     GTTGATGATGTTGTGGGTTTGACCGTTCACTCAGCACTTTTAGTCCCTTA
2.6 X5       (301)     GTTGATGATGTTGTGGGTTTGACCGTTCACTCAGCACTTTTAGTCCCTTA
                       351                                                400
2.6 Jack     (351)     TTTCTCATGGAAAATAAGCCATCGCCGCCACCACTCCAACACGGGTTCCC
2.6 Mav      (351)     TTTCTCATGGAAAATAAGCCATCGCCGCCACCACTCCAACACGGGTTCCC
2.6 W82      (351)     TTTCTCATGGAAAATAAGCCATCGCCGCCACCACTCCAACACGGGTTCCC
2.6 Wes      (351)     TTTCTCATGGAAAATAAGCCATCGCCGCCACCACTCCAACACGGGTTCCC
2.6 X5       (351)     TTTCTCATGGAAAATAAGCCATCGCCGCCACCACTCCAACACGGGTTCCC
                       401                                                450
2.6 Jack     (401)     TTGACCGTGATGAAGTGTTTGTCCCAAAACCAAAATCCAAAGTTGCATGG
2.6 Mav      (401)     TTGACCGTGATGAAGTGTTTGTCCCAAAACCAAAATCCAAAGTTGCATGG
2.6 W82      (401)     TTGACCGTGATGAAGTGTTTGTCCCAAAACCAAAATCCAAAGTTGCATGG
```

Figure 2B

```
2.6 Wes    (401) TTGACCGTGATGAAGTGTTTGTCCCAAAAACCAAAAATCCAAAGTTGCATGG
2.6 X5     (401) TTGACCGTGATGAAGTGTTTGTCCCAAAAACCAAAAATCCAAAGTTGCATGG
                 451                                               500
2.6 Jack   (451) TACACCAAGTACCTGAACAACCCTCTAGGAAGGGCTGCTTCTCTTCTCAT
2.6 Mav    (451) TACACCAAGTACCTGAACAACCCTCTAGGAAGGGCTGCTTCTCTTCTCAT
2.6 W82    (451) TACACCAAGTACCTGAACAACCCTCTAGGAAGGGCTGCTTCTCTTCTCAT
2.6 Wes    (451) TACACCAAGTACCTGAACAACCCTCTAGGAAGGGCTGCTTCTCTTCTCAT
2.6 X5     (451) TACACCAAGTACCTGAACAACCCTCTAGGAAGGGCTGCTTCTCTTCTCAT
                 501                                               550
2.6 Jack   (501) CACACTCACAATAGGGTGGCCTTTGTATTTAGCCTTCAATGTCTCTGGCA
2.6 Mav    (501) CACACTCACAATAGGGTGGCCTTTGTATTTAGCCTTCAATGTCTCTGGCA
2.6 W82    (501) CACACTCACAATAGGGTGGCCTTTGTATTTAGCCTTCAATGTCTCTGGCA
2.6 Wes    (501) CACACTCACAATAGGGTGGCCTTTGTATTTAGCCTTCAATGTCTCTGGCA
2.6 X5     (501) CACACTCACAATAGGGTGGCCTTTGTATTTAGCCTTCAATGTCTCTGGCA
                 551                                               600
2.6 Jack   (551) GACCCTATGATGGTTTTGCTAGCCACTACCACCCTTATGCTCCAATATAT
2.6 Mav    (551) GACCCTATGATGGTTTTGCTAGCCACTACCACCCTTATGCTCCAATATAT
2.6 W82    (551) GACCCTATGATGGTTTTGCTAGCCACTACCACCCTTATGCTCCAATATAT
2.6 Wes    (551) GACCCTATGATGGTTTTGCTAGCCACTACCACCCTTATGCTCCAATATAT
2.6 X5     (551) GACCCTATGATGGTTTTGCTAGCCACTACCACCCTTATGCTCCTATATAT
                 601                                               650
2.6 Jack   (601) TCAAAACGTGAGAGGCTTCTGATCTATGTCTCTGATGTTGCTTTGTTTTC
2.6 Mav    (601) TCAAAACGTGAGAGGCTTCTGATCTATGTCTCTGATGTTGCTTTGTTTTC
2.6 W82    (601) TCAAAACGTGAGAGGCTTCTGATCTATGTCTCTGATGTTGCTTTGTTTTC
2.6 Wes    (601) TCAAAACGTGAGAGGCTTCTGATCTATGTCTCTGATGTTGCTTTGTTTTC
2.6 X5     (601) TCAAACCGTGAGAGGCTTCTGATCTATGTCTCTGATGTTGCTTTGTTTTC
                 651                                               700
2.6 Jack   (651) TGTGACTTACTTGCTCTACCGTGTTGCAACTATGAAAGGGTTGGTTTGGC
2.6 Mav    (651) TGTGACTTACTTGCTCTACCGTGTTGCAACTATGAAAGGGTTGGTTTGGC
2.6 W82    (651) TGTGACTTACTTGCTCTACCGTGTTGCAACTATGAAAGGGTTGGTTTGGC
2.6 Wes    (651) TGTGACTTACTTGCTCTACCGTGTTGCAACTATGAAAGGGTTGGTTTGGC
2.6 X5     (651) TGTGACTTACTTGCTCTACCGTGTTGCAACTATGAAAGGGTTGGTTTGGC
                 701                                               750
2.6 Jack   (701) TGCTATGTGTTTATGGGGTGCCATTGCTCATTGTGAACGGTTTTCTTGTG
2.6 Mav    (701) TGCTATGTGTTTATGGGGTGCCATTGCTCATTGTGAACGGTTTTCTTGTG
2.6 W82    (701) TGCTATGTGTTTATGGGGTGCCATTGCTCATTGTGAACGGTTTTCTTGTG
2.6 Wes    (701) TGCTATGTGTTTATGGGGTGCCATTGCTCATTGTGAACGGTTTTCTTGTG
2.6 X5     (701) TGCTATGTGTTTATGGGGTGCCATTGCTCATTGTGAACGGTTTTCTTGTG
                 751                                               800
2.6 Jack   (751) ACCATCACATATCTGCAGCACACACACTATGCCTTGCCTCACTATGATTC
2.6 Mav    (751) ACCATCACATATCTGCAGCACACACACTATGCCTTGCCTCACTATGATTC
2.6 W82    (751) ACCATCACATATCTGCAGCACACACACTATGCCTTGCCTCACTATGATTC
2.6 Wes    (751) ACCATCACATATCTGCAGCACACACACTATGCCTTGCCTCACTATGATTC
2.6 X5     (751) ACCATCACATATCTGCAGCACACACACTATGCCTTGCCTCACTATGATTC
                 801                                               850
2.6 Jack   (801) ATCAGAATGGGATTGGCTGAGGGGTGCTTTGGCAACTATGGACAGAGATT
2.6 Mav    (801) ATCAGAATGGGATTGGCTGAGGGGTGCTTTGGCAACTATGGACAGAGATT
2.6 W82    (801) ATCAGAATGGGATTGGCTGAGGGGTGCTTTGGCAACTATGGACAGAGATT
2.6 Wes    (801) ATCAGAATGGGATTGGCTGAGGGGTGCTTTGGCAACTATGGACAGAGATT
2.6 X5     (801) ATCAGAATGGGATTGGCTGAGGGGTGCTTTGGCAACTATGGACAGAGATT
                 851                                               900
2.6 Jack   (851) ATGGGATTCTGAACAAGGTGTTTCACCACATAACTGATACTCATGTGGCT
2.6 Mav    (851) ATGGGATTCTGAACAAGGTGTTTCACCACATAACTGATACTCATGTGGCT
2.6 W82    (851) ATGGGATTCTGAACAAGGTGTTTCACCACATAACTGATACTCATGTGGCT
```

Figure 2C

```
2.6 Wes   (851) ATGGGATTCTGAACAAGGTGTTTCACCACATAACTGATACTCATGTGGCT
2.6 X5    (851) ATGGGATTCTGAACAAGGTGTTTCACCACATAACTGATACTCATGTGGCT
                901                                              950
2.6 Jack  (901) CACCATCTTTTCTCTACAATGCCACATTACCATGCAACGGAGGCAACCAA
2.6 Mav   (901) CACCATCTTTTCTCTACAATGCCACATTACCATGCAACGGAGGCAACCAA
2.6 W82   (901) CACCATCTTTTCTCTACAATGCCACATTACCATGCAACGGAGGCAACCAA
2.6 Wes   (901) CACCATCTTTTCTCTACAATGCCACATTACCATGCAACGGAGGCAACCAA
2.6 X5    (901) CACCATCTTTTCTCTACAATGCCACATTACCATGCAACGGAGGCAACCAA
                951                                             1000
2.6 Jack  (951) TGCAATGAAGCCAATATTGGGTGAGTACTACCGATTTGATGACACACCAT
2.6 Mav   (951) TGCAATGAAGCCAATATTGGGTGAGTACTACCGATTTGATGACACACCAT
2.6 W82   (951) TGCAATGAAGCCAATATTGGGTGAGTACTACCGATTTGATGACACACCAT
2.6 Wes   (951) TGCAATGAAGCCAATATTGGGTGAGTACTACCGATTTGATGACACACCAT
2.6 X5    (951) TGCAATGAAGCCAATATTGGGTGAGTACTACCGATTTGATGACACACCAT
                1001                                            1050
2.6 Jack (1001) TTTACAAGGCACTGTGGAGAGAAGCAAGAGAGTGCCTCTATGTGGAGCCA
2.6 Mav  (1001) TTTACAAGGCACTGTGGAGAGAAGCAAGAGAGTGCCTCTATGTGGAGCCA
2.6 W82  (1001) TTTACAAGGCACTGTGGAGAGAAGCAAGAGAGTGCCTCTATGTGGAGCCA
2.6 Wes  (1001) TTTACAAGGCACTGTGGAGAGAAGCAAGAGAGTGCCTCTATGTGGAGCCA
2.6 X5   (1001) TTTACAAGGCACTGTGGAGAGAAGCAAGAGAGTGCCTCTATGTGGAGCCA
                1051                                            1100
2.6 Jack (1051) GATGAAGGAACATCCGAGAAGGGCGTGTATTGGTACAGGAACAAGTATTG
2.6 Mav  (1051) GATGAAGGAACATCCGAGAAGGGCGTGTATTGGTACAGGAACAAGTATTG
2.6 W82  (1051) GATGAAGGAACATCCGAGAAGGGCGTGTATTGGTACAGGAACAAGTATTG
2.6 Wes  (1051) GATGAAGGAACATCCGAGAAGGGCGTGTATTGGTACAGGAACAAGTATTG
2.6 X5   (1051) GATGAAGGAACATCCGAGAAGGGCGTGTATTGGTACAGGAACAAGTATTG
                1101
2.6 Jack (1101) A
2.6 Mav  (1101) A
2.6 W82  (1101) A
2.6 Wes  (1101) A
2.6 X5   (1101) A
```

Figure 3: Activity of FAD2 2.3 and 2.6 gene designed ZFNs in a DLSSA assay. ZFNs designed to the FAD2 2.3 and 2.6 loci were evaluated for cleavage activity of FAD2 2.3 and 2.6 sequences that were cloned into mammalian cells as reporters.
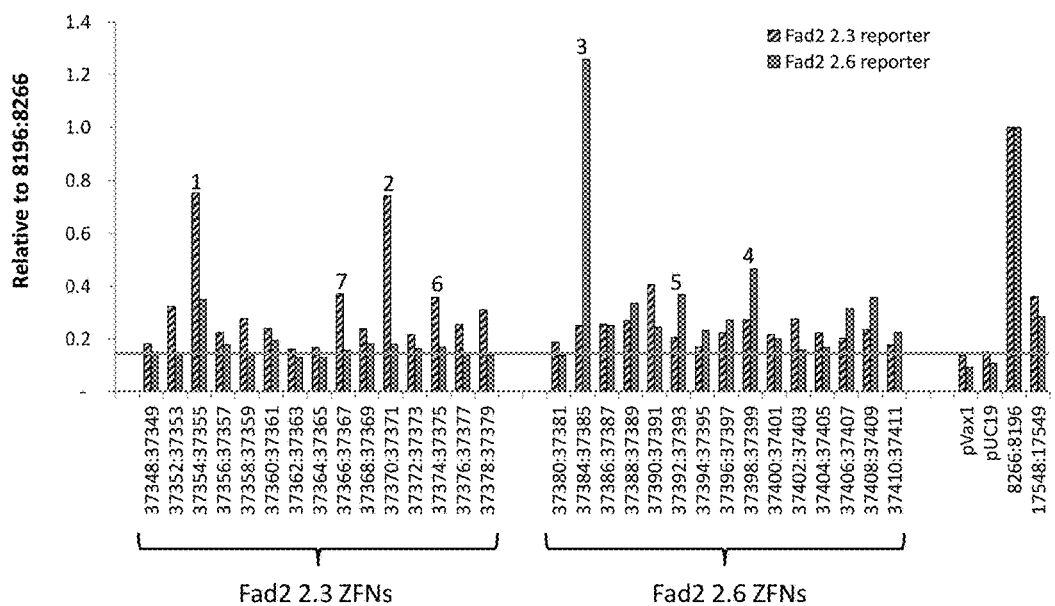

Figure 4: Plasmid map of pDAB115620.
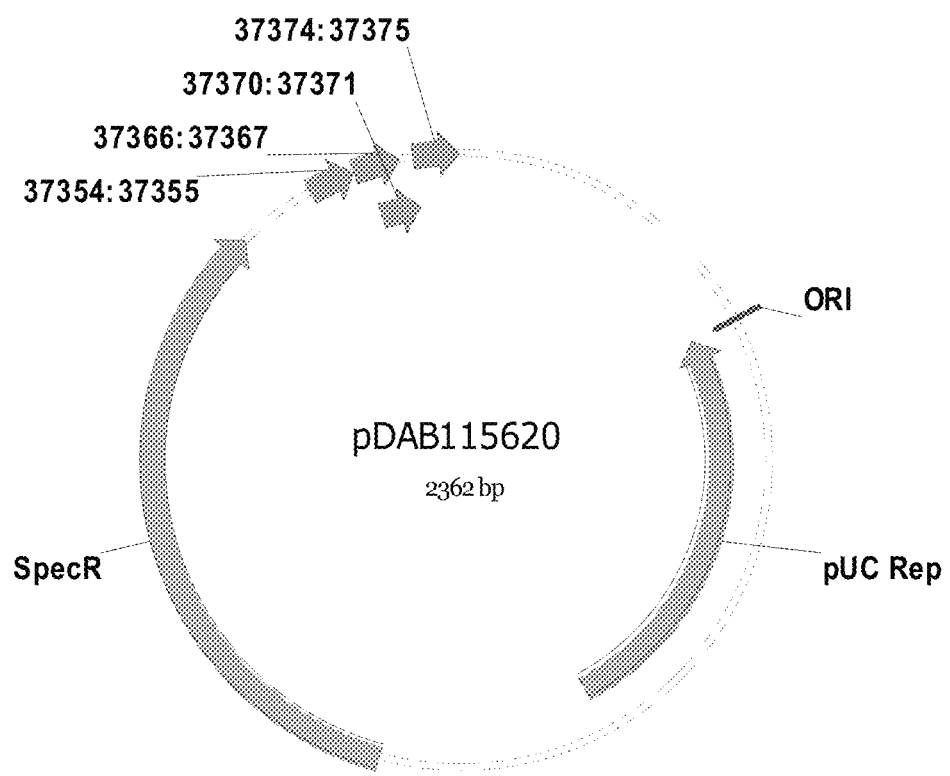

Figure 5: Plasmid map of pDAB115622
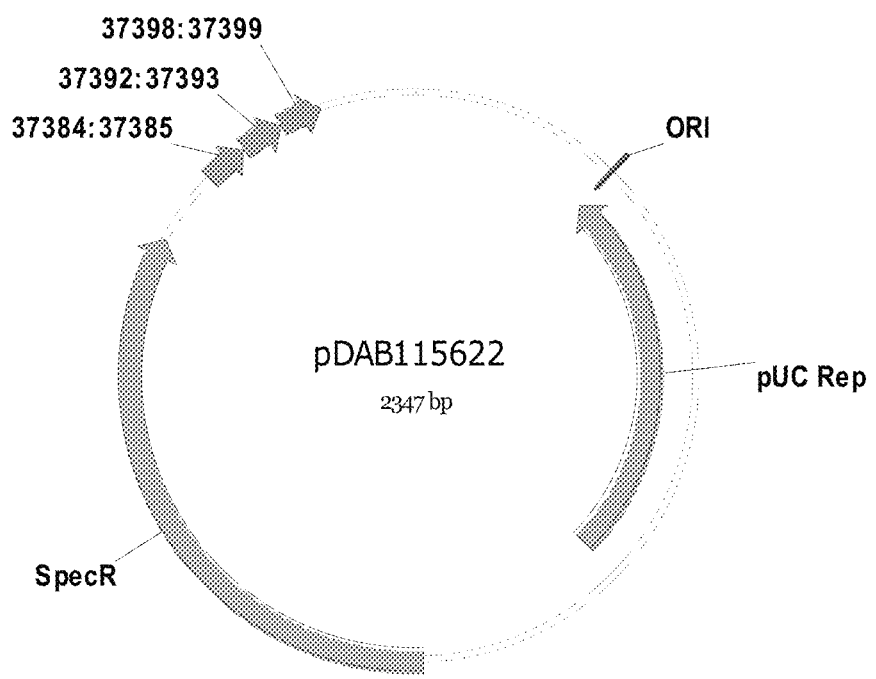

Figure 6: Plasmid map of pDAB7221
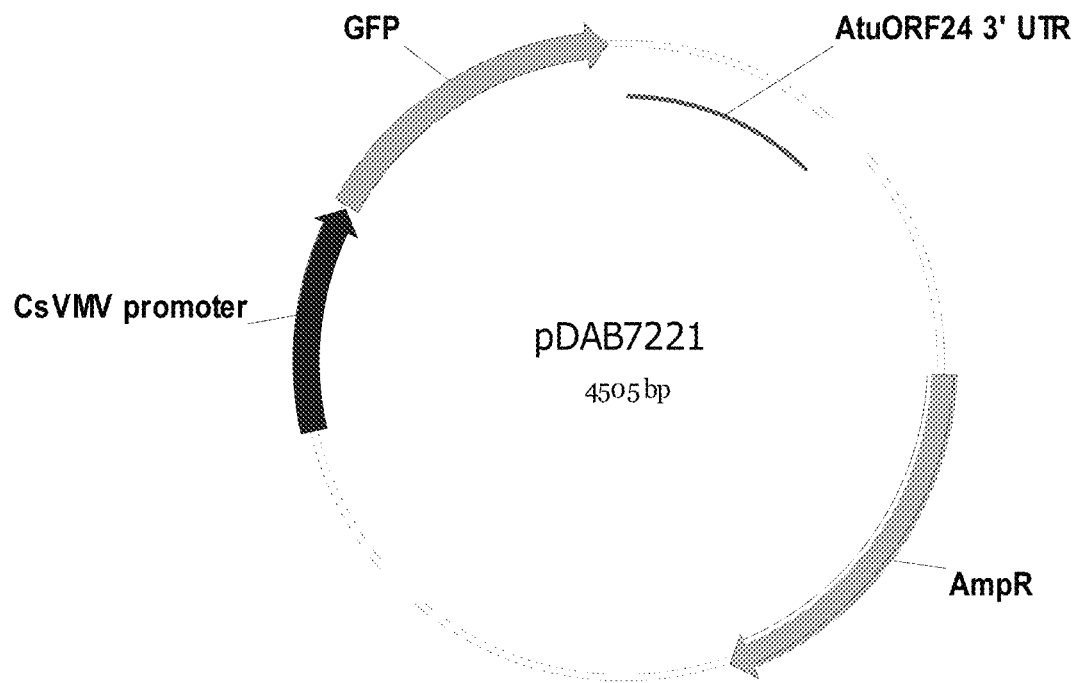

Figure 7: Schematic of probe/primers for the locus disruption assay. F2 ZFN binding sites for the FAD2 2.3 and 2.6 genes and primers used for the disruption assay are indicated.
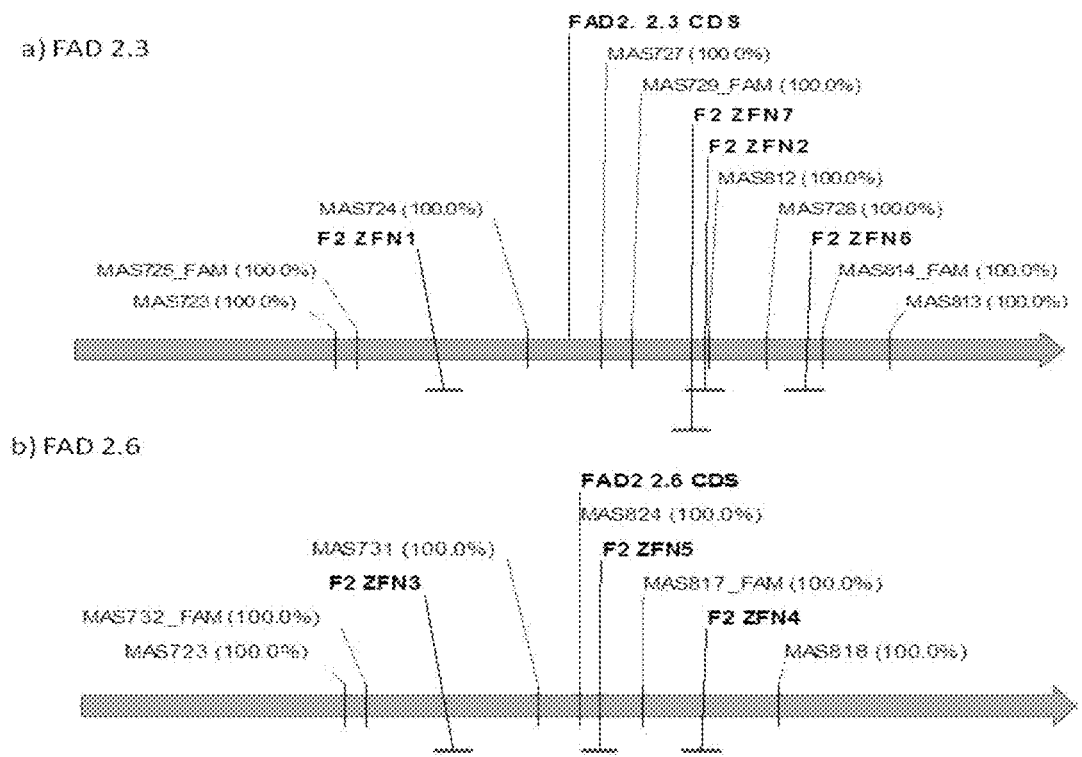

FIGURE 8:

| Name | SEQ ID NO: | FAD2 genomic sequence    inverted donor insert | Plasmid Clones with Similar Sequence |
|---|---|---|---|
| Reference | 119 | TTACTCTC<u>TCTACCGTGTTGCAACCCT</u>GAAATTTC<u>AGGGTTGCAACACGGT AGA</u>GAGAGTAA | -- |
| | | | |
| 1WT3 | 120 | TTACTCTC<u>TCTACCGTGTTGCAACCCT</u>GA___TC<u>AGGGTTGCAACACGGTA GA</u>GAGAGTAA | (1WT4,5) |
| 1WT6 | 121 | TTACTCTC<u>TCTACCGTGTTGCAACCCT</u>GAA___A<u>GGGTTGCAACACGGTA GA</u>GAGAGTAA | -- |
| 4WT1 | 122 | TTACTCTC<u>TCTACCGTGTTGCAACCCT</u>GA___<u>GGTTGCAACACGGTAG AGA</u>GAGAGTAA | (4WT2,3,4,5) |
| 4WT4 | 123 | TTACTCTC<u>TCTACCGTGTTGCAACCCT</u>GAA___60 bp deletion | (4WT6) |
| | | | |
| 1HF1 | 124 | TTACTCTC<u>TCTACCGTGTTGCAACCCT</u>GA__TTTC<u>AGGGTTGCAACACGGT AGA</u>GAGAGTAA | (1HF3,5,6) |
| 1HF2 | 125 | TTACTCTC<u>TCTACCGTGTTGCAACCCT</u>GA___TTC<u>AGGGTTGCAACACGGTA GA</u>GAGAGTAA | -- |
| 1HF4 | 126 | TTACTCTC<u>TCTACCGTGTTGCAACCCT</u>a___TTC<u>AGGGTTGCAACACGGTA GA</u>GAGAGTAA | -- |
| 6HF1 | 127 | TTACTCTC<u>TCTACCGTGTTGCAACCCT</u>GA___TTC<u>AGGGTTGCAACACGGTA GA</u>GAGAGTAA | -- |
| 6HF2 | 128 | TTACTCTC<u>TCTACCGTGTTGCAACCCT</u>GAA___TC<u>AGGGTTGCAACACGGT AGA</u>GAGAGTAA | -- |
| 6HF3 | 129 | TTACTCTC<u>TCTACCGTGTTGCAACCCT</u>GAA___A<u>GGGTTGCAACACGGTA GA</u>GAGAGTAA | (6HF5,6) |
| 6HF4 | 130 | TTACTCTC<u>TCTACCGTGTTGCAACCCT</u>c___TTTC<u>AGGGTTGCAACACGGTA GA</u>GAGAGTAA | -- |

FAD2 PERFORMANCE LOCI AND CORRESPONDING TARGET SITE SPECIFIC BINDING PROTEINS CAPABLE OF INDUCING TARGETED BREAKS

CROSS-REFERENCE TO RELATED APPLICATIONS

The present application is a continuation of U.S. patent application Ser. No. 15/292,774, filed Oct. 13, 2016, which is a divisional of U.S. patent application Ser. No. 14/019,293, filed Sep. 5, 2013, now U.S. Pat. No. 9,493,779, which claims priority to the benefit of U.S. Provisional Patent Application No. 61/697,886, filed Sep. 7, 2012, the disclosures of which are hereby incorporated by reference in their entireties.

FIELD OF THE DISCLOSURE

The present disclosure relates generally to compositions and methods for use in recombinant plant technology (for example, for generating a transgenic plant). More specifically, the present disclosure relates to plant cells and plants including loci within their genomes that may be used for the site-specific introduction of any nucleic acid of interest.

BACKGROUND

Many plants are genetically transformed with exogenous nucleic acids (e.g., transgenes) to introduce desirable traits, for example, to improve agricultural value. Examples of improvements in agricultural value that can be achieved through genetic transformation include: improved nutritional quality, increased yield, pest or disease resistance, drought and stress tolerance, improved horticultural quality (e.g., improved pigmentation and/or growth), herbicide resistance, production of industrially useful compounds and/or materials from the plant, and/or production of pharmaceuticals. The introduction of cloned genes into plant cells and recovery of stable fertile transgenic plants can be used to make a genetic modification of a plant stable through multiple generations, and thereby allow the genetic engineering of a crop plant.

In methods for genetic transformation and transgenic plant production, exogenous DNA is typically randomly introduced into the nuclear or plastid DNA of a eukaryotic plant cell, followed by isolation of cells containing integrated exogenous DNA, and subsequent regeneration of a stably transformed plant. Transgenic plants were typically generated by *Agrobacterium*-mediated transformation technology. Successes with these techniques spurred the development of other methods to introduce a nucleic acid molecule of interest into the genome of a plant, such as PEG-mediated DNA uptake in protoplasts, microprojectile bombardment, and silicon whisker-mediated transformation.

In all of these plant transformation methods, however, the exogenous nucleic acids incorporated in the plant genome are integrated randomly in the genome of the plant cell, and in unpredictable copy number. Terada et al. (2002) *Nat Biotechnol* 20(10): 1030; Terada et al. (2007) *Plant Physiol* 144(2):846; D'Halluin et al. (2008) *Plant BiotechnologyJ.* 6(1):93. For example, the transgenes are frequently integrated in the form of sequence repeats, either of the whole transgene or of parts thereof. Such a complex integration pattern commonly adversely impacts the expression level of the integrated nucleic acid (e.g., by destruction of transcribed RNA through post-transcriptional gene silencing mechanisms, or by inducing methylation of the integrated DNA). Also, the location of the integration site commonly influences the level of expression of the integrated nucleic acid. Moreover, the integration of the exogenous DNA may have a disruptive effect on the region of the genome where the integration occurs, and thereby influence or disturb the normal function of that target region to produce undesirable side-effects. The combination of factors including the foregoing results in a wide variation in the level of expression of transgene or exogenous DNA (and overall agronomic quality) between different transgenic plant cell and plant lines, even those created by the same methods. Because the integration is random, these effects are not able to be controlled by the practitioner while he or she attempts to produce a new plant with desirable characteristics.

The foregoing considerations necessitate that, whenever the effects of introducing a particular exogenous nucleic acid into a plant is investigated, a large number of transgenic plant lines must be generated and analyzed in order to obtain significant results. Likewise, in the generation of a transgenic plant containing a particular integrated nucleic acid so as to provide the transgenic plant with a desired phenotype, a large population of independently created transgenic plant lines must be created to allow the selection of a plant line with optimal expression of the nucleic acid, and with minimal or no side-effects on the overall phenotype and performance of the transgenic plant. These practical considerations take on added importance in transgenic plants created by inserting multiple exogenous nucleic acids (i.e., gene stacking). In such plants, phenomena such as post-transcriptional gene silencing may be amplified.

Several methods have been developed in an effort to control transgene insertion in plants. See, e.g., Kumar and Fladung (2001) *Trends Plant Sci.* 6:155-9. These methods rely on homologous recombination-based transgene integration, which has been successfully applied both in prokaryotes and lower eukaryotes. Paszkowski et al. (1988) *EMBO J.* 7:4021-6. However, until recently in plants, the predominant mechanism for transgene integration has been based on illegitimate recombination, which involves little homology between recombining DNA strands. A major challenge in this area is therefore the detection and selective generation of rare homologous recombination events, which are masked by far more efficient integration events via illegitimate recombination. Moreover, even if the selective generation and detection of targeted homologous recombination events is achieved, the event must be targeted to a desirable location in the host genome in order to realize the maximum benefit of this strategy.

For example, an assumed benefit of targeted genetic transformation is the reduction in event-to-event variability of transgene expression, as compared to transformation events that are obtained from random integration. A further assumed benefit is a significant reduction in the number of events required to screen introduced nucleic acids, sort transformation constructs, and produce events that contribute to desirable overall characteristics in the resulting transgenic plant. A critical factor required to realize these benefits is the identification of specific locations in the genome where transgene performance is consistent, and if possible, where adverse effects on the host plant are eliminated or minimized.

Recently, methods and compositions for targeted cleavage of genomic DNA have been described. Such targeted cleavage events can be used, for example, to induce targeted mutagenesis, induce targeted deletions of cellular DNA sequences, and facilitate targeted recombination and integration at a predetermined chromosomal locus. See, for example, Urnov et al. (2010) Nature 435(7042):646-51; United States Patent Publications 20030232410; 20050208489; 20050026157; 20050064474; 20060188987; 20090263900; 20090117617; 20100047805; 20110207221; 20110301073; 2011089775; 20110239315; 20110145940; and International Publication WO 2007/014275, the disclosures of which are incorporated by reference in their entireties for all purposes. Cleavage can occur through the use of specific nucleases such as engineered zinc finger nucleases (ZFN), transcription-activator like effector nucleases (TALENs), or using the CRISPR/Cas system with an engineered crRNA/tracr RNA ('single guide RNA') to guide specific cleavage. U.S. Patent Publication No. 20080182332 describes the use of non-canonical zinc finger nucleases (ZFNs) for targeted modification of plant genomes; U.S. Patent Publication No. 20090205083 describes ZFN-mediated targeted modification of a plant EPSPS locus; U.S. Patent Publication No. 20100199389 describes targeted modification of a plant Zp15 locus and U.S. Patent Publication No. 20110167521 describes targeted modification of plant genes involved in fatty acid biosynthesis. In addition, Moehle et al. (2007) *Proc. Natl. Acad, Sci. USA* 104(9): 3055-3060 describes using designed ZFNs for targeted gene addition at a specified locus. U.S. Patent Publication 20110041195 describes methods of making homozygous diploid organisms.

However, there remains a need for compositions and methods for modifying and/or modulating expression of FAD2 genes in plants, including generation of plants with targeted insertions of desired transgenes at the FAD2 locus.

BRIEF SUMMARY OF THE DISCLOSURE

The present disclosure describes compositions and methods for modulating expression of FAD2 genes (e.g., in plants, algae, and fungi) and the use of these loci as sites for the targeted integration of a nucleic acid sequence of interest (e.g., an exogenous nucleic acid sequence) into a host cell. In some embodiments, a host cell may contain one or more genomes with one or more FAD2 sequences (e.g., homeologues or paralogs), any or all of which may be selectively modified and/or disrupted. In specific examples, the present disclosure describes FAD2 2.3 and FAD2 2.6 genes, as well as corresponding homeologues or paralogs, in *Glycine max* (e.g., *G. max* c.v. Jack, Williams 82, X5, Westag, and Maverick) and their use as loci for targeted integration of a nucleic acid sequence of interest. As described herein, though FAD2 genes are involved in fatty acid biosynthesis in the host, their modification or disruption (e.g., by integration of an exogenous nucleic acid in the FAD2 coding sequence) unexpectedly may have no or minimal adverse effects on the resultant host organism.

Also described herein is the use of one or more particular FAD2 loci in tandem with a polypeptide capable of effecting cleavage and/or integration of specific nucleic acid sequences within the FAD2 loci. Examples of the use of FAD2 loci in tandem with a polypeptide capable of effecting cleavage and/or integration of the FAD2 loci include a polypeptide selected from the group consisting of zinc finger proteins, meganucleases, TAL domains, TALENs, RNA-guided CRISPR-Cas9, recombinases, leucine zippers, CRISPr/Cas and others known to those in the art. Particular examples include a chimeric ("fusion") protein comprising a site-specific DNA binding domain polypeptide and cleavage domain polypeptide (e.g., a nuclease), such as a ZFN protein comprising a zinc-finger polypeptide and a FokI nuclease polypeptide. For example, described herein is a demonstration of the in vitro and in vivo efficacy and specificity of particular ZFNs designed to bind and induce double stranded breaks in FAD2 2.3 and FAD2 2.6 genes, and in combinations thereof without cleaving corresponding homeologues or paralogs. In some embodiments, particular FAD2 loci may be used with any of the foregoing polypeptides to effect site-specific integration of a nucleic acid of interest that is subsequently expressed in the host while having a minimal adverse impact on the agronomic performance of the host.

In certain aspects, described herein are polypeptides comprising a DNA-binding domain that specifically binds to a FAD2 gene. In some embodiments such a polypeptide may also comprise a nuclease (cleavage) domain or half-domain (e.g., a ZFN, a recombinase, a transposase, or a homing endonuclease, including a homing endonuclease with a modified DNA-binding domain, TAL domains, TALENs, RNA-guided CRISPR-Cas9), and/or a ligase domain, such that the polypeptide may induce a targeted double-stranded break, and/or facilitate recombination of a nucleic acid of interest at the site of the break. In particular embodiments, a DNA-binding domain that targets a FAD2 locus may be a DNA-cleaving functional domain. The foregoing polypeptides may be used in some embodiments to introduce an exogenous nucleic acid into the genome of a host organism (e.g., a plant or animal species) at one or more FAD2 loci. In certain embodiments, the DNA-binding domains comprise a zinc finger protein with one or more zinc fingers (e.g., 2, 3, 4, 5, 6, 7, 8, 9 or more zinc fingers), and can which is engineered (non-naturally occurring) to bind to any sequence within a FAD2 gene. Any of the zinc finger proteins described herein may bind to a target site within the coding sequence of the target gene or within adjacent sequences (e.g., promoter or other expression elements). In certain embodiments, the zinc finger protein binds to a target site in an FAD2 gene, for example, as shown in Table 1. The recognition helix regions of exemplary FAD2-binding zinc fingers are shown in Table 2. One or more of the component zinc finger binding domains of the zinc finger protein can be a canonical (C2H2) zinc finger or a non-canonical (e.g., C3H) zinc finger (e.g., the N-terminal and/or C-terminal zinc finger can be a non-canonical finger).

Also described herein are methods for disrupting or editing a FAD2 gene. Additionally, described herein are genetically modified host organisms (e.g., transgenic plants) produced by methods according to embodiments of the invention. In particular examples, a transgenic organism produced by a method according to an embodiment of the invention may be, without limitation, algae, a fungus, a monocotyledonous plant, a dicotyledonous plant, etc. In some particular embodiments, the dicotyledonous plant may be a soybean (*Glycine max*) plant.

The FAD2 genes disclosed herein may include those found in any plant, algae, or fungi that have one or more FAD2 genes.

The foregoing and other features will become more apparent from the following detailed description of several embodiments, which proceeds with reference to the accompanying figures.

BRIEF DESCRIPTION OF THE FIGURES

FIGS. 1A through 1C show an alignment of the FAD2 2.3 coding sequences from Williams 82 (SEQ ID NO:4), Westag (SEQ ID NO:5), X5 (SEQ ID NO:6), Jack (SEQ ID NO:7), and Maverick (SEQ ID NO:8).

FIGS. 2A through 2C show an alignment of the FAD2 2.6 coding sequences from Williams 82 (SEQ ID NO:9), Westag (SEQ ID NO: 10), X5 (SEQ ID NO: 11), Jack (SEQ ID NO: 12), and Maverick (SEQ ID NO: 13).

FIG. 3 depicts activity of FAD2 2.3 and 2.6 gene designed ZFNs in a DLSSA assay. ZFNs designed to the FAD2 2.3 and 2.6 loci were evaluated for cleavage activity of FAD2 2.3 and 2.6 sequences that were cloned into mammalian cells as reporters.

FIG. 4 shows a plasmid map of pDAB115620.

FIG. 5 shows a plasmid map of pDAB115622.

FIG. 6 shows a plasmid map of pDAB7221.

FIG. 7 is a schematic depicting probe/primers for the locus disruption assay. F2 ZFN binding sites for the FAD2 2.3 and 2.6 genes and primers used for the disruption assay are indicated.

FIG. 8 shows the sequence of In-Out PCR products resulting from NHEJ targeting of a donor sequence using the F2 ZFN2 zinc finger nuclease in the FAD2 2.3 locus. The reference sequence (top of figure) represents the configuration of the targeted insertion of the donor vector in a reverse orientation. The single-stranded ends of the DNAs resulting from FokI digestion were filled in to create the reference sequence. Sanger sequences are shown. The F2 ZFN2 ZFN binding sequences are underlined. Plasmid clones with a similar sequence to the specified sequence are listed to the right.

SEQUENCES

The nucleic acid sequences are shown using standard letter abbreviations for nucleotide bases, as defined in 37 C.F.R. § 1.822. Only one strand of each nucleic acid sequence is shown, but the complementary strand is understood to be included by any reference to the displayed strand.

DETAILED DESCRIPTION

I. Overview of Several Embodiments

Embodiments of the invention establish an approach for targeted integration of exogenous nucleic acids (e.g., transgenes) in a host genome without greatly adversely impacting other phenotypes of the host beyond those affected by the integrated nucleic acid. Some embodiments may be used for "stacking" multiple nucleic acids in a single host genome. Such an approach requires the development and deployment of four inter-connected technologies: targeting technologies allowing the introduction of double stranded breaks in specific genomic DNA locations (see, e.g., Puchta et al. (1993) Nucleic Acids Res. 21:5034-40; Siebert and Puchta (2002) Plant Cell 14:1121-31; D'Halluin et al. (2008) Plant Biotechnol. J. 6(1):93-102; Cai et al. (2009) Plant Mol. Biol. 69(6):699-709; Shukla et al. (2009) Nature 459(7245):437-41); Shan et al. (2103) Nature Biotechnol. 31:686-680; Le et al. (2013) Nature Biotechnol 31: 688-691; Nekrasov et al. (2013) Nature Biotechnol. 31:691-693, Ainely et al. (2013) Plant Biotechnol. J. (On Line 19 August); delivery technologies allowing the delivery of an optimized exogenous (donor) nucleic acid (Bibikova et al. (2003) Science 300(5620): 764); integration technologies involving modification of the host genes (located either in the homologous recombination or NHEJ pathways) so as to increase the HDR or NHEJ frequencies for targeted donor DNA insertions; analytical tools to enrich and characterize targeted integration events; and specific desired host genomic locations ("performance loci") that are genetically well-defined and that support stable gene expression across generations without greatly adversely affecting the transformed host organism. See, also, United States Patent Publications 20030232410; 20050208489; 20050026157; 20050064474; 20060188987; 20090263900; 20090117617; 20100047805; 20110207221; 20110301073; 2011089775; 20110239315; 20110145940; 20080182332; 20090205083; 20100199389; 20110167521. For example, in plants, a performance locus is a locus where the negative impact on the agronomic or quality properties of a transgenic plant wherein a transgene has been inserted at the locus is negligible or non-existent.

Embodiments described herein take advantage of the unexpected finding that plant FAD2 genes are performance loci for the targeted insertion of exogenous nucleic acids (e.g., gene(s); non-coding DNA sequences, such as an Engineered Landing Pads (ELPs) (U.S. Pat. No. 8,802,921) and Engineered Transgene Insertion Platform (ETIP) (U.S. Patent Publication No. 20140090113); and plant transformation unit(s)). The ubiquitous nature of FAD2 loci in plants, and evidence that alteration or knock-out of FAD2 in canola, corn, sunflower, wheat, cotton, and soybean does not carry an agronomic or quality penalty, identifies FAD2 loci as a broad class of performance loci across commercially-relevant plant species.

Some embodiments utilize site-specific double-stranded DNA cleavage at a FAD2 locus, for example, resulting from the delivery and expression of a target-site specific DNA recognition and cleavage protein. In specific examples, such a FAD2-specific DNA recognition and cleavage protein may be, for example and without limitation, a ZFN; a TALEN; RNA-guided CRISPR-Cas9, a recombinase (e.g., Cre, Hin, RecA, Tre, and FLP recombinases); a meganuclease, and an engineered protein derived from any of the foregoing or their equivalents. Cleavage may also be effected using the CRISPR/Cas system with an engineered crRNA/tracr RNA ('single guide RNA') to guide specific cleavage. In some embodiments, such a double-strand break may be repaired via integration of a donor nucleic acid at the cleavage site within the FAD2 performance locus, for example, by Homology Directed Repair (HDR) or Non-Homologous End Joining (NHEJ).

This disclosure exemplifies the utility of FAD2 loci as performance loci, for example, by describing the FAD2 2.3 and FAD2 2.6 loci in soybean (*Glycine max*), and corresponding FAD2-specific ZFNs that may be utilized to integrate an exogenous nucleic acid at the FAD2 2.3 and/or FAD2 2.6 locus.

Embodiments of the present invention address many unsolved problems in the art. For example, the selectivity of the targeted integration approach described herein may reduce or eliminate the necessity of repeated field trials required for elimination of unwanted transgenic events, which trials are costly due to the resources involved and the burdensome regulatory requirements in this area. Furthermore, the targeted DNA insertion approaches described herein may be particularly beneficial in the process of transgene stacking.

Although the native nucleotide sequence at an endogenous FAD2 locus may be used to directly target a nucleic acid of interest, in some embodiments, a nucleic acid may first be targeted to at least one FAD2 locus of the host, such that the integration of further nucleic acid molecules of interest into the host is facilitated. In other examples, nucleotide sequences that are not homologous to native sequences of the host organism (e.g., essentially randomly generated nucleic acid sequences) that flank a DNA recognition site (e.g., zinc finger recognition sites) may be utilized.

II. Terms

As used in this application, including the claims, terms in the singular and the singular forms, "a," "an," and "the," for example, include plural referents, unless the content clearly dictates otherwise. Thus, for example, a reference to "plant," "the plant," or "a plant" also refers to a plurality of plants. Furthermore, depending on the context, use of the term, "plant," may also refer to genetically-similar or identical progeny of that plant. Similarly, the term, "nucleic acid," may refer to many copies of a nucleic acid molecule. Likewise, the term, "probe," may refer to many similar or identical probe molecules.

Numeric ranges are inclusive of the numbers defining the range, and expressly include each integer and non-integer fraction within the defined range. Unless defined otherwise, all technical and scientific terms used herein have the same meaning as commonly understood by one of ordinary skill in the art.

In order to facilitate review of the various embodiments described in this disclosure, the following explanation of specific terms is provided:

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Cross: As used herein in regard to plants, the term "cross" or "crossed" refers to the fusion of gametes via pollination to produce progeny (e.g., cells, seeds, and plants). This term encompasses both sexual crosses (i.e., the pollination of one plant by another) and selfing (i.e., self-pollination, for example, using pollen and ovule from the same plant).

Backcrossing: Backcrossing methods may be used to introduce a nucleic acid sequence into a plant. This technique has been widely used for decades to introduce new traits into plants. Jensen, N., Ed. *Plant Breeding Methodology*, John Wiley & Sons, Inc., 1988. In a typical backcross protocol, the original variety of interest (recurrent parent) is crossed to a second variety (non-recurrent parent) that carries a nucleic acid sequence of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred nucleic acid sequence from the non-recurrent parent.

Introgression: As used herein, the term "introgression" refers to the transmission of an allele (or modified allele comprising an exogenous nucleic acid) into a genetic background at a particular locus. In some embodiments, introgression of a specific allele at the locus may occur by transmitting the allele to at least one progeny via a sexual cross between two parents of the same species, where at least one of the parents has the specific allele form in its genome. Progeny comprising the specific allele may be repeatedly backcrossed to a line having a desired genetic background. Backcross progeny may be selected for the specific allele form, so as to produce a new variety wherein the specific allele form has been fixed in the genetic background. In some embodiments, introgression of a specific allele may occur by recombination between two donor genomes (e.g., in a fused protoplast), where at least one of the donor genomes has the specific allele form in its genome. Introgression may involve transmission of a specific allele form that may be, for example and without limitation, a disrupted or modified allele; a transgene; a PTU; and an ELP.

Germplasm: As used herein, the term "germplasm" refers to genetic material of or from an individual plant, a group of plants (e.g., a plant line, variety, and family), and a clone derived from a plant or group of plants. A germplasm may be part of an organism or cell, or it may be separate (e.g., isolated) from the organism or cell. In general, germplasm provides genetic material with a specific molecular makeup that is the basis for hereditary qualities of the plant. As used herein, "germplasm" refers to cells of a specific plant; seed; tissue of the specific plant (e.g., tissue from which new plants may be grown); and non-seed parts of the specific plant (e.g., leaf, stem, pollen, and cells). As used herein, the term "germplasm" is synonymous with "genetic material," and it may be used to refer to seed (or other plant material) from which a plant may be propagated. A "germplasm bank" may refer to an organized collection of different seed or other genetic material (wherein each genotype is uniquely identified) from which a known cultivar may be cultivated, and from which a new cultivar may be generated.

Gene: As used herein, the term "gene" (or "genetic element") may refer to a heritable genomic DNA sequence with functional significance. A gene may be a native nucleic acid, or a nucleic acid that has been integrated into the genome. The term "gene" may also be used to refer to, for example and without limitation, a cDNA and/or an mRNA encoded by a heritable genomic DNA sequence.

Nucleic acid molecule: As used herein, the term "nucleic acid molecule" may refer to a polymeric form of nucleotides (i.e., ribonucleotides, deoxyribonucleotides, and/or a modified form of either of the foregoing). A "nucleic acid molecule" as used herein is synonymous with "nucleic acid" and "polynucleotide." The term includes both sense and anti-sense strands of RNA, cDNA, genomic DNA, and synthetic forms and mixed polymers thereof. The term includes any topological conformation, including single-stranded, double-stranded, partially duplexed, triplexed, hairpinned, circular, and padlocked conformations. A nucleic acid molecule can include either or both of naturally-occurring and modified nucleotides. Such nucleotides may be linked together by naturally-occurring and/or non-naturally-occurring nucleotide linkages.

Nucleic acid molecules may be modified chemically or biochemically, or may contain derivatized nucleotide bases, as will be readily appreciated by those of skill in the art. Such modifications include, for example and without limitation: labels; methylation; substitution of one or more of the naturally-occurring nucleotides with an analog; and inter-nucleotide modifications (e.g., uncharged linkages, for example, methyl phosphonates, phosphotriesters, phosphoramidates, and carbamates; charged linkages, for example, phosphorothioates and phosphorodithioates; pendent moieties, for example, peptides; intercalators, for example, acridine and psoralen; chelators; alkylators; and modified linkages, for example, alpha anomeric nucleic acids).

Exogenous: An "exogenous" molecule is a molecule that is not native to a specified system (e.g., a germplasm, variety, elite variety, and/or plant) with respect to nucleotide sequence and/or genomic location (i.e., locus) for a polynucleotide (and with respect to amino acid sequence and/or cellular localization for a polypeptide). In embodiments, exogenous or heterologous polynucleotides or polypeptides may be molecules that have been artificially supplied to a biological system (e.g., a plant cell, a plant gene, a particular plant species or variety, and/or a plant chromosome) and are not native to that particular biological system. Thus, the designation of a nucleic acid as "exogenous" may indicate that the nucleic acid originated from a source other than a naturally-occurring source, or it may indicate that the nucleic acid has a non-natural configuration, genetic location, or arrangement of elements.

In contrast, for example, a "native" or "endogenous" nucleic acid is a nucleic acid (e.g., a gene) that does not contain a nucleic acid element other than those normally present in the chromosome or other genetic material on which the nucleic acid is normally found in nature. An endogenous gene transcript is encoded by a nucleotide sequence at its natural chromosomal locus, and is not artificially supplied to the cell.

Operably linked: A first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

Promoter: A promoter is a region of DNA that generally is located upstream (towards the 5' region) of a nucleic acid that enhances transcription of the nucleic acid. Promoters permit the proper activation or repression of the nucleic acid(s) with which they are operably linked. A promoter contains specific sequences that are recognized by transcription factors. These factors bind to the promoter DNA sequences and result in the recruitment of RNA polymerase, the enzyme that synthesizes the RNA from the coding region of the nucleic acid. Transformed: A vector "transforms" or "transduces" a cell when it transfers nucleic acid molecules into the cell. A cell is "transformed" by a nucleic acid molecule when the nucleic acid molecule becomes stably replicated by the cell, either by incorporation of the nucleic acid molecule into the cellular genome or by episomal replication. As used herein, the term "transformation" encompasses all techniques by which a nucleic acid molecule can be introduced into a cell. Examples include, but are not limited to: transfection with viral vectors; transformation with plasmid vectors; electroporation (Fromm et a. (1986) Nature 319:791-3); lipofection (Felgner et al. (1987) Proc. Natl. Acad. Sci. USA 84:7413-7); microinjection (Mueller et al. (1978) Cell 15:579-85); *Agrobacterium*-mediated transfer (Fraley et al. (1983) Proc. Natl. Acad. Sci. USA 80:4803-7); direct DNA uptake; and microprojectile bombardment (Klein et al. (1987) Nature 327:70).

Introduced: As used herein, the term "introduced," when referring to translocation of an exogenous nucleic acid into a cell, refers to the incorporation of the nucleic acid into the cell using any methodology available in the art. This term encompasses nucleic acid introduction methods including, for example and without limitation, transfection; transformation; and transduction.

Transgene: As used herein, the term "transgene" refers to an exogenous nucleic acid coding sequence of interest. For example, a transgene may encode an industrially or pharmaceutically useful compound, or an expression product that contributes to a desirable agricultural trait (e.g., herbicide resistance or pest resistance). In a further example, a transgene may be an antisense nucleic acid, wherein expression of the antisense nucleic acid inhibits expression of a target nucleic acid sequence. A transgene may comprise regulatory sequences operably linked to the transgene (e.g., a promoter). In some embodiments, a nucleic acid molecule of interest to be introduced by site-specific targeting at a FAD2 locus is a transgene. However, in other embodiments, a nucleic acid molecule of interest may be a PTU, an ELP, an ETIP, or an endogenous nucleic acid sequence (e.g., wherein additional, exogenous genomic copies of the endogenous nucleic acid sequence are desired).

Elements can also include DNA that encodes for a structural RNA, such as shRNA. Such RNA can modify exogenous or endogenous genes including, but not limited to affecting postings or conferring herbicide resistance.

Recombinant: As used herein, the term "recombinant" refers to a material (e.g., nucleic acid, gene, polynucleotide, and/or polypeptide) that has been altered by human intervention. For example, the arrangement of the parts or elements of a recombinant molecule may not be a native arrangement, and/or the primary sequence of the recombinant molecule may have been changed from its native sequence, e.g., to optimize its expression and/or activity. A material may be altered to produce a recombinant material within or removed from its natural environment or state. As one example, an open reading frame of a nucleic acid is recombinant if the nucleotide sequence of the open reading frame has been removed from it natural context and cloned into an artificial nucleic acid molecule (e.g., a vector). Protocols and reagents to produce recombinant molecules (e.g., recombinant nucleic acids) are common in the art, and their use is routine. The term "recombinant" may also refer herein to a cell or organism that comprises recombinant material (e.g., a plant and/or plant cell that comprises a recombinant nucleic acid). In some examples, a recombinant organism is a transgenic organism.

Vector: As used herein, the term "vector" refers to a polynucleotide or other molecule that is capable of transferring at least one nucleic acid segment(s) into a cell. A vector may optionally comprise components/elements that mediate vector maintenance and/or enable its intended use (e.g., sequences necessary for replication, genes imparting drug or antibiotic resistance, a multiple cloning site, and/or operably linked promoter/enhancer elements that enable the expression of a cloned gene). Vectors may be derived, for example, from plasmids, bacteriophages, or plant or animal viruses. A "cloning vector," "shuttle vector," or "subcloning vector" generally comprises operably linked elements to facilitate cloning or subcloning steps (e.g., a multiple cloning site containing multiple restriction endonuclease sites).

Expression Vector: The term "expression vector," as used herein, refers to a vector comprising operably linked polynucleotide sequences that may facilitate expression of a coding sequence in a particular host organism. For example, a bacterial expression vector may facilitate expression of a coding sequence in a bacterium. Likewise, a plant expression vector may facilitate expression of a coding sequence in a plant cell. Polynucleotide sequences that facilitate expression in prokaryotes may include, for example and without limitation, a promoter; an operator; and a ribosome binding site. Eukaryotic expression vectors (e.g., a plant expression vector) may comprise, for example, promoters; enhancers; termination signals; and polyadenylation signals (and other sequences) that are generally different from those used in prokaryotic expression vectors.

Sequence identity: The term "sequence identity" or "identity," as used herein in the context of two nucleic acid or polypeptide sequences, refers to the residues in the two sequences that are the same when aligned for maximum correspondence over a specified comparison window. A value of sequence identity may be determined by comparing two optimally aligned sequences (e.g., nucleic acid sequences and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The sequence identity is calculated as a percentage by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in Altschul et al. (1990) J. Mol. Biol. 215:403-10.

The National Center for Biotechnology Information (NCBI) Basic Local Alignment Search Tool (BLAST™; Altschul et al. (1990)) may be used to align sequences, and it is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with greater similarity to the reference sequences will show increasing percentage identity when assessed by this method.

As used herein, the term "substantially identical" may refer to nucleotide sequences that are more than 80% identical. For example, a substantially identical nucleotide sequence may be at least 85%, at least 86%; at least 87%; at least 88%; at least 89%; at least 90%; at least 91%; at least 92%; at least 93%; at least 94%; at least 95%; at least 96%; at least 97%; at least 98%; at least 99%; or at least 99.5% identical to the reference sequence.

Locus: As used herein, the term "locus" refers to a position on a genome that corresponds to a measurable characteristic (e.g., a trait). In some embodiments, a locus of particular interest is the genomic position of a FAD2 gene, where disruption of the gene reduces or eliminates expression of the mRNA transcribed from the wild-type gene. A locus may be defined by a probe that hybridizes to a unique nucleotide sequence contained within the locus either during Southern hybridization or PCR.

Marker: As used herein, a "marker" refers to a gene or nucleotide sequence that can be used to identify plants that are likely to have a particular allele and/or exhibit a particular trait or phenotype. A marker may be described as a variation at a given genomic locus. A genetic marker may be a short DNA sequence, such as a sequence surrounding a single base-pair change (single nucleotide polymorphism, or "SNP"), or a long sequence, for example, a minisatellite/simple sequence repeat ("SSR"). A "marker allele" refers to the version of the marker that is present in a particular plant. The term marker as used herein may refer to a cloned segment of plant chromosomal DNA (e.g., a segment comprising a FAD2 locus, or a modified and/or disrupted FAD2 locus), and may also or alternatively refer to a DNA molecule that is complementary to a cloned segment of plant chromosomal DNA. As is recognized by those of ordinary skill in the art, the process of obtaining additional, contiguous nucleotide sequence for inclusion in a marker may be repeated nearly indefinitely (limited only by the length of the chromosome), thereby identifying additional markers along the chromosome. Any and all of the above-described varieties of markers may be used in some embodiments of the present invention.

In some embodiments, the presence of a transgene or marker (which are characterized by a "target" sequence) in a germplasm may be detected through the use of a nucleic acid probe; e.g., an oligonucleotide. A probe may be a DNA molecule or an RNA molecule. An oligonucleotide probe may be prepared synthetically or by cloning. Suitable cloning vectors are well-known to those of skill in the art. RNA probes can be synthesized by means known in the art, for example, using a DNA molecule template.

An oligonucleotide probe may be labeled or unlabeled. A wide variety of techniques exist for labeling nucleic acid molecules, including, for example and without limitation, radiolabeling by nick translation; random priming; and tailing with terminal deoxytransferase, where the nucleotides employed are labeled, for example, with radioactive $^{32}P$. Other labels which may be used include, for example and without limitation, fluorophores; enzymes; enzyme substrates; enzyme cofactors; and enzyme inhibitors. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) Proc. Natl. Acad. Sci. USA 80:4045-9.

A probe may be an exact copy of a transgene or marker to be detected. A probe may also be a nucleic acid molecule comprising, or consisting of, a nucleotide sequence that is substantially identical to a cloned segment of chromosomal DNA comprising the transgene or marker to be detected. A probe may further comprise additional nucleic acid sequences, for example, promoters; transcription signals; and/or vector sequences.

A probe may contain all or a portion of the target nucleotide sequence and additional, contiguous nucleotide sequence from the genome. This is referred to herein as a "contiguous probe." The additional, contiguous nucleotide sequence is referred to as "upstream" or "downstream" of the original target, depending on whether the contiguous nucleotide sequence from the chromosome is on the 5' or the 3' side of the original marker, as conventionally understood. A probe may also contain a nucleotide sequence that is not contiguous to that of the original target; this probe is referred to herein as a "non-contiguous probe." The sequence of the non-contiguous probe may be located sufficiently close to the sequence of the original target on the chromosome so that the non-contiguous probe is linked to the original marker or transgene.

In some embodiments, a probe is a nucleic acid molecule that is "specifically hybridizable" or "specifically complementary" to an exact copy of the target to be detected. "Specifically hybridizable" and "specifically complementary" are terms that indicate a sufficient degree of complementarity, such that stable and specific binding occurs between the nucleic acid molecule and the target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology-Hybridization with Nucleic Acid Probes*, Part I, Chapter 2, Elsevier, N Y, 1993; and Ausubel et al., Eds., *Current Protocols in Molecular Biology*, Chapter 2, Greene Publishing and Wiley-Interscience, N Y, 1995.

As used herein, "stringent conditions" encompass conditions under which hybridization will only occur if there is less than 25% mismatch between the hybridization molecule and the DNA target. "Stringent conditions" include further particular levels of stringency. Thus, as used herein, "moderate stringency" conditions are those under which molecules with more than 25% sequence mismatch will not hybridize; conditions of "medium stringency" are those under which molecules with more than 15% mismatch will not hybridize; and conditions of "high stringency" are those under which sequences with more than 10% mismatch will not hybridize. Conditions of "very high stringency" are those under which sequences with more than 6% mismatch will not hybridize.

In particular embodiments, stringent conditions are hybridization at 65° C. in 6× saline-sodium citrate (SSC) buffer, 5×Denhardt's solution, 0.5% SDS, and 100 µg sheared salmon testes DNA, followed by 15-30 minute sequential washes at 65° C. in 2×SSC buffer and 0.5% SDS, followed by 1×SSC buffer and 0.5% SDS, and finally 0.2×SSC buffer and 0.5% SDS.

Linkage (dis)equilibrium: As used herein, the term "linkage equilibrium" refers to the situation where a marker and a second nucleic acid (e.g., transgene, PTU, and second marker) independently segregate; i.e., the marker and the second nucleic acid sort randomly among progeny. Nucleic acids that show linkage equilibrium are considered unlinked (whether or not they lie on the same chromosome). As used herein, the term "linkage disequilibrium" refers to the situation where a marker and a second nucleic acid segregate in a non-random manner; i.e., the nucleic acids have a recombination frequency of less than 50% (and thus by definition, are separated by less than 50 cM on the same linkage group). In some examples, nucleic acids that show linkage disequilibrium are considered linked.

Linked, tightly linked, and extremely tightly linked: As used herein, linkage between a marker and a second nucleic acid (e.g., transgene, PTU, and second marker) may refer to the phenomenon in which nucleic acids on a chromosome show a measurable probability of being passed on together to individuals in the next generation. Thus, linkage of one marker to a second nucleic acid may be measured and/or expressed as a recombination frequency. The closer two nucleic acids are to each other, the closer to "1" this probability becomes. Thus, the term "linked" may refer to one or more genes or markers that are passed together with a second nucleic acid with a probability greater than 0.5 (which is expected from independent assortment where markers/genes are located on different chromosomes). When the presence of a gene (e.g., a transgene) contributes to a phenotype in an individual, markers that are linked to the gene may be said to be linked to the phenotype. Thus, the term "linked" may refer to a relationship between a marker and a gene, or between a marker and a phenotype.

A relative genetic distance (determined by crossing over frequencies and measured in centimorgans (cM)) is generally proportional to the physical distance (measured in base pairs) that two linked markers or genes are separated from each other on a chromosome. One centimorgan is defined as the distance between two genetic markers that show a 1% recombination frequency (i.e., a crossing-over event occurs between the two markers once in every 100 cell divisions). In general, the closer one marker is to another marker or gene (whether the distance between them is measured in terms of genetic distance or physical distance) the more tightly they are linked. Because chromosomal distance is approximately proportional to the frequency of recombination events between traits, there is an approximate physical distance that correlates with recombination frequency. This correlation is generally known or readily determinable across the major crop plants (Helentjaris and Burr (eds.) (1989) *Development and Application of Molecular Markers to Problems in Plant Genetics*. Cold Spring Harbor Laboratory, Cold Spring Harbor, N.Y.; Gresshoff (ed.) (1994) *Plant Genome Analysis*. CRC Press, Boca Raton, Fla.; Lander et al. (1987) Genomics 1:174-81; Tanksley et al. (1988) "Molecular mapping of plant chromosomes," In *Chromosome Structure and Function*. Gustafson and Appels (eds.) Plenum Press, NY, pp. 157-73) and many other organisms. For example, 1 cM corresponds to about 2.5-3.0 kb in yeast, about 140 kb in *Arabidopsis*, about 400 kb in sunflower, and about 350 kb in *Eucalyptus*.

The term "linked" may refer herein to one or more nucleic acids that show a recombination frequency of less than 50% (i.e., less than 50 cM). For example, "linked" nucleic acids may recombine with a frequency of about 45% or less, about 40% or less, about 35% or less, about 30% or less, about 25% or less, about 20% or less, about 15% or less, and about 10% or less. The physical distances between such nucleic acids on the same chromosome (nucleic acids on different chromosomes are expected to be in linkage equilibrium) that correspond to the foregoing recombination frequencies depend on the host genome, and may be easily calculated as set forth, supra.

As used herein, the term "tightly-linked" may refer to one or more nucleic acids that show a recombination frequency of about 20% or less (i.e., about 20 cM or less). For example, "tightly linked" nucleic acids may recombine with a frequency of 22% or less, about 18% or less, about 16% or less, about 14% or less, about 12% or less, about 10% or less, about 8% or less, about 6% or less, about 4% or less, and about 2% or less.

As used herein, the term "extremely tightly-linked" may refer to one or more nucleic acids that show a recombination frequency of about 10% or less (i.e., about 10 cM or less). For example, "extremely tightly linked" nucleic acids may recombine with a frequency of 11% or less, about 9% or less, about 8% or less, about 7% or less, about 6% or less, about 5% or less, about 4% or less, about 3% or less, about 2% or less, and about 1% or less.

The closer a particular nucleic acid is to a gene that encodes a polypeptide that contributes to a particular phenotype (whether measured in terms of genetic or physical distance), the more tightly-linked is the particular nucleic acid to the phenotype. In view of the foregoing, it will be appreciated that nucleic acids linked to a particular gene or phenotype include those nucleic acids that are tightly linked, and those nucleic acids that are extremely tightly linked, to the gene or phenotype. In some embodiments, the closer a particular nucleic acid is to a FAD2 locus (e.g., a modified or disrupted FAD2 locus), whether measured in terms of genetic or physical distance, the more tightly-linked is the particular nucleic acid to any trait/phenotype conferred by an exogenous nucleic acid integrated at the FAD2 locus (or to a wild-type FAD2 phenotype in the case of an unmodified locus). Thus, genetic markers that are linked, tightly linked, and/or extremely tightly linked to a FAD2 locus comprising an integrated exogenous nucleic acid may be useful in an MAS program to identify organisms (e.g., plants and plant varieties) comprising the integrated nucleic acid, to identify organisms comprising a phenotype conferred by the integrated nucleic acid, and to breed such an integrated nucleic acid and/or a phenotype conferred by the integrated nucleic acid into other compatible organisms.

Marker-assisted breeding: As used herein, the term "marker-assisted breeding" may refer to an approach to breeding plants directly for one or more trait(s) (e.g., a polygenic trait). In current practice, plant breeders attempt to identify easily detectable traits, such as flower color, seed coat appearance, or isozyme variants that are linked to an agronomically desired trait. The plant breeders then follow the agronomic trait in the segregating, breeding populations by following the segregation of the easily detectable trait. However, there are very few of these linkage relationships between traits of interest and easily detectable traits available for use in plant breeding. In some embodiments of the invention, marker-assisted breeding comprises identifying one or more genetic markers (e.g., SNP, isozyme, and/or SSR markers) that are linked to a FAD2 locus wherein an exogenous nucleic acid contributing to a trait of interest has been integrated, and following the trait of interest in a segregating, breeding population by following the segregation of the one or more genetic markers. In some examples, the segregation of the one or more genetic markers may be determined utilizing a probe for the one or more genetic markers by assaying a genetic sample from a progeny plant for the presence of the one or more genetic markers. Marker-assisted breeding provides a time- and cost-efficient process for improvement of plant varieties.

Trait or phenotype: The terms "trait" and "phenotype" are used interchangeably herein. For the purposes of the present disclosure, traits of particular interest include agronomically important traits, as may be expressed, for example, in a crop plant, and the production of transgene expression products from a targeted integration event. The term "molecular phenotype" may refer to a phenotype that is detectable at the level of a population of (one or more) molecules. In some examples, the molecular phenotype may only be detectable at the molecular level. The detectable molecules of the phenotype may be nucleic acids (e.g., genomic DNA or RNA); proteins; and/or metabolites. For example, a molecular phenotype may be an expression profile for one or more gene products (e.g., at a specific stage of plant development, or in response to an environmental condition or stress).

Quantitative Trait Locus: Traits that are continuously varying due to genetic (additive, dominant, and epistatic) and environmental influences are commonly referred to as "quantitative traits." Quantitative traits may be distinguished from "qualitative," or "discrete," traits on the basis of two factors; environmental influences on gene expression that produce a continuous distribution of phenotypes, and the complex segregation pattern produced by multigenic inheritance. The identification of one or more regions of the genome linked to the expression of a quantitative trait defines such regions as Quantitative Trait Loci ("QTL").

Plant: As used herein, the term "plant" may refer to a whole plant, a cell or tissue culture derived from a plant, and/or any part of any of the foregoing. Thus, the term "plant" encompasses, for example and without limitation, whole plants; plant components and/or organs (e.g., leaves, stems, and roots); plant tissue; seed; and a plant cell. A plant cell may be, for example and without limitation, a cell in and/or of a plant, a cell isolated from a plant, and a cell obtained through culturing of a cell isolated from a plant.

A "transgenic plant" is a plant comprising within at least one of its cells an exogenous polynucleotide. The term "transgenic" is used herein to refer to any cell, cell line, callus, tissue, plant part, or plant, the genotype of which has been altered by the presence of a exogenous nucleic acid. Thus, this term encompasses transgenic organisms and cells that have been initially altered to comprise the exogenous polynucleotide, and those organisms and cells created by crosses or asexual propagation of the initial transgenic organism or cell. The term "transgenic," as used herein, does not encompass genome (chromosomal or extra-chromosomal) alternations introduced by conventional plant breeding methods (e.g., crosses of only non-transgenic organisms) or by naturally-occurring events (e.g., random cross-fertilization, non-recombinant viral infection, non-recombinant bacterial transformation, non-recombinant transposition, and spontaneous mutation).

A plant "line," "variety," or "strain" is a group of individual plants having the same parentage. Plants of a line generally are inbred to some degree, and are generally homozygous and homogeneous at most genetic loci (e.g., a FAD2 locus). A "subline" may refer to an inbred subset of descendents from a common progenitor that are genetically distinct from other similarly inbred subsets descended from the same progenitor. In some embodiments, a "subline" may be produced by inbreeding seed from an individual transgenic plant selected at the F3 to F5 generation until the residual segregating loci are homozygous across most or all loci.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197, WO 02/099084 and U.S. Publication No. 20110301073.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and – cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528, 2008/0131962 and 2011/0201055, incorporated herein by reference in their entireties.

Means for generating a double strand DNA break: As used herein, the term "means for generating a double strand DNA break" is intended to invoke the special claiming provisions authorized by Congress in 35 U.S.C. § 112, sixth paragraph. Specifically, a "means for generating a double strand DNA break" refers to a molecular structure that is capable of cleaving both strands of a double-stranded DNA molecule. Such structures include polypeptide domains comprised within many known nuclease proteins, for example, the FokI nuclease domain, the catalytic domain is selected from the group consisting of proteins Mmel, Colicin-E7 (CEA7_ECOLX), Colicin-E9, APFL, EndA, Endo I (END1_EC0LI), Human Endo G (NUCG HUMAN), Bovine Endo G (NUCG_BOVIN), R.HinPll, 1-Basl, 1-Bmol, 1-Hmul, 1-Tevl, 1-Tevll, 1-Tevlll, 1-Twol, R.Mspl, R.Mval, NucA, NucM, Vvn, Vvn_CLS, Staphylococcal nuclease (NUC_STAAU), Staphylococcal nuclease (NUC_STAHY), Micrococcal nuclease (NUC_SHIFL), Endonuclease yncB, Endodeoxyribonuclease I (ENRN BPT7), Metnase, Nb.BsrDI, BsrDI A, Nt.BspD61 (R.BspD61 large subunit), ss.BspD61 (R.BspD61 small subunit), R.PIel, Mlyl, Alwl, Mval2691, Bsrl, Bsml, Nb.BtsCI, Nt.BtsCI, R1.Btsl, R2.Btsl, BbvCI subunit 1, BbvCI subunit 2, BpulOI alpha subunit, BpulOI beta subunit, Bmrl, Bfil, 1-Crel, hExol (EX01JHUMAN), Yeast Exol (EX01_YEAST), E. coli Exol, Human TREX2, Mouse TREX1, Human TREX1, Bovine TREX1, Rat TREX1, Human DNA2, Yeast DNA2 (DNA2_YEAST).

Means for repairing a double strand DNA break: As used herein, the term "means for repairing a double strand DNA break" is also intended to invoke the special claiming provisions authorized by Congress in 35 U.S.C. § 112, sixth paragraph. Specifically, a "means for repairing a double strand DNA break" refers to a molecular structure that is capable of facilitating/catalyzing the joining of the ends of double-stranded DNA molecules, for example, by joining ends generated by cleaving a single double-stranded DNA molecule, or by joining one end generated by cleaving a single double-stranded DNA molecule with the end of an exogenous double-stranded DNA molecule. Such structures include polypeptide domains comprised within many known ligase proteins, for example, Cre recombinase. In some examples, the same molecular structure may serve as both a means for generating a double strand DNA break and a means for repairing a double strand DNA break, where the same structure facilitates both the cleavage and repair of double-stranded DNA molecules (e.g., Hin recombinase).

The induction of the site specific double stranded breaks in the genome induces the host plant cell DNA repair pathway which resolves the double stranded break through homology-directed repair (HDR) or non-homologous end-joining (NHEJ) repair. In plants, the scientific literature reports that precise gene or donor DNA integration into native genomic or at pre-engineered locations have involved incoming donor DNA construct(s) that comprise varying amounts of sequence homologous to the sequences flanking the targeted double stranded break. The integration of such donors into the specific target locus presumably has relied on the HDR pathway. Exclusively relying on the HDR approach for gene targeting in plants can have limitations due to reports that the HDR repair pathway is not the dominate DNA repair pathway when compared to NHEJ. The published plant scientific literature utilizing target specific DNA breaks (ZFN, TALeNs, or Engineered Meganucleases, etc.) the NHEJ pathway has been reported as the method to introduce specific point mutations (insertions, or deletions) into the genome. Here we report that site specific double stranded breaks (induced by ZFN, TALeNs, etc.) in the presents of various donor DNA design with homology regions of 0 to <10 bp can be specifically inserted at targeted break via the NHEJ repair pathway in plants. A variety of different DNA donor designs with zero homology to small 1-10 bp of ranging from linear to circular, single stranded to double stranded can be targeted to specific locations using the NHEJ pathway. NHEJ based donor DNA plant genome targeting can be based on "sticky end capture", where the targeted double stranded break in the genome generated by Fok1 (or other Type II endonuclease domains) and the corresponding sticky ends are on the NHEJ donor DNA designs. The sticky ends donor DNA can be delivered directly to the cell as linear donor DNA with predefined overhangs. An alternative approach is to produce the donor DNA sticky ends in vivo by co-delivering the host target ZFN and a circular DNA donor molecule that contains at least one ZFN recognition site that is identical to the target recognition site. Expression of at least one ZFN cuts the host genomic DNA (native or pre-engineered) and the circular donor DNA to produce sticky ends that are resolved using the hosts NHEJ repair pathway.

It is possible to have one or more ZFN cuts sites on the donor molecule (a single ZFN cut site to linearize the entire donor molecule, 2 of the same ZFN sites to release a smaller donor DNA fragment or 2 different ZFN sites to release a fragment from the donor and a corresponding fragment from the host genomic DNA (DNA replacement).

Thus, the donor polynucleotide can be DNA or RNA, single-stranded and/or double-stranded and can be introduced into a cell in linear or circular form. See, e.g., U.S. Patent Publication Nos. 20100047805 and 20110207221. In certain, embodiments of the present invention may also include linear exogenous (donor) nucleic acid(s), compositions comprising these nucleic acids and methods of making and using these linear donor molecules. In certain embodiments, the linear donor molecule stably persists in the cell into which it is introduced. In other embodiments, the linear donor molecule is modified to resist exonucleolytic cleavage, for example by placing one or more phosphorothioate phosphodiester bonds between one or more base pairs on the ends of the donor molecule. The linear exogenous nucleic acid may also include single stranded specific DNA.

III. FAD2 Performance Loci

The loci designated FAD2 (fatty acid desaturase 2) are included in QTLs involved in the inheritance of the complex multigenic trait of fatty acid content in plants. FAD2 encodes the enzyme responsible for the desaturation of oleic acid (18:1) to linoleic acid (C18:2). Tanhuanpaa et a. (1998) Mol. Breed. 4:543-50; Schierholt et al. (2001) Crop Sci. 41:1444-9.

Within the plant oil biosynthetic pathway the fatty acid desaturases (FADs) play a key role in plant lipid biosynthesis and their activity significantly influences the fatty acid composition. FADs are abundant in plants, and expression analysis suggested that FAD mRNAs are produced in over-abundance. Furthermore, FAD genes are expressed in various, tissues, and cell types, as well as subcellular compartments including the plastid and endoplasmic reticulum.

The fatty acid composition of plants, and the performance of oils produced therefrom in many applications, is determined by the relative concentrations of the major fatty acid constituents; oleic, linoleic, and linolenic (C18:3). The concentrations of these fatty acids are predominantly regulated by the function of the enzymes FAD2 and FAD3. Oleic acid is converted to linoleic acid and linolenic acid in plants according to the scheme:

FAD2 genes have been identified in major plant and algal species including but not limited to maize, soybean, cotton, *Arabidopsis*, wheat, forage grasses, rice, sunflower and *Brassica*, and modification of FAD2 expression leads to altered fatty acid profiles in such organisms. Furthermore, plants comprising modified FAD2 genes have been commercialized, and disruption of a FAD2 gene has been shown to be able to improve the nutritional and functional properties of oil produced by a host plant without an agronomic penalty to the host plant. For example, canola and sunflower varieties that have been commercialized under the Nexera® brand (Dow AgroSciences, LLC) are characterized by a higher oleic acid, lower linoleic aced, and lower linolenic acid (and lower saturated fatty acid) composition, when compared to wild-type canola and sunflower profiles.

As described in Chi, X., et al., ((2011) Genome-wide analysis of fatty acid desaturases in soybean (*Glycine max*). *Plant Molecular Biology Reports* 29, 769-783), herein incorporated by reference; the known functional gene copies of FAD2 in soybean were phylogenetically located into nine subfamilies with the *Arabidopsis* counterparts, FAB2, FAD2, FAD3, FAD5, FAD6, FAD7, FAD8, SLD1, and DES 1. Twenty-nine desaturase genes were found to be distributed on at least 15 of the 20 soybean chromosomes. The gene structures and motif compositions were considerably conserved among the subfamilies. The majority of desaturase genes showed specific temporal and spatial expression patterns across different tissues and developmental stages based on microarray data analyses.

FAD2 loci may be modified and/or disrupted in a plant without detrimentally affecting the value of the plant, and for many purposes, with an actual increase in its value, including alteration of FAD2 expression, alteration of oil content/ratios and/or integration and expression of desired transgenes. Furthermore, according to the ubiquitous nature of FAD loci in plants, FAD2 loci may be modified and/or disrupted without detriment for at least some purposes in many species, including, for example and without limitation: canola; soybean; maize; wheat; forage grasses; *Brassica* sp.; rice, tomatoes, barley; oats; sorghum; cotton; and sunflower, as well as fungi and algae. Embodiments of the invention include FAD2 loci, and the use thereof as performance loci for integration of exogenous nucleic acids. In examples, a FAD2 locus exhibits at least one of several features that have been found to be desirable within the context of its use as a performance locus, including, for example and without limitation: that there is an approximately consistent level of expression during the life cycle of the host organism; and surprisingly, that insertion of donor DNA at a FAD2 locus does not induce a quality or fitness penalty on the host.

In some embodiments of the present invention, at least one FAD2 locus (e.g., a FAD2 2.3 locus and FAD2 2.6 locus) is used as a target site for the site-specific integration of an exogenous nucleic acid (e.g., a nucleic acid comprising a nucleotide sequence encoding a polypeptide of interest). In particular embodiments, integration of the exogenous nucleic acid results in a modified locus. For example, integration of the exogenous nucleic acid may modify the locus so as to produce a disrupted (i.e., inactivated) FAD2 gene.

In some embodiments, a FAD2 locus may comprise a nucleotide sequence that is specifically hybridizable to the complement of a nucleotide sequence selected from the group consisting of SEQ ID NOs: 14 to SEQ ID NO: 20. For example, a FAD2 locus may comprise a nucleotide sequence selected from the group consisting of SEQ ID NOs: 14 to SEQ ID NO: 20. In some embodiments, a FAD2 locus may comprise a nucleotide sequence that is substantially identical to a nucleotide sequence selected from the group consisting of SEQ ID NOs: 14 to SEQ ID NO: 20. For example, in some embodiments, a FAD2 locus is a FAD2 homologue (e.g., an ortholog or a paralog) that comprises a nucleotide sequence that is at least about 85% identical to a nucleotide sequence selected from the group consisting of SEQ ID NOs: 14 to SEQ ID NO: 20. A FAD2 homologue may comprise a nucleotide sequence that is, for example and without limitation: at least 80%; at least 85%; at least about 90%; at least about 91%; at least about 92%; at least about 93%; at least about 94%; at least about 95%; at least about 96%; at least about 97%; at least about 98%; at least about 99%; at least about 99.5%; 99.6%, 99.7%, 99.8% and/or at least about 99.9% identical to a nucleotide sequence selected from the group consisting of SEQ ID NOs: 14 to SEQ ID NO: 20. Such a FAD2 homologue may be readily identified and isolated from any complete or partial genome readily available to those of skill in the art for a variety of organisms.

IV. Targeted Integration of a Nucleic Acid at a FAD2 Locus

Site-specific integration of an exogenous nucleic acid at a FAD2 locus may be accomplished by any technique known to those of skill in the art. In some embodiments, integration of an exogenous nucleic acid at a FAD2 locus comprises contacting a cell (e.g., an isolated cell or a cell in a tissue or organism) with a nucleic acid molecule comprising the exogenous nucleic acid. In examples, such a nucleic acid molecule may comprise nucleotide sequences flanking the exogenous nucleic acid that facilitate homologous recombination between the nucleic acid molecule and at least one FAD2 locus. In particular examples, the nucleotide sequences flanking the exogenous nucleic acid that facilitate homologous recombination may be complementary to endogenous nucleotides of the FAD2 locus. In particular examples, the nucleotide sequences flanking the exogenous nucleic acid that facilitate homologous recombination may be complementary to previously integrated exogenous nucleotides. In some embodiments, a plurality of exogenous nucleic acids may be integrated at one FAD2 locus, such as in gene stacking.

Integration of a nucleic acid at a FAD2 locus may be facilitated (e.g., catalyzed) in some embodiments by endogenous cellular machinery of a host cell, such as, for example and without limitation, endogenous DNA and endogenous recombinase enzymes. In some embodiments, integration of a nucleic acid at a FAD2 locus may be facilitated by one or more factors (e.g., polypeptides) that are provided to a host cell. For example, nuclease(s), recombinase(s), and/or ligase polypeptides may be provided (either independently or as part of a chimeric polypeptide) by contacting the polypeptides with the host cell, or by expressing the polypeptides within the host cell. Accordingly, in some examples, a nucleic acid comprising a nucleotide sequence encoding at least one nuclease, recombinase, and/or ligase polypeptide may be introduced into the host cell, either concurrently or sequentially with a nucleic acid to be integrated site-specifically at a FAD2 locus, wherein the at least one nuclease, recombinase, and/or ligase polypeptide is expressed from the nucleotide sequence in the host cell.

A. DNA-Binding Polypeptides

In some embodiments, site-specific integration may be accomplished by utilizing factors that are capable of recognizing and binding to particular nucleotide sequences, for example, in the genome of a host organism. For instance, many proteins comprise polypeptide domains that are capable of recognizing and binding to DNA in a site-specific manner. A DNA sequence that is recognized by a DNA-binding polypeptide may be referred to as a "target" sequence. Polypeptide domains that are capable of recognizing and binding to DNA in a site-specific manner generally fold correctly and function independently to bind DNA in a site-specific manner, even when expressed in a polypeptide other than the protein from which the domain was originally isolated. Similarly, target sequences for recognition and binding by DNA-binding polypeptides are generally able to be recognized and bound by such polypeptides, even when present in large DNA structures (e.g., a chromosome), particularly when the site where the target sequence is located is one known to be accessible to soluble cellular proteins (e.g., a gene).

While DNA-binding polypeptides identified from proteins that exist in nature typically bind to a discrete nucleotide sequence or motif (e.g., a consensus recognition sequence), methods exist and are known in the art for modifying many such DNA-binding polypeptides to recognize a different nucleotide sequence or motif. DNA-binding polypeptides include, for example and without limitation: zinc finger DNA-binding domains; leucine zippers; UPA DNA-binding domains; GAL4; TAL; LexA; a Tet repressor; LacR; and a steroid hormone receptor.

In some examples, a DNA-binding polypeptide is a zinc finger. Individual zinc finger motifs can be designed to target and bind specifically to any of a large range of DNA sites. Canonical Cys2His2 (as well as non-canonical Cys3His) zinc finger polypeptides bind DNA by inserting an α-helix into the major groove of the target DNA double helix. Recognition of DNA by a zinc finger is modular; each finger contacts primarily three consecutive base pairs in the target, and a few key residues in the polypeptide mediate recognition. By including multiple zinc finger DNA-binding domains in a targeting endonuclease, the DNA-binding specificity of the targeting endonuclease may be further increased (and hence the specificity of any gene regulatory effects conferred thereby may also be increased). See, e.g., Urnov et al. (2005) Nature 435:646-51. Thus, one or more zinc finger DNA-binding polypeptides may be engineered and utilized such that a targeting endonuclease introduced into a host cell interacts with a DNA sequence that is unique within the genome of the host cell.

Preferably, the zinc finger protein is non-naturally occurring in that it is engineered to bind to a target site of choice. See, for example, See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In some examples, a DNA-binding polypeptide is a DNA-binding domain from GAL4. GAL4 is a modular transactivator in *Saccharomyces cerevisiae*, but it also operates as a transactivator in many other organisms. See, e.g., Sadowski et al. (1988) Nature 335:563-4. In this regulatory system, the expression of genes encoding enzymes of the galactose metabolic pathway in *S. cerevisiae* is stringently regulated by the available carbon source. Johnston (1987) Microbiol. Rev. 51:458-76. Transcriptional control of these metabolic enzymes is mediated by the interaction between the positive regulatory protein, GAL4, and a 17 bp symmetrical DNA sequence to which GAL4 specifically binds (the UAS).

Native GAL4 consists of 881 amino acid residues, with a molecular weight of 99 kDa. GAL4 comprises functionally autonomous domains, the combined activities of which account for activity of GAL4 in vivo. Ma and Ptashne (1987) Cell 48:847-53); Brent and Ptashne (1985) Cell 43(3 Pt 2):729-36. The N-terminal 65 amino acids of GAL4 comprise the GAL4 DNA-binding domain. Keegan et al. (1986) Science 231:699-704; Johnston (1987) Nature 328: 353-5. Sequence-specific binding requires the presence of a divalent cation coordinated by 6 Cys residues present in the DNA binding domain. The coordinated cation-containing domain interacts with and recognizes a conserved CCG triplet at each end of the 17 bp UAS via direct contacts with the major groove of the DNA helix. Marmorstein et al. (1992) Nature 356:408-14. The DNA-binding function of the protein positions C-terminal transcriptional activating domains in the vicinity of the promoter, such that the activating domains can direct transcription.

Additional DNA-binding polypeptides that may be utilized in certain embodiments include, for example and without limitation, a binding sequence from a AVRBS3-inducible gene; a consensus binding sequence from a AVRBS3-inducible gene or synthetic binding sequence engineered therefrom (e.g., UPA DNA-binding domain); TAL; LexA (see, e.g., Brent & Ptashne (1985), supra); LacR (see, e.g., Labow et al. (1990) Mol. Cell. Biol. 10:3343-56; Baim et al. (1991) Proc. Natl. Acad. Sci. USA 88(12):5072-6); a steroid hormone receptor (Ellliston et al. (1990) J. Biol. Chem. 265:11517-121); the Tet repressor (U.S. Pat. No. 6,271,341) and a mutated Tet repressor that binds to a tet operator sequence in the presence, but not the absence, of tetracycline (Tc); the DNA-binding domain of NF-κB; and components of the regulatory system described in Wang et al. (1994) Proc. Natl. Acad. Sci. USA 91(17):8180-4, which utilizes a fusion of GAL4, a hormone receptor, and VP 16.

In certain embodiments, the DNA-binding domain of one or more of the nucleases used in the methods and compositions described herein comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like (TAL) effectors which mimic plant transcriptional activators and manipulate the plant transcriptome (see Kay et al (2007) Science 318:648-651). These proteins contain a DNA binding domain and a transcriptional activation domain. One of the most well characterized TAL-effectors is AvrBs3 from *Xanthomonas campestgris* pv. Vesicatoria (see Bonas et al (1989) Mol Gen Genet 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) J Plant Physiol 163(3): 256-272). In addition, in the phytopathogenic bacteria *Ralstonia solanacearum* two genes, designated brg1 1 and hpx17 have been found that are homologous to the AvrBs3 family of *Xanthomonas* in the *R. solanacearum* biovar 1 strain GMI1000 and in the biovar 4 strain RS1000 (See Heuer et al (2007) Appl and Envir Micro 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. Nos. 8,420,782 and 8,440,431 and U.S. Patent Publication No. 20110301073.

In other embodiments, the nuclease comprises a CRISPR/Cas system. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Wastson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In particular embodiments, a DNA-binding polypeptide specifically recognizes and binds to a target nucleotide sequence comprised within a genomic nucleic acid of a host organism. Any number of discrete instances of the target nucleotide sequence may be found in the host genome in some examples. The target nucleotide sequence may be rare within the genome of the organism (e.g., fewer than about 10, about 9, about 8, about 7, about 6, about 5, about 4, about 3, about 2, or about 1 copy(ies) of the target sequence may exist in the genome). For example, the target nucleotide sequence may be located at a unique site within the genome of the organism. Target nucleotide sequences may be, for example and without limitation, randomly dispersed throughout the genome with respect to one another; located in different linkage groups in the genome; located in the same linkage group; located on different chromosomes; located on the same chromosome; located in the genome at sites that are expressed under similar conditions in the organism (e.g., under the control of the same, or substantially functionally identical, regulatory factors); and located closely to one another in the genome (e.g., target sequences may be comprised within nucleic acids integrated as concatemers at genomic loci).

B. Targeting Endonucleases

In particular embodiments, a DNA-binding polypeptide that specifically recognizes and binds to a target nucleotide sequence may be comprised within a chimeric polypeptide, so as to confer specific binding to the target sequence upon the chimeric polypeptide. In examples, such a chimeric polypeptide may comprise, for example and without limitation, nuclease, recombinase, and/or ligase polypeptides, as these polypeptides are described above. Chimeric polypeptides comprising a DNA-binding polypeptide and a nuclease, recombinase, and/or ligase polypeptide may also comprise other functional polypeptide motifs and/or domains, such as for example and without limitation: a spacer sequence positioned between the functional polypeptides in the chimeric protein; a leader peptide; a peptide that targets the fusion protein to an organelle (e.g., the nucleus); polypeptides that are cleaved by a cellular enzyme; peptide tags (e.g., Myc, His, etc.); and other amino acid sequences that do not interfere with the function of the chimeric polypeptide.

Functional polypeptides (e.g., DNA-binding polypeptides and nuclease polypeptides) in a chimeric polypeptide may be operatively linked. In some embodiments, functional polypeptides of a chimeric polypeptide may be operatively linked by their expression from a single polynucleotide encoding at least the functional polypeptides ligated to each other in-frame, so as to create a chimeric gene encoding a chimeric protein. In alternative embodiments, the functional polypeptides of a chimeric polypeptide may be operatively linked by other means, such as by cross-linkage of independently expressed polypeptides.

In some embodiments, a DNA-binding polypeptide that specifically recognizes and binds to a target nucleotide sequence may be comprised within a natural isolated protein (or mutant thereof), wherein the natural isolated protein or mutant thereof also comprises a nuclease polypeptide (and may also comprise a recombinase and/or ligase polypeptide). Examples of such isolated proteins include TALENs, recombinases (e.g., Cre, Hin, Tre, and FLP recombinase), RNA-guided CRISPR-Cas9, and meganucleases.

As used herein, the term "targeting endonuclease" refers to natural or engineered isolated proteins and mutants thereof that comprise a DNA-binding polypeptide and a nuclease polypeptide, as well as to chimeric polypeptides comprising a DNA-binding polypeptide and a nuclease. Any targeting endonuclease comprising a DNA-binding polypeptide that specifically recognizes and binds to a target nucleotide sequence comprised within a FAD2 locus (e.g., either because the target sequence is comprised within the native sequence at the locus, or because the target sequence has been introduced into the locus, for example, by recombination) may be utilized in certain embodiments.

Some examples of chimeric polypeptides that may be useful in particular embodiments of the invention include, without limitation, combinations of the following polypeptides: zinc finger DNA-binding polypeptides; a FokI nuclease polypeptide; TALE domains; leucine zippers; transcription factor DNA-binding motifs; and DNA recognition and/or cleavage domains isolated from, for example and without limitation, a TALEN, a recombinase (e.g., Cre, Hin, RecA, Tre, and FLP recombinases), RNA-guided CRISPR-Cas9, a meganuclease; and others known to those in the art. Particular examples include a chimeric protein comprising a site-specific DNA binding polypeptide and a nuclease polypeptide. Chimeric polypeptides may be engineered by methods known to those of skill in the art to alter the recognition sequence of a DNA-binding polypeptide comprised within the chimeric polypeptide, so as to target the chimeric polypeptide to a particular nucleotide sequence of interest.

In certain embodiments, the chimeric polypeptide comprises a DNA-binding domain (e.g., zinc finger, TAL-effector domain, etc.) and a nuclease (cleavage) domain. The cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding, for example, such that one or more exogenous sequences (donors/trangenes) are integrated at or near the binding (target) sites. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Patent Publication No. 20070134796, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055). Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

C. Zinc Finger Nucleases

In specific embodiments, a chimeric polypeptide is a custom-designed zinc finger nuclease (ZFN) that may be designed to deliver a targeted site-specific double-strand DNA break into which an exogenous nucleic acid, or donor DNA, may be integrated (See co-owned US Patent publication 20100257638, incorporated by reference herein). ZFNs are chimeric polypeptides containing a non-specific cleavage domain from a restriction endonuclease (for example, FokI) and a zinc finger DNA-binding domain polypeptide. See, e.g., Huang et al. (1996) J. Protein Chem. 15:481-9; Kim et al. (1997a) Proc. Natl. Acad. Sci. USA 94:3616-20; Kim et al. (1996) Proc. Natl. Acad. Sci. USA 93:1156-60; Kim et al. (1994) Proc Natl. Acad. Sci. USA 91:883-7; Kim et al. (1997b) Proc. Natl. Acad. Sci. USA 94:12875-9; Kim et al. (1997c) Gene 203:43-9; Kim et al. (1998) Biol. Chem. 379:489-95; Nahon and Raveh (1998) Nucleic Acids Res. 26:1233-9; Smith et al. (1999) Nucleic Acids Res. 27:674-81. In some embodiments, the ZFNs comprise non-canonical zinc finger DNA binding domains (see co-owned US Patent publication 20080182332, incorporated by reference herein). The FokI restriction endonuclease must dimerize via the nuclease domain in order to cleave DNA and introduce a double-strand break. Consequently, ZFNs containing a nuclease domain from such an endonuclease also require dimerization of the nuclease domain in order to cleave target DNA. Mani et al. (2005) Biochem. Biophys. Res. Commun. 334:1191-7; Smith et al. (2000) Nucleic Acids Res. 28:3361-9. Dimerization of the ZFN can be facilitated by two adjacent, oppositely oriented DNA-binding sites. Id.

The flexibility and specificity of the ZFN system provides a level of control previously unachievable by known recombinase-mediated gene editing strategies. As one example, ZFNs can be easily engineered, for example, to recognize specific nucleic acid sequences. Wu et al. (2007) Cell. Mol. Life Sci. 64:2933-44 (See, US Patent Publications 20090205083, 20110189775, 20110167521 and 20100199389, incorporated by reference in their entireties herein). Randomization of the codons for zinc finger recognition residues allows the selection of new fingers that have high affinity for arbitrarily chosen DNA sequences. Furthermore, zinc fingers are natural DNA-binding molecules, and engineered zinc fingers have been shown to act on their designed targets in living cells. Thus, nucleases based on zinc fingers are targetable to specific but arbitrary recognition sites.

In particular examples, a method for the site-specific integration of an exogenous nucleic acid into at least one FAD2 performance locus of a host comprises introducing into a cell of the host a ZFN, wherein the ZFN recognizes and binds to a target nucleotide sequence, wherein the target nucleotide sequence is comprised within at least one FAD2 locus of the host. In certain examples, the target nucleotide sequence is not comprised within the genome of the host at any other position than the at least one FAD2 locus. For example, a DNA-binding polypeptide of the ZFN may be engineered to recognize and bind to a target nucleotide sequence identified within the at least one FAD2 locus (e.g., by sequencing the FAD2 locus). A method for the site-specific integration of an exogenous nucleic acid into at least one FAD2 performance locus of a host that comprises introducing into a cell of the host a ZFN may also comprise introducing into the cell an exogenous nucleic acid, wherein recombination of the exogenous nucleic acid into a nucleic acid of the host comprising the at least one FAD2 locus is facilitated by site-specific recognition and binding of the ZFN to the target sequence (and subsequent cleavage of the nucleic acid comprising the FAD2 locus).

V. Exogenous Nucleic Acids for Integration at a FAD2 Locus

Embodiments of the invention may include one or more nucleic acids selected from the group consisting of: an exogenous nucleic acid for site-specific integration in at least one FAD2 locus, for example and without limitation, a PTU, ELP, ETIP or an ORF; a nucleic acid comprising a nucleotide sequence encoding a targeting endonuclease; and a vector comprising at least one of either or both of the foregoing. Thus, particular nucleic acids for use in some embodiments include nucleotide sequences encoding a polypeptide, structural nucleotide sequences, and/or DNA-binding polypeptide recognition and binding sites.

A. Exogenous Nucleic Acid Molecules for Site-Specific Integration

As noted above, insertion of an exogenous sequence (also called a "donor sequence" or "donor" or "transgene") is provided, for example for expression of a polypeptide, correction of a mutant gene or for increased expression of a wild-type gene. It will be readily apparent that the donor sequence is typically not identical to the genomic sequence where it is placed. A donor sequence can contain a nonhomologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. See, e.g., U.S. Patent Publication Nos. 20100047805, 20110281361, 20110207221 and U.S. Patent Publication No. 20130326645. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally integrated so that its expression is driven by the endogenous promoter at the integration site, namely the promoter that drives expression of the endogenous gene into which the donor is integrated (e.g., FAD2). However, it will be apparent that the donor may comprise a promoter and/or enhancer, for example a constitutive promoter or an inducible or tissue specific promoter.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Exogenous nucleic acids that may be integrated in a site-specific manner into at least one FAD2 locus, so as to modify the FAD2 locus, in embodiments include, for example and without limitation, nucleic acids comprising a nucleotide sequence encoding a polypeptide of interest; nucleic acids comprising an agronomic gene; nucleic acids comprising a nucleotide sequence encoding an RNAi molecule; or nucleic acids that disrupt the FAD2 gene.

In some embodiments, an exogenous nucleic acid is integrated at a FAD2 locus, so as to modify the FAD2 locus, wherein the nucleic acid comprises an agronomic gene or nucleotide sequence encoding a polypeptide of interest, such that the agronomic gene or nucleotide sequence is expressed in the host from the FAD2 locus. In some examples, the polypeptide of interest (e.g., a foreign protein) is expressed from a nucleotide sequence encoding the polypeptide of interest in commercial quantities. In such examples, the polypeptide of interest may be extracted from the host cell, tissue, or biomass. In some embodiments, the host is a plant, and plant material provided for commercial production of a polypeptide of interest may be a plant, plant part, plant tissue, or plant cell. In some examples, the plant part may be plant seed. Protein extraction from a plant biomass may be accomplished by known methods which are discussed, for example, in Heney and Orr (1981) *Anal. Biochem.* 114:92-6.

Likewise, agronomic genes may be expressed in transformed plant cells, plants, and/or their progeny. For example, a plant may be genetically engineered via methods of particular embodiments to express various phenotypes of agronomic interest from at least one FAD2 locus.

In some embodiments, nucleic acids comprising an agronomic gene or nucleotide sequence encoding a polypeptide of interest may include, for example and without limitation: a gene that confers resistance to a pests or disease (See, e.g., Jones et al. (1994) *Science* 266:789 (cloning of the tomato Cf-9 gene for resistance to *Cladosporium fulvum*); Martin et al. (1993) *Science* 262:1432; Mindrinos et al. (1994) *Cell* 78:1089 (RSP2 gene for resistance to *Pseudomonas syringae*); PCT International Patent Publication No. WO 96/30517 (resistance to soybean cyst nematode); PCT International Patent Publication No. WO 93/19181); a gene that encodes a *Bacillus thuringiensis* protein, a derivative thereof, or a synthetic polypeptide modeled thereon (See, e.g., Geiser et al. (1986) *Gene* 48:109 (cloning and nucleotide sequence of a Bt δ-endotoxin gene; moreover, DNA molecules encoding δ-endotoxin genes can be purchased from American Type Culture Collection (Manassas, Va.), for example, under ATCC Accession Nos. 40098; 67136; 31995; and 31998)); a gene that encodes a lectin (See, e.g., Van Damme et al. (1994) *Plant Molec. Biol.* 24:25 (nucleotide sequences of several *Clivia miniata* mannose-binding lectin genes)); a gene that encodes a vitamin-binding protein, e.g., avidin (See PCT International Patent Publication No. US93/06487 (use of avidin and avidin homologues as larvicides against insect pests)); a gene that encodes an enzyme inhibitor, e.g., a protease, proteinase inhibitor, or amylase inhibitor (See, e.g., Abe et al. (1987) J. Biol. Chem. 262:16793 (nucleotide sequence of rice cysteine proteinase inhibitor); Huub et al. (1993) Plant Molec. Biol. 21:985 (nucleotide sequence of cDNA encoding tobacco proteinase inhibitor I); Sumitani et al. (1993) Biosci. Biotech. Biochem. 57:1243 (nucleotide sequence of *Streptomyces nitrosporeus* alpha-amylase inhibitor) and U.S. Pat. No. 5,494,813); a gene encoding an insect-specific hormone or pheromone, e.g., an ecdysteroid or juvenile hormone, a variant thereof, a mimetic based thereon, or an antagonist or agonist thereof (See, e.g., Hammock et al. (1990) Nature 344:458 (baculovirus expression of cloned juvenile hormone esterase, an inactivator of juvenile hormone)); a gene encoding an insect-specific peptide or neuropeptide that, upon expression, disrupts the physiology of the affected pest (See, e.g., Regan (1994) J. Biol. Chem. 269:9 (expression cloning yields DNA coding for insect diuretic hormone receptor); Pratt et al. (1989) Biochem. Biophys. Res. Comm. 163:1243 (an allostatin in *Diploptera puntata*); and U.S. Pat. No. 5,266,317 (genes encoding insect-specific, paralytic neurotoxins)); a gene encoding an insect-specific venom produced in nature by a snake, a wasp, or other organism (See, e.g., Pang et al. (1992) Gene 116:165 (heterologous expression in plants of a gene coding for a scorpion insectotoxic peptide)); a gene encoding an enzyme responsible for a hyperaccumulation of a monoterpene, a sesquiterpene, a steroid, hydroxamic acid, a phenylpropanoid derivative or other molecule with insecticidal activity; a gene encoding an enzyme involved in the modification, including the post-translational modification, of a biologically active molecule, e.g., a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, or a glucanase, whether natural or synthetic (See, e.g., PCT International Patent Publication No. WO 93/02197 (nucleotide sequence of a callase gene); moreover, DNA molecules containing chitinase-encoding sequences can be obtained, for example, from the ATCC, under Accession Nos. 39637 and 67152; Kramer et al. (1993) Insect Biochem. Molec. Biol. 23:691 (nucleotide sequence of a cDNA encoding tobacco hornworm chitinase); and Kawalleck et al. (1993) Plant Molec. Biol. 21:673 (nucleotide sequence of the parsley ubi4-2 polyubiquitin gene)); a gene encoding a molecule that stimulates signal transduction (See, e.g., Botella et al. (1994) Plant Molec. Biol. 24:757 (nucleotide sequences for mung bean calmodulin cDNA clones); and Griess et al. (1994) Plant Physiol. 104:1467 (nucleotide sequence of a maize calmodulin cDNA clone)); a gene that encodes a hydrophobic moment peptide (See, e.g., PCT International Patent Publication No. WO 95/16776 (peptide derivatives of Tachyplesin which inhibit fungal plant pathogens); and PCT International Patent Publication No. WO 95/18855 (synthetic antimicrobial peptides that confer disease resistance)); a gene that encodes a membrane permease, a channel former, or a channel blocker (See, e.g., Jaynes et al. (1993) Plant Sci 89:43 (heterologous expression of a cecropin-0 lytic peptide analog to render transgenic tobacco plants resistant to *Pseudomonas solanacearum*)); a gene that encodes a viral-invasive protein or complex toxin derived therefrom (See, e.g., Beachy et al. (1990) Ann. rev. Phytopathol. 28:451); a gene that encodes an insect-specific antibody or immunotoxin derived therefrom (See, e.g., Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments)); a gene encoding a virus-specific antibody (See, e.g., Tavladoraki et al. (1993) Nature 366:469 (transgenic plants expressing recombinant antibody genes are protected from virus attack)); a gene encoding a developmental-arrestive protein produced in nature by a pathogen or a parasite (See, e.g., Lamb et al. (1992) Bio/Technology 10:1436 (fungal endo α-1,4-D-polygalacturonases facilitate fungal colonization and plant nutrient release by solubilizing plant cell wall homo-α-1,4-D-galacturonase); Toubart et al. (1992) Plant J. 2:367 (cloning and characterization of a gene which encodes a bean endopolygalacturonase-inhibiting protein)); a gene encoding a developmental-arrestive protein produced in nature by a plant (See, e.g., Logemann et al. (1992) Bio/Technology 10:305 (transgenic plants expressing the barley ribosome-inactivating gene have an increased resistance to fungal disease)).

In some embodiments, nucleic acids comprising an agronomic gene or nucleotide sequence encoding a polypeptide of interest may also and/or alternatively include, for example and without limitation: genes that confer resistance to an herbicide, such as an herbicide that inhibits the growing point or meristem, for example, an imidazolinone or a sulfonylurea (exemplary genes in this category encode mutant ALS and AHAS enzymes, as described, for example, by Lee et al. (1988) EMBO J. 7:1241, and Miki et al. (1990) Theor. Appl. Genet. 80:449, respectively); glyphosate resistance as conferred by, e.g., mutant 5-enolpyruvylshikimate-3-phosphate synthase (EPSPs) genes (via the introduction of recombinant nucleic acids and/or various forms of in vivo mutagenesis of native EPSPs genes (including but not limited to CP4, DMMG, and DGT-28); aroA genes and glyphosate acetyl transferase (GAT) genes, respectively); other phosphono compounds, such as glufosinate phosphinothricin acetyl transferase (PAT) genes from *Streptomyces* species, including *Streptomyces hygroscopicus* and *Streptomyces viridichromogenes*); and pyridinoxy or phenoxy proprionic acids and cyclohexones (ACCase inhibitor-encoding genes). See, e.g., U.S. Pat. Nos. 4,940,835 and 6,248,876 (nucleotide sequences of forms of EPSPs which can confer glyphosate resistance to a plant). A DNA molecule encoding a mutant aroA gene can be obtained under ATCC accession number 39256. See also U.S. Pat. No. 4,769,061 (nucleotide sequence of a mutant aroA gene). European Patent Publication No. 0333033A1 and U.S. Pat. No. 4,975,374 disclose nucleotide sequences of glutamine synthetase genes, which may confer resistance to herbicides such as L-phosphinothricin. Nucleotide sequences of exemplary PAT genes are provided in U.S. Pat. No. 5,561,236, and DeGreef et al. (1989) Bio/Technology 7:61 (production of transgenic plants that express chimeric bar genes coding for PAT activity). Exemplary of genes conferring resistance to phenoxy proprionic acids and cyclohexones, such as sethoxydim and haloxyfop, include the Accl-S1, Accl-S2 and Accl-S3 genes described by Marshall et al. (1992) Theor. Appl. Genet. 83:435. GAT genes capable of conferring glyphosate resistance are described, for example, in WO 2005012515. Genes conferring resistance to 2,4-D, phenoxyproprionic acid and pyridyloxy auxin herbicides are described, for example, in WO 2005107437 and WO 2007053482.

Nucleic acids comprising an agronomic gene or nucleotide sequence encoding a polypeptide of interest may also include, for example and without limitation: a gene conferring resistance to an herbicide that inhibits photosynthesis, such as a triazine (psbA and gs+ genes) or a benzonitrile (nitrilase gene). See, e.g., Przibila et al. (1991) Plant Cell 3:169 (transformation of *Chlamydomonas* with plasmids encoding mutant psbA genes). Nucleotide sequences for nitrilase genes are disclosed in U.S. Pat. No. 4,810,648, and DNA molecules containing these genes are available under ATCC Accession Nos. 53435; 67441; and 67442. See also Hayes et al. (1992) Biochem. J. 285:173 (cloning and expression of DNA coding for a glutathione S-transferase).

In some embodiments, nucleic acids comprising an agronomic gene or nucleotide sequence encoding a polypeptide of interest may also and/or alternatively include, genes that confer or contribute to a value-added trait, for example and without limitation: modified fatty acid metabolism, e.g., by transforming a plant with an antisense gene of stearyl-ACP desaturase to increase stearic acid content of the plant (See, e.g., Knultzon et al. (1992) Proc. Natl. Acad. Sci. U.S.A. 89:2624); decreased phytate content, e.g., introduction of a phytase-encoding gene may enhance breakdown of phytate, adding more free phosphate to the transformed plant (See, e.g., Van Hartingsveldt et al. (1993) Gene 127:87 (nucleotide sequence of an *Aspergillus niger* phytase gene); a gene may be introduced to reduce phytate content—in maize, for example, this may be accomplished by cloning and then reintroducing DNA associated with the single allele which may be responsible for maize mutants characterized by low levels of phytic acid (See Raboy et al. (1990) Maydica 35:383)); and modified carbohydrate composition effected, e.g., by transforming plants with a gene encoding an enzyme that alters the branching pattern of starch (See, e.g., Shiroza et al. (1988) J. Bacteol. 170:810 (nucleotide sequence of *Streptococcus* mutant fructosyltransferase gene); Steinmetz et al. (1985) Mol. Gen. Genet. 20:220 (levansucrase gene); Pen et al. (1992) Bio/Technology 10:292 (α-amylase); Elliot et al. (1993) Plant Molec. Biol. 21:515 (nucleotide sequences of tomato invertase genes); Sogaard et al. (1993) J. Biol. Chem. 268:22480 (barley α-amylase gene); and Fisher et al. (1993) Plant Physiol. 102:1045 (maize endosperm starch branching enzyme II)).

In some embodiments, an exogenous nucleic acid is integrated at a FAD2 locus, so as to modify the FAD2 locus, wherein the nucleic acid comprises a PTU or ELP, such that, for example, the subsequent site-specific integration of a second exogenous nucleic acid at the site of the PTU or ELP is facilitated. See, also, U.S. Patent Publication No. 20130326645.

Targeting endonuclease-mediated integration of a nucleic acid molecule of interest into a plant genome via targeted integration requires delivery of targeting endonucleases or targeting endonuclease-encoding nucleic acid molecules, followed by expression of a functional targeting endonuclease protein in the host. An exogenous nucleic acid is preferably also be present in the host cell at the same time as the targeting endonuclease is delivered or expressed therein, such that functional targeting endonuclease protein induces double-stranded breaks at the target site(s) in the at least one FAD2 locus, which are then repaired, for example via homology-driven integration of the exogenous nucleic acid into the locus. One skilled in the art may envision that expression of a functional targeting endonuclease protein may be achieved by several methods, including, but not limited to, transgenesis of a targeting endonuclease-encoding construct, and transient expression of a targeting endonuclease-encoding construct. In both these cases, expression of a functional targeting endonuclease protein and delivery of an exogenous nucleic acid in the host cell may be simultaneously achieved in order to drive targeted integration at a FAD2 locus.

A particular advantage obtained in embodiments utilizing ZFNs as targeting endonucleases, is that the requirement for dimerization of cleavage domains of chimeric zinc finger nucleases imparts a high level of sequence, and hence cleavage, specificity. Since each set of three fingers binds nine consecutive base pairs, two chimeric nucleases effectively demand an 18 bp target if each zinc finger domain has perfect specificity. Any given sequence of this length is predicted to be unique within a single genome (assuming approximately $10^9$ bp). Bibikova et al. (2001) Mol. Cell. Biol. 21(1):289-97; Wu et al. (2007), supra. Furthermore, additional fingers can provide enhanced specificity, Beerli et al. (1998) Proc. Natl. Acad. Sci. USA 95:14628-33; Kim and Pabo (1998) Proc. Natl. Acad. Sci. USA 95:2812-7; Liu et al. (1997) Proc. Natl. Acad. Sci. USA 94:5525-30, so the number of zinc fingers in each DNA-binding domain may be increased to provide even further specificity. For example, specificity may be further increased by using a pair of 4-, 5-, 6- or more finger ZFNs that recognize a 24 bp sequence. Urnov et al. (2005) Nature 435:646-51. Thus, ZFNs may be used such that a recognition sequence is introduced into the host plant genome is unique within the genome.

B. Nucleic Acid Molecules Comprising a Nucleotide Sequence Encoding a Targeting Endonuclease In some embodiments, a nucleotide sequence encoding a targeting endonuclease may be engineered by manipulation (e.g., ligation) of native nucleotide sequences encoding polypeptides comprised within the targeting endonuclease. For example, the nucleotide sequence of a gene encoding a protein comprising a DNA-binding polypeptide may be inspected to identify the nucleotide sequence of the gene that corresponds to the DNA-binding polypeptide, and that nucleotide sequence may be used as an element of a nucleotide sequence encoding a targeting endonuclease comprising the DNA-binding polypeptide. Alternatively, the amino acid sequence of a targeting endonuclease may be used to deduce a nucleotide sequence encoding the targeting endonuclease, for example, according to the degeneracy of the genetic code.

In exemplary nucleic acid molecules comprising a nucleotide sequence encoding a targeting endonuclease, the last codon of a first polynucleotide sequence encoding a nuclease polypeptide, and the first codon of a second polynucleotide sequence encoding a DNA-binding polypeptide, may be separated by any number of nucleotide triplets, e.g., without coding for an intron or a "STOP." Likewise, the last codon of a nucleotide sequence encoding a first polynucleotide sequence encoding a DNA-binding polypeptide, and the first codon of a second polynucleotide sequence encoding a nuclease polypeptide, may be separated by any number of nucleotide triplets. In these and further embodiments, the last codon of the last (i.e., most 3' in the nucleic acid sequence) of a first polynucleotide sequence encoding a nuclease polypeptide, and a second polynucleotide sequence encoding a DNA-binding polypeptide, may be fused in phase-register with the first codon of a further polynucleotide coding sequence directly contiguous thereto, or separated therefrom by no more than a short peptide sequence, such as that encoded by a synthetic nucleotide linker (e.g., a nucleotide linker that may have been used to achieve the fusion). Examples of such further polynucleotide sequences include, for example and without limitation, tags, targeting peptides, and enzymatic cleavage sites. Likewise, the first codon of the most 5' (in the nucleic acid sequence) of the first and second polynucleotide sequences may be fused in phase-register with the last codon of a further polynucleotide coding sequence directly contiguous thereto, or separated therefrom by no more than a short peptide sequence.

A sequence separating polynucleotide sequences encoding functional polypeptides in a targeting endonuclease (e.g., a DNA-binding polypeptide and a nuclease polypeptide) may, for example, consist of any sequence, such that the amino acid sequence encoded is not likely to significantly alter the translation of the targeting endonuclease. Due to the autonomous nature of known nuclease polypeptides and known DNA-binding polypeptides, intervening sequences will not in examples interfere with the respective functions of these structures.

C. Vectors and Expression Constructs

In some embodiments, at least one nucleic acid molecule(s) comprising at least one exogenous polynucleotide sequence encoding a polypeptide of interest, and/or a targeting endonuclease, may be introduced into a cell, tissue, or organism for expression therein. For example, a nucleic acid molecule comprising a polynucleotide sequence encoding a targeting endonuclease that specifically recognizes a nucleotide sequence comprised within at least one FAD2 locus may be introduced into a cell for expression of the targeting endonuclease, and a nucleic acid molecule comprising a polynucleotide sequence encoding a polypeptide of interest may be introduced into the cell, such that the polynucleotide sequence encoding the polypeptide of interest is integrated into the at least one FAD2 locus, e.g., by homologous recombination following introduction of a double strand break at the locus by the expressed targeting endonuclease, and the polypeptide of interest is expressed from the integrated polynucleotide sequence.

In some embodiments, a nucleic acid molecule such as one of the foregoing may, for example, be a vector system including, for example and without limitation, a linear plasmid, or a closed circular plasmid. In particular examples, the vector may be an expression vector. Nucleic acid sequences according to particular embodiments may, for example, be integrated into a vector, such that the nucleic acid sequence is operably linked to one or more regulatory sequences. Many vectors are available for this purpose, and selection of the particular vector may depend, for example, on the size of the nucleic acid to be inserted into the vector, the particular host cell to be transformed with the vector, and/or the amount of any encoded polypeptide that is desired to be expressed. A vector typically contains various components, the identity of which depend on a function of the vector (e.g., amplification of DNA or expression of DNA), and the particular host cell(s) with which the vector is compatible.

In some embodiments, a regulatory sequence operably linked to one or more coding sequence(s) may be a promoter sequence that functions in a host cell, such as a bacterial cell, algal cell, fungal cell, or plant cell, wherein the nucleic acid molecule is to be amplified or expressed. Some embodiments may include a plant transformation vector that comprises a nucleotide sequence comprising at least one regulatory sequence operably linked to one or more nucleotide sequence(s) encoding a polypeptide of interest or a targeting endonuclease, wherein the one or more nucleotide sequence(s) may be expressed, under the control of the regulatory sequence(s), in a plant cell, tissue, or organism to produce the polypeptide of interest or the targeting endonuclease.

Promoters suitable for use in nucleic acid molecules according to some embodiments include those that are inducible, tissue-specific, viral, synthetic, or constitutive, all of which are well known in the art. Non-limiting examples of promoters that may be useful in embodiments of the invention are provided by: U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (35S promoter); U.S. Pat. No. 6,433,252 (maize L3 oleosin promoter); U.S. Pat. No. 6,429,357 (rice actin 2 promoter, and rice actin 2 intron); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); U.S. Pat. No. 5,447,858 (soybean heat shock promoter); and U.S. Pat. No. 7,151,204 (maize chloroplast aldolase promoter).

Additional exemplary promoters include the nopaline synthase (NOS) promoter (Ebert et al. (1987) Proc. Natl. Acad. Sci. USA 84(16):5745-9); the octopine synthase (OCS) promoter (which is carried on tumor-inducing plasmids of *Agrobacterium tumefaciens*); the caulimovirus promoters such as the cauliflower mosaic virus (CaMV) 19S promoter (Lawton et al. (1987) Plant Mol. Biol. 9:315-24); the CaMV 35S promoter (Odell et al. (1985) Nature 313: 810-2; the figwort mosaic virus 35S-promoter (Walker et al. (1987) Proc. Natl. Acad. Sci. USA 84(19):6624-8); the sucrose synthase promoter (Yang and Russell (1990) Proc. Natl. Acad. Sci. USA 87:4144-8); the R gene complex promoter (Chandler et al. (1989) Plant Cell 1:1175-83); the chlorophyll a/b binding protein gene promoter; CaMV35S (U.S. Pat. Nos. 5,322,938, 5,352,605, 5,359,142, and 5,530, 196); FMV35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank Accession No. V00087; Depicker et al. (1982) J. Mol. Appl. Genet. 1:561-73; Bevan et al. (1983) Nature 304:184-7).

In particular embodiments, nucleic acid molecules may comprise a tissue-specific promoter. A tissue-specific promoter is a nucleotide sequence that directs a higher level of transcription of an operably linked nucleotide sequence in the tissue for which the promoter is specific, relative to the other tissues of the organism. Examples of tissue-specific promoters include, without limitation: tapetum-specific promoters; anther-specific promoters; pollen-specific promoters (See, e.g., U.S. Pat. No. 7,141,424, and International PCT Publication No. WO 99/042587); ovule-specific promoters; (See, e.g., U.S. Patent Publication No. 2001/047525 A1); fruit-specific promoters (See, e.g., U.S. Pat. Nos. 4,943,674, and 5,753,475); and seed-specific promoters (See, e.g., U.S. Pat. Nos. 5,420,034, and 5,608,152). In some embodiments, a developmental stage-specific promoter (e.g., a promoter active at a later stage in development) may be used.

Additional regulatory sequences that may in some embodiments be operably linked to a nucleic acid molecule include 5' UTRs located between a promoter sequence and a coding sequence that function as a translation leader sequence. The translation leader sequence is present in the fully-processed mRNA, and it may affect processing of the primary transcript, and/or RNA stability. Examples of translation leader sequences include maize and *petunia* heat shock protein leaders (U.S. Pat. No. 5,362,865), plant virus coat protein leaders, plant rubisco leaders, and others. See, e.g., Turner and Foster (1995) Molecular Biotech. 3(3):225-36. Non-limiting examples of 5' UTRs are provided by: GmHsp (U.S. Pat. No. 5,659,122); PhDnaK (U.S. Pat. No. 5,362,865); AtAntl; TEV (Carrington and Freed (1990) J.

Virol. 64:1590-7); and AGRtunos (GenBank Accession No. V00087; and Bevan et al. (1983), supra).

Additional regulatory sequences that may in some embodiments be operably linked to a nucleic acid molecule also include 3' non-translated sequences, 3' transcription termination regions, or poly-adenylation regions. These are genetic elements located downstream of a nucleotide sequence, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation sequence can be derived from a variety of plant genes, or from T-DNA genes. A non-limiting example of a 3' transcription termination region is the nopaline synthase 3' region (nos 3'; Fraley et al. (1983) Proc. Natl. Acad. Sci. USA 80:4803-7). An example of the use of different 3' nontranslated regions is provided in Ingelbrecht et al. (1989) Plant Cell 1:671-80. Non-limiting examples of polyadenylation signals include one from a *Pisum sativum* RbcS2 gene (Ps.RbcS2-E9; Coruzzi et al. (1984) EMBO J. 3:1671-9) and AGRtu.nos (GenBank Accession No. E01312).

Additional information regarding regulatory sequences that may be useful in particular embodiments is described, for example, in Goeddel (1990) "Gene Expression Technology," Methods Enzymol. 185, Academic Press, San Diego, Calif.

A recombinant nucleic acid molecule or vector may comprise a selectable marker that confers a selectable phenotype on a transformed cell, such as a plant cell. Selectable markers may also be used to select for cells or organisms that comprise a nucleic acid molecule comprising the selectable marker. A marker may encode biocide resistance, antibiotic resistance (e.g., kanamycin, Geneticin (G418), bleomycin, and hygromycin), or herbicide resistance (e.g., glyphosate). Examples of selectable markers include, but are not limited to: a neo gene that confers kanamycin resistance and can be selected for using, e.g., kanamycin and G418; a bar gene that confers bialaphos resistance; a mutant EPSP synthase gene that confers glyphosate resistance; a nitrilase gene that confers resistance to bromoxynil; a mutant acetolactate synthase gene (ALS) that confers imidazolinone or sulfonylurea resistance; and a methotrexate-resistant DHFR gene. Multiple selectable markers are available that confer resistance to chemical agents including, for example and without limitation, ampicillin; bleomycin; chloramphenicol; gentamycin; hygromycin; kanamycin; lincomycin; methotrexate; phosphinothricin; puromycin; spectinomycin; rifampicin; streptomycin; and tetracycline. Examples of such selectable markers are illustrated in, e.g., U.S. Pat. Nos. 5,550,318; 5,633,435; 5,780,708 and 6,118,047.

A nucleic acid molecule or vector may also or alternatively include a screenable marker. Screenable markers may be used to monitor expression. Exemplary screenable markers include a (3-glucuronidase or uidA gene (GUS) which encodes an enzyme for which various chromogenic substrates are known (Jefferson et al. (1987) Plant Mol. Biol. Rep. 5:387-405); an R-locus gene, which encodes a product that regulates the production of anthocyanin pigments (red color) in plant tissues (Dellaporta et al. (1988) "Molecular cloning of the maize R-nj allele by transposon tagging with Ac." In 18*th Stadler Genetics Symposium*, P. Gustafson and R. Appels, eds., Plenum, NY (pp. 263-82); a β-lactamase gene (Sutcliffe et al. (1978) Proc. Natl. Acad. Sci. USA 75:3737-41); a gene which encodes an enzyme for which various chromogenic substrates are known (e.g., PADAC, a chromogenic cephalosporin); a luciferase gene (Ow et al. (1986) Science 234:856-9); a xylE gene that encodes a catechol dioxygenase that converts chromogenic catechols (Zukowski et al. (1983) Gene 46(2-3):247-55); an amylase gene (Ikatu et al. (1990) Bio/Technol. 8:241-2); a tyrosinase gene which encodes an enzyme capable of oxidizing tyrosine to DOPA and dopaquinone, which in turn condenses to melanin (Katz et al. (1983) J. Gen. Microbiol. 129:2703-14); and an α-galactosidase.

All of the nucleotide sequences that encode, for example, a particular polypeptide of interest or a particular targeting endonuclease, will be immediately recognizable by those of skill in the art. The degeneracy of the genetic code provides a finite number of coding sequences for a particular amino acid sequence. The selection of a particular sequence to encode a polypeptide according to embodiments of the invention is within the discretion of the practitioner. Different coding sequences may be desirable in different applications.

In some embodiments, it may be desirable to modify the nucleotides of a nucleic acid, for example, to enhance expression of a polynucleotide sequence comprised within the nucleic acid in a particular host. The genetic code is redundant with 64 possible codons, but most organisms preferentially use a subset of these codons. The codons that are utilized most often in a species are called optimal codons, and those not utilized very often are classified as rare or low-usage codons. Zhang et al. (1991) Gene 105: 61-72. Codons may be substituted to reflect the preferred codon usage of a particular host in a process sometimes referred to as "codon optimization." Optimized coding sequences containing codons preferred by a particular prokaryotic or eukaryotic host may be prepared, for example, to increase the rate of translation or to produce recombinant RNA transcripts having desirable properties (e.g., a longer half-life, as compared with transcripts produced from a non-optimized sequence).

Nucleic acids may be introduced into a host cell in embodiments of the invention by any method known to those of skill in the art, including, for example and without limitation: by transformation of protoplasts (See, e.g., U.S. Pat. No. 5,508,184); by desiccation/inhibition-mediated DNA uptake (See, e.g., Potrykus et al. (1985) Mol. Gen. Genet. 199:183-8); by electroporation (See, e.g., U.S. Pat. No. 5,384,253); by agitation with silicon carbide fibers (See, e.g., U.S. Pat. Nos. 5,302,523 and 5,464,765); by *Agrobacterium*-mediated transformation (See, e.g., U.S. Pat. Nos. 5,563,055, 5,591,616, 5,693,512, 5,824,877, 5,981,840, and 6,384,301); and by acceleration of DNA-coated particles (See, e.g., U.S. Pat. Nos. 5,015,580, 5,550,318, 5,538,880, 6,160,208, 6,399,861, and 6,403,865). Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more nucleic acid sequences of the invention in the genome of the transgenic plant.

The most widely-utilized method for introducing an expression vector into plants is based on the natural transformation system of *Agrobacterium*. *A. tumefaciens* and *A. rhizogenes* are plant pathogenic soil bacteria that genetically transform plant cells. The $T_i$ and $R_i$ plasmids of *A. tumefaciens* and *A. rhizogenes*, respectively, carry genes responsible for genetic transformation of the plant. The $T_i$ (tumor-inducing)-plasmids contain a large segment, known as T-DNA, which is transferred to transformed plants. Another segment of the T$_i$ plasmid, the vir region, is responsible for T-DNA transfer. The T-DNA region is bordered by left-hand and right-hand borders that are each composed of terminal repeated nucleotide sequences. In some modified binary vectors, the tumor-inducing genes have been deleted, and the functions of the vir region are utilized to transfer foreign DNA bordered by the T-DNA border sequences. The T-region may also contain, for example, a selectable marker for efficient recovery of transgenic plants and cells, and a multiple cloning site for inserting sequences for transfer such as a nucleic acid encoding a fusion protein of the invention.

Thus, in some embodiments, a plant transformation vector is derived from a T$_i$ plasmid of *A. tumefaciens* (See, e.g., U.S. Pat. Nos. 4,536,475, 4,693,977, 4,886,937, and 5,501,967; and European Patent EP 0 122 791) or a R$_i$ plasmid of *A. rhizogenes*. Additional plant transformation vectors include, for example and without limitation, those described by Herrera-Estrella et al. (1983) Nature 303:209-13; Bevan et al. (1983), supra; Klee et al. (1985) Bio/Technol. 3:637-42; and in European Patent EP 0 120 516, and those derived from any of the foregoing. Other bacteria, such as *Sinorhizobium*, *Rhizobium*, and *Mesorhizobium*, that naturally interact with plants can be modified to mediate gene transfer to a number of diverse plants. These plant-associated symbiotic bacteria can be made competent for gene transfer by acquisition of both a disarmed T$_i$ plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a nucleic acid molecule of interest (for example, a nucleotide sequence encoding a polypeptide comprising at least one fusion protein of the invention) in a regenerating plant, a variety of assays may be performed. Such assays include, for example: molecular biological assays, such as Southern and Northern blotting, PCR, and nucleic acid sequencing; biochemical assays, such as detecting the presence of a protein product, e.g., by immunological means (ELISA and/or Western blots) or by enzymatic function; plant part assays, such as leaf or root assays; and analysis of the phenotype of the whole regenerated plant.

Integration events may be analyzed, for example, by PCR amplification using, e.g., oligonucleotide primers that are specific for a nucleotide sequence of interest. PCR genotyping is understood to include, but not be limited to, polymerase-chain reaction (PCR) amplification of genomic DNA derived from isolated host plant tissue predicted to contain a nucleic acid molecule of interest integrated into the genome, followed by standard cloning and sequence analysis of PCR amplification products. Methods of PCR genotyping have been well described (see, e.g., Rios, G. et a. (2002) Plant J. 32:243-53), and may be applied to genomic DNA derived from any plant species or tissue type, including cell cultures.

A transgenic plant formed using *Agrobacterium*-dependent transformation methods typically contains a single to multiple copies of recombinant DNA. The single recombinant DNA sequence is referred to as a "transgenic event" or "integration event." Such transgenic plants are heterozygous for the inserted DNA sequence. In some embodiments, a transgenic plant homozygous with respect to a transgene may be obtained by sexually mating (selfing) an independent segregant transgenic plant that contains a single exogenous gene sequence to itself, for example, an F$_0$ plant, to produce F$_1$ seed. One fourth of the F$_1$ seed produced will be homozygous with respect to the transgene. Germinating F$_1$ seed results in plants that can be tested for heterozygosity, typically using a SNP assay or a thermal amplification assay that allows for the distinction between heterozygotes and homozygotes (i.e., a zygosity assay).

In addition to direct transformation of a plant or plant cell with a nucleic acid molecule in some embodiments, transgenic plants may be prepared in particular embodiments by crossing a first plant having at least one transgenic event with a second plant lacking such an event. For example, a nucleic acid comprising at least one modified FAD2 locus, wherein an exogenous nucleic acid has been integrated in a site-specific manner, may be introduced into a first plant line that is amenable to transformation, to produce a transgenic plant, which transgenic plant may be crossed with a second plant line to introgress the at least one modified FAD2 locus (and therefore the exogenous nucleic acid) into the second plant line.

To confirm the presence of a nucleic acid molecule of interest in regenerating plants, a variety of assays may be performed. Such assays include, for example: molecular biological assays, such as Southern and Northern blotting and PCR; biochemical assays, such as detecting the presence of a protein product, e.g., by immunological means (ELISA and/or Western blots) or by enzymatic function; plant part assays, such as leaf or root assays; and analysis of the phenotype of the whole regenerated plant.

Targeted integration events may be screened, for example, by PCR amplification using, e.g., oligonucleotide primers specific for nucleic acid molecules of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (for example, Rios, G. et al. (2002) Plant J. 32:243-53) and may be applied to genomic DNA derived from any plant species or tissue type, including cell cultures. Combinations of oligonucleotide primers that bind to both target sequence and introduced sequence may be used sequentially or multiplexed in PCR amplification reactions. Oligonucleotide primers designed to anneal to the target site, introduced nucleic acid sequences, and/or combinations of the two are feasible. Thus, PCR genotyping strategies may include (but are not limited to) amplification of specific sequences in the plant genome, amplification of multiple specific sequences in the plant genome, amplification of non-specific sequences in the plant genome, or combinations thereof. One skilled in the art may devise additional combinations of primers and amplification reactions to interrogate the genome. For example, a set of forward and reverse oligonucleotide primers may be designed to anneal to nucleic acid sequence(s) specific for the target outside the boundaries of the introduced nucleic acid sequence.

Forward and reverse oligonucleotide primers may be designed to anneal specifically to an introduced nucleic acid molecule of interest, for example, at a sequence corresponding to a coding region within the nucleic acid molecule of interest, or other parts of the nucleic acid molecule of interest. These primers may be used in conjunction with the primers described above. Oligonucleotide primers may be synthesized according to a desired sequence, and are commercially available (e.g., from Integrated DNA Technologies, Inc., Coralville, Iowa). Amplification may be followed by cloning and sequencing, or by direct sequence analysis of amplification products. One skilled in the art might envision alternative methods for analysis of amplification products generated during PCR genotyping. In one embodiment, oligonucleotide primers specific for the gene target are employed in PCR amplifications.

VI. Transgenic Plants and Plant Materials Comprising a Nucleic Acid Integrated at a FAD2 Performance Locus In some embodiments, a transgenic plant is provided, wherein the plant comprises a plant cell comprising at least one modified (e.g., disrupted and/or targeted integration of an exogenous sequence) FAD2 locus (e.g., soy FAD2 2.3 locus and/or FAD2 2.6 locus). In particular embodiments, such a plant may be produced by transformation of a plant tissue or plant cell, and regeneration of a whole plant. In further embodiments, such a plant may be obtained through introduction of an exogenous nucleic acid at the at least one FAD2 locus in a site-specific manner, or through introgression of the modified FAD2 locus into a germplasm. Plant materials comprising such a plant cell are also provided. Such a plant material may be obtained from a plant comprising the plant cell.

A transgenic plant or plant material comprising a plant cell comprising at least one modified FAD2 locus may in some embodiments exhibit one or more of the following characteristics: expression of a targeting endonuclease in a cell of the plant; expression of a polypeptide of interest in a cell of the plant (or in a plastid therein); expression of a targeting endonuclease in the nucleus of a cell of the plant; localization of a targeting endonuclease in a cell of the plant; integration at a FAD2 locus in the genome of a cell of the plant; integration of a nucleotide sequence encoding a polypeptide of interest or an agronomic gene at a FAD2 locus in the genome of a cell of the plant; and/or the presence of an RNA transcript corresponding to a coding sequence integrated at a FAD2 locus in the genome of a cell of the plant. Such a plant may additionally have one or more desirable traits, including, for example and without limitation, those resulting from the expression of an endogenous or transgenic nucleotide sequence, the expression of which is regulated by a polypeptide of interest or an agronomic gene integrated at a FAD2 locus in the genome of a cell of the plant; resistance to insects, other pests, and disease-causing agents; tolerances to herbicides; enhanced stability, yield, or shelf-life; environmental tolerances; pharmaceutical production; industrial product production; and nutritional enhancements.

A transgenic plant according to the invention may be any plant capable of being transformed with a nucleic acid that is subsequently integrated in at least one FAD2 locus according to methods described herein. Accordingly, the plant may be a dicot or monocot. Non-limiting examples of dicotyledonous plants usable in the present methods include *Arabidopsis*, alfalfa, beans, broccoli, cabbage, canola, carrot, cauliflower, celery, Chinese cabbage, cotton, cucumber, eggplant, lettuce, melon, pea, pepper, peanut, potato, pumpkin, radish, rapeseed, spinach, soybean, squash, sugarbeet, sunflower, tobacco, tomato, and watermelon. Non-limiting examples of monocotyledonous plants usable in the present methods include corn, barley, onion, rice, sorghum, wheat, rye, millet, sugarcane, oat, triticale, switchgrass, and turfgrass. Transgenic plants according to the invention may be used or cultivated in any manner.

Some embodiments also provide commodity products produced from transgenic plants of the invention. Commodity products include, for example and without limitation: food products, meals, oils, or crushed or whole grains or seeds of a plant comprising one or more nucleotide sequences integrated in at least one FAD2 locus. The detection of one or more such nucleotide sequences in one or more commodity or commodity products is de facto evidence that the commodity or commodity product was at least in part produced from a transgenic plant produced according to an embodiment of the invention. In some embodiments, a transgenic plant or seed comprising a plant cell comprising at least one modified FAD2 locus may comprise at least one other transgenic event in its genome, including without limitation: a transgenic event from which is transcribed an RNAi molecule; a gene encoding an insecticidal protein (e.g., a *Bacillus thuringiensis* insecticidal protein); an herbicide tolerance gene (e.g., a gene providing tolerance to glyphosate); and a gene contributing to a desirable phenotype in the transgenic plant (e.g., increased yield, altered fatty acid metabolism, or restoration of cytoplasmic male sterility).

A transgenic plant comprising a plant cell comprising at least one modified FAD2 locus may have one or more desirable traits. Such traits can include, for example: resistance to insects, other pests, and disease-causing agents; tolerances to herbicides; enhanced stability, yield, or shelf-life; environmental tolerances; pharmaceutical production; industrial product production; and nutritional enhancements. The desirable traits may be conferred by one or more nucleic acid molecules integrated by targeted recombination at the FAD2 locus that are expressed in the plant exhibiting the desirable traits. Thus, in some embodiments, the desired trait can be due to the presence of a transgene(s) in the plant, which is introduced into the genome of the plant at the site of at least one modified FAD2 locus. In an additional embodiment, the desirable trait can be obtained through conventional breeding, which trait may be conferred by one or more nucleic acid molecules integrated by targeted recombination at the at least one modified FAD2 locus.

Transgenic plants according to the invention may be used or cultivated in any manner, wherein presence of at least one modified FAD2 locus is desirable. Accordingly, a plant may be engineered to, inter alia, have one or more desired traits, by being transformed with nucleic acid molecules that are subsequently integrated in a site-specific manner in at least one FAD2 locus according to the invention, and cropped and cultivated by any method known to those of skill in the art.

VII. Marker-Assisted Breeding of Transgenic Plants Comprising a Nucleic Acid Integrated at a FAD2 Performance Locus Molecular markers that are linked (e.g., tightly-linked) to fad2 in *Glycine max* are provided. For example, DNA segments containing sequences involved in the HO trait (fad2) are identified. These segments are located around and between markers that are linked (e.g., tightly-linked) to the mutant alleles in a genomic linkage group. Thus, nucleic acid molecules comprising a mutant FAD2 gene having an inactivating mutation are also provided. The segments identified, and the markers thereof, are included in the present subject matter, in part, by their position in linkage groups in the *Glycine max* genome.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention. The following examples are provided to illustrate certain particular features and/or embodiments. The examples should not be construed to limit the disclosure to the particular features or embodiments exemplified.

EXAMPLES

Example 1: Sequencing of FAD2 Target Sequences from Five Soybean Culivars

Sequencing Reactions

Genomic DNA was isolated from soybean tissues. The genomic DNA was isolated and purified from lyophilized embryogenic suspension cells for cultivars X5 and Westag and from young leaves for cultivars Jack, Williams 82 and Maverick. The genomic DNA was extracted using a DNeasy Plant Mini Kit™ (Qiagen; Carlsbad, Calif.) per the manufacturer's protocols.

FAD2 2.3 and 2.6 Genes

The FAD2 2.3 and FAD2 2.6 genomic DNA sequences were amplified by PCR using primers MA49 (SEQ ID NO:1 caagggttccaaacacaaagcc) and MA51 (SEQ ID NO:2 catcaatacttgttcctgtacc) or MA50 (SEQ ID NO:3 gaagaagcctctctcaagggttc) and MA51. Genomic DNA sequence was obtained for a fragment of approximately bases 40 to 1140 of the 1140 bp gene. PCR reaction conditions were of 1 min at 98° C. for the initial denaturation, then 35 cycles of 30 s at 98° C., 15 s at 60° C., 3 min at 72° C. and a final extension for 5 min at 72° C.

The resulting PCR amplicons were suspended in TE buffer (1 μg in TE buffer), and were sheared to fragments of about 300 bp with the Covaris E220 System™ sonicator (Covaris; Woburn, Mass.) using the settings: peak incident power 140, duty factor 10%, 200 cycles per burst, and treatment time of 430 seconds. Illumina™ (San Diego, Calif.) paired-end sequencing libraries were prepared using a PrepX DNA library Kit™ (IntegenX; Pleasanton, Calif.) on the Apollo 324™ Automation System™ (IntegenX) following the manufacturer's recommended protocol. Briefly, sheared DNA fragments with 5' or 3' overhangs were converted to 5' phosphorylated blunt end DNA. A single adenine (A) extension was added to the 3' end of the end-repaired DNA fragments followed by ligation to indexed Illumina™ paired-end (PE) adapters. Lastly, adapter-ligated library products were retrieved from the robot and enriched with PCR using Illumina TruSeq PCR™ reagents under thermocycling conditions of 30 s at 98° C. for the initial denaturation, then 10 cycles of 10 s at 98° C., 30 s at 60° C., 30 s at 72° C. and a final extension for 5 min at 72° C. The enriched libraries were normalized to 2 nM and pooled. Pooled libraries were then denatured with sodium hydroxide and diluted to 6 pM in hybridization buffer for loading onto a Miseq flow Cell™ (Illumina; San Diego, Calif.). A 2×150 cycle run with 6 index cycles was carried out on the Miseq™ according to Illumina's recommended protocol.

The resulting sequence reactions produced paired-end reads from Illumina Miseq™ instrument were trimmed for TruSeq adapter Sequences™ (Illumina). Post trimming, the reads were mapped to the soybean reference scaffolds of cultivar Williams 82 using the Burrows Wheeler Aligner (BWA) (Li H. and Durbin R. (2009) Fast and accurate short read alignment with Burrows-Wheeler Transform. Bioinformatics, 25:1754-60).

Each soybean cultivar was treated as a separate sample and so each cultivar's sequencing reads were mapped separately. Regions on the scaffold where the depth of mapped sequencing reads were greater than zero were examined. Since these were sequencing reads from amplicons, only specific regions on the scaffolds were expected to have reads mapped to them. Sequencing reads mapped to soybean chromosomes 10 and 20 across the different samples. For each sample, the consensus sequence was obtained using the Mpileup computer program. These results indicated that the sequencing reads mapped to two paralogous putative FAD genes. The resulting sequence reads were aligned to identify the SNPs/variations between the paralogous putative gene sequences obtained from cultivars X5, Westag, Jack, Williams 82 and Maverick.

The sequence alignment was made via the AlignX® program from the Vector NTI Advance 11.0 computer program (Life Technologies, Carlsbad, Calif.) and is shown in FIG. 1 and FIG. 2. AlignX® uses a modified Clustal W algorithm to generate multiple sequence alignments of either protein or nucleic acid sequences for similarity comparisons and for annotation. As shown in FIG. 1 and FIG. 2, the analysis of the isolated sequences indicated that the respective FAD2 2.3 and FAD2 2.6 sequences shared high levels of sequence similarity.

The FAD2 2.3 gene corresponds to bases 49,417,070 to 49,418,219 on chromosome 10 of the Williams 82 reference genomic sequence (SEQ ID NO:4). Sequences of the genes from the five cultivars (Williams 82, Jack, Maverick, X5 and Westag) were identical from bases 41-1140 (coverage obtained with the primers used). The FAD2 2.6 gene corresponds to bases 34,178,330 to 34,179,475 on chromosome 20 of the Williams 82 reference genomic sequence (SEQ ID NO:9). Sequence differences were identified in the X5 sequence relative to the Williams 82 reference sequence at positions 233 (C>T), 352 (A>G), 633 (C>T), 645 (T>C), 658 (T>C), 894 (A>G). Maverick had the same base changes as X5 at positions 352 and 894.

Example 2: Design of Zinc Finger Binding Domains Specific to FAD2 Genes

Zinc finger proteins directed against DNA sequences encoding various functional sequences of the FAD2 gene locus were designed as previously described. See, e.g., Urnov et al. (2005) Nature 435:646-651. Exemplary target sequence and recognition helices are shown in Table 1 (target sites) and Table 2 (recognition helix regions designs). Zinc Finger Nuclease (ZFN) target sites were designed to bind target sites of FAD2. The FAD2 zinc finger designs were incorporated into zinc finger expression vectors encoding a protein having at least one finger with a CCHC structure. See, U.S. Patent Publication No. 2008/0182332. In particular, the last finger in each protein had a CCHC backbone for the recognition helix. The non-canonical zinc finger-encoding sequences were fused to the nuclease domain of the type IIS restriction enzyme FokII (amino acids 384-579 of the sequence of Wah et al., (1998) Proc. Natl. Acad. Sci. USA 95:10564-10569) via a four amino acid ZC linker and an opaque-2 nuclear localization signal derived from *Zea mays* to form FAD2 zinc-finger nucleases (ZFNs). Both wildtype FokI and eHF-FokI domains (see US Patent Publication No. 20110201055) were constructed ZFNs 1 through 3, while only eHF-FokI domains were used for ZFNs 4 through 7.

Activity of FAD2 2.3 and 2.6 designed ZFNs were tested in a DLSSA assay (see US Patent Publication No. 20110301073) to identify the ZFNs with the highest activity. The cleavage of the relevant FAD2 2.3 and 2.6 sequences cloned into mammalian cells by the ZFNs was assessed (FIG. 3). Activity was compared to a highly active reference ZFN (8266:8196); baseline activity is indicated.

TABLE 1

Target Sites of FAD2 Zinc Fingers

| Plasmid Name | Target FAD2 Gene | SEQ ID NO: | Sequence of ZFN Binding Site | ZFN Monomers for Binding the ZFN Binding Site |
|---|---|---|---|---|
| pDAB115603 | 2.3 | 14 | agccatcgccgccatcactccaac acaggttcccttgac | 37354, 37355 |
| pDAB115600 | 2.3 | 14 | agccatcgccgccatcac tccaac acaggttcccttgac | 37354, 37355 |
| pDAB115605 | 2.3 | 15 | tctaccgtgttgcaaccct gaaagg gttggtttggctgctatg | 37370, 37371 |
| pDAB115601 | 2.3 | 15 | tctaccgtgttgcaaccct gaaagg gttggtttggctgctatg | 37370, 37371 |
| pDAB115606 | 2.3 | 16 | gccttgcctcattacgat tcatc agaatgggactggctgaa | 37374, 37375 |
| pDAB115604 | 2.3 | 17 | ctgtgacttactctctct accgt gttgcaaccctgaaaggg | 37366, 37367 |
| pDAB115607 | 2.6 | 18 | agccatcgccgccaccac tccaac acgggttcccttgac | 37384, 37385 |
| pDAB115602 | 2.6 | 18 | agccatcgccgccaccac tccaac acgggttcccttgac | 37384, 37385 |
| pDAB115609 | 2.6 | 19 | ctgtgacttacttgctct accgt gttgcaactatgaaaggg | 37398, 37399 |
| pDAB115608 | 2.6 | 20 | ttcaatgtctctggc agaccc tatgatggattgct | 37392, 37393 |

TABLE 2

FAD2 zinc finger designs of the ZFN monomers for the ZFN binding site

| ZFP# | F1 | F2 | F3 | F4 | F5 | F6 |
|---|---|---|---|---|---|---|
| 37354 | SEQ ID NO: 24 QSSDLSR | SEQ ID NO: 25 RKDALVA | SEQ ID NO: 26 RSADLTR | SEQ ID NO: 27 RSDDLTR | SEQ ID NO: 28 RSDAMSQ | SEQ ID NO: 29 RNASRTR |
| 37355 | SEQ ID NO: 31 DRSNLSR | SEQ ID NO: 31 HKWLRNQ | SEQ ID NO: 32 DSSDRKK | SEQ ID NO: 33 LRHHLTR | SEQ ID NO: 34 QSGTRKT | NA |
| 37370 | SEQ ID NO: 35 QNAHRKT | SEQ ID NO: 33 LRHHLTR | SEQ ID NO: 36 QSGDLTR | SEQ ID NO: 37 QTSTLSK | SEQ ID NO: 38 TSGSLSR | SEQ ID NO: 39 RSDHLTQ |
| 37371 | SEQ ID NO: 40 RSDVLSE | SEQ ID NO: 41 RSADLSR | SEQ ID NO: 24 QSSDLSR | SEQ ID NO: 42 RTDALRG | SEQ ID NO: 33 LRHHLTR | SEQ ID NO: 43 HRSARKR |

TABLE 2-continued

FAD2 zinc finger designs of the ZFN monomers for the ZFN binding site

| ZFP# | F1 | F2 | F3 | F4 | F5 | F6 |
|---|---|---|---|---|---|---|
| 37374 | SEQ ID NO: 44<br>DRSHLTR | SEQ ID NO: 45<br>QSGNLHV | SEQ ID NO: 46<br>RSDHLSA | SEQ ID NO: 47<br>RSNLLVA | SEQ ID NO: 48<br>QSGALAR | SEQ ID NO: 49<br>DRSALAR |
| 37375 | SEQ ID NO: 50<br>QSSNLAR | SEQ ID NO: 51<br>QSSDLRR | SEQ ID NO: 52<br>RSDTLSE | SEQ ID NO: 53<br>QSGHLSR | SEQ ID NO: 54<br>RSDVLST | SEQ ID NO: 55<br>QNAHRIK |
| 37366 | SEQ ID NO: 56<br>RSDNLSQ | SEQ ID NO: 57<br>ASNDRKK | SEQ ID NO: 58<br>RSDNLST | SEQ ID NO: 59<br>MRQHLLN | SEQ ID NO: 60<br>RSDNLAR | SEQ ID NO: 61<br>QKKDRSY |
| 37367 | SEQ ID NO: 62<br>RSDHLSR | SEQ ID NO: 63<br>DRSNRKT | SEQ ID NO: 64<br>RSDTLSA | SEQ ID NO: 65<br>DKSTRTK | SEQ ID NO: 36<br>QSGDLTR | SEQ ID NO: 66<br>TSGSLTR |
| 37384 | SEQ ID NO: 24<br>QSSDLSR | SEQ ID NO: 25<br>RKDALVA | SEQ ID NO: 26<br>RSADLTR | SEQ ID NO: 27<br>RSDDLTR | SEQ ID NO: 67<br>RSDSLSA | SEQ ID NO: 68<br>RSDALAR |
| 37385 | SEQ ID NO: 30<br>DRSNLSR | SEQ ID NO: 31<br>HKWLRNQ | SEQ ID NO: 32<br>DSSDRKK | SEQ ID NO: 33<br>LRHHLTR | SEQ ID NO: 69<br>RRDILHQ | NA |
| 37398 | SEQ ID NO: 56<br>RSDNLSQ | SEQ ID NO: 57<br>ASNDRKK | SEQ ID NO: 58<br>RSDNLST | SEQ ID NO: 59<br>MRQHLLN | SEQ ID NO: 36<br>QSGDLTR | SEQ ID NO: 70<br>QRTHLKA |
| 37399 | SEQ ID NO: 62<br>RSDHLSR | SEQ ID NO: 63<br>DRSNRKT | SEQ ID NO: 40<br>RSDVLSE | SEQ ID NO: 71<br>ARSTRTN | SEQ ID NO: 36<br>QSGDLTR | SEQ ID NO: 66<br>TSGSLTR |
| 37392 | SEQ ID NO: 72<br>QSGNLAR | SEQ ID NO: 73<br>WRISSLAA | SEQ ID NO: 30<br>DRSNLSR | SEQ ID NO: 74<br>WKESLGA | SEQ ID NO: 75<br>HRKSLSR | NA |
| 37393 | SEQ ID NO: 24<br>QSSDLSR | SEQ ID NO: 76<br>YHWYLKK | SEQ ID NO: 77<br>TSGHLSR | SEQ ID NO: 78<br>TSGNLTR | SEQ ID NO: 79<br>WWTSRAL | NA |

Example 3: Zinc Finger Nuclease and Donor Constructs

ZFN Constructs

Plasmid vectors containing ZFN expression constructs of the exemplary zinc finger nucleases, which were identified using the assay, as described in Example 2, were designed and completed.

Each zinc finger-encoding sequence was fused to a sequence encoding an opaque-2 nuclear localization signal (Maddaloni et a. (1989) Nuc. Acids Res. 17(18):7532), that was positioned upstream of the zinc finger nuclease. Next, the opaque-2 nuclear localization signal::zinc finger nuclease fusion sequence was paired with the complementary opaque-2 nuclear localization signal::zinc finger nuclease fusion sequence. As such, each construct consisted of a single open reading frame comprised of two opaque-2 nuclear localization signal::zinc finger nuclease fusion sequences separated by the 2A sequence from Thosea asigna virus (Mattion et al. (1996) J. Virol. 70:8124-8127). Expression of the fusion proteins was driven by a relatively strong constitutive promoter such as a promoter derived from the Cassava Vein Mosaic Virus (CsVMV) promoter and flanked by the Agrobacterium tumefaciens ORF23 3'UnTranslated Region (AtuORF23 3'UTR).

The vectors were assembled using the IN-FUSION™ Advantage Technology (Clontech, Mountain View, Calif.). Restriction endonucleases were obtained from New England BioLabs (NEB; Ipswich, Mass.) and T4 DNA Ligase (Invitrogen) was used for DNA ligation. Plasmid preparations were performed using NUCLEOSPIN® Plasmid Kit (Macherey-Nagel Inc., Bethlehem, Pa.) or the Plasmid Midi Kit (Qiagen) following the instructions of the suppliers. DNA fragments were isolated using QIAquick Gel Extraction Kit™ (Qiagen) after agarose Tris-acetate gel electrophoresis. Colonies of all assembled plasmids were initially screened by restriction digestion of miniprep DNA. Plasmid DNA of selected clones was sequenced by a commercial sequencing vendor (Eurofins MWG Operon, Huntsville, Ala.). Sequence data were assembled and analyzed using the SEQUENCHER™ software (Gene Codes Corp., Ann Arbor, Mich.).

Before delivery to *Glycine max* protoplasts, Plasmid DNA was prepared from cultures of *E. coli* using the Pure Yield Plasmid Maxiprep System® (Promega Corporation, Madison, Wis.) or Plasmid Maxi Kit® (Qiagen, Valencia, Calif.) following the instructions of the suppliers.

The resulting eleven plasmid constructs; pDAB115603 (containing the ZFN37354 and ZFN37355 construct with eHF-FokI), pDAB115600 (containing the ZFN37354 and ZFN37355 construct with wildtype FokI), pDAB115605 (containing the ZFN37370 and ZFN37371 construct with eHF-FokI), pDAB115601 (containing the ZFN37370 and ZFN37371construct with wildtype FokI), pDAB115606 (containing the ZFN37374 and ZFN37375 construct with eHF-FokI), pDAB115604 (containing the ZFN37366 and ZFN37367 construct with eHF-FokI), pDAB115607 (containing the ZFN37384 and ZFN37385 construct with eHF-FokI), pDAB115602 (containing the ZFN37384 and ZFN37385 construct with wildtype FokI), pDAB115609 (containing the ZFN37398 and ZFN37399 construct with eHF-FokI), and pDAB115608 (containing the ZFN37392 and ZFN37393 construct with eHF-FokI) were confirmed via restriction enzyme digestion and via DNA sequencing.

Donor Constructs

FAD2 donor vectors were constructed by combining synthesized de novo linear pieces within a high copy plasmid vector. pDAB115620 (FIG. 4) and pDAB115622 (FIG. 5) were used for donor integration within the FAD2 loci of the soybean genome. Both of the donor vectors were synthesized to contain zinc finger nuclease binding domains. pDAB115620 ("Donor 1") comprises the 37354:37355 ZFN binding domain, 37366:37367 ZFN binding domain, 37370:37371 ZFN binding domain, and 37374:37375 ZFN binding domain. pDAB115622 ("Donor 2") comprises the 37384:37385 ZFN binding domain, 37392:37393 ZFN binding domain, and the 37398:37399 ZFN binding domain. The ZFN binding domains are recognized by the corresponding expressed zinc finger nuclease and are cleaved during co-transformation in plant cells with the donor vector and the zinc finger nuclease vector.

Example 4: Transformation of Soybean Protoplasts

A soybean (e.g., *Glycine max* c.v. Maverick) protoplast-based transformation method was developed. Protoplasts were isolated from a Maverick suspension culture derived from callus produced from leaf explants. The techniques described below describe the method.
Culture Maintenance
Soybean cell suspensions were subcultured every 7 days by a 1:5 dilution in fresh LS medium (Linsmaier and Skoog 1965) containing 3% (w/v) sucrose, 0.5 mg/L 2,4-D, and 7 g of bactoagar, pH 5.7 All experiments were performed starting 7 days post subculture based on the protocol described below.
Protoplast Isolation
Thirty milliliters of a Maverick suspension culture 7 days post subculturing was transferred to a 50 ml conical centrifuge tube and centrifuged at 200 g for 3 minutes, yielding about 10 ml of settled cell volume (SCV) per tube. The supernatant was removed without disturbing the cell pellet. Twenty milliliters of the enzyme solution (0.3% pectolyase (320952; MP Biomedicals), 3% cellulase ("Onozuka" R10™; Yakult Pharmaceuticals, Japan) in MMG solution (4 mM MES, 0.6 M mannitol, 15 mM $MgCl_2$, pH 6.0) was added for every 4 SCV of suspension cells and the tubes were wrapped with Parafilm™. The tubes were placed on a platform rocker overnight (about 16-18 hr). The next morning, an aliquot of the digested cells was viewed microscopically to ensure the digestion of the cell walls was sufficient.
Protoplast Purification
The cells/enzyme solutions were filtered slowly through a 100 M cell strainer. The cell strainer was rinsed with 10 ml of W5+ media (1.82 mM MES, 192 mM NaCl, 154 mM $CaCl_2$, 4.7 mM KCl, pH 6.0). The filtering step was repeated using a 70 μM screen. The final volume was brought to 40 ml by adding 10 ml of W5+ media. The cells were mixed by inverting the tube. The protoplasts were slowly layered onto 8 ml of a sucrose cushion solution (500 mM sucrose, 1 mM $CaCl_2$, 5 mM MES-KOH, pH 6.0) by adding the cushion solution to the bottom of a 50 ml conical centrifuge tube containing the cells. The tubes were centrifuged at 350 g for 15 minutes in a swinging bucket rotor. A 5 ml pipette tip was used to slowly remove the protoplast band (about 7-8 ml). The protoplasts were then transferred to a 50 ml conical tube and 25 ml of W5+ wash was added. The tubes were inverted slowly and the centrifuged for 10 minutes at 200 g. The supernatant was removed, 10 ml of MMG solution was added and the tube was inverted slowly to resuspend the protoplasts. The protoplast density was determined using a haemocytometer or a flow cytometer. Typically, 4 PCV of cells suspension yielded about 2 million protoplasts.
Transformation of Protoplasts Using PEG
The protoplast concentration was adjusted to 1.6 million/ml with MMG. Protoplast aliquots of 300 μl (about 500,000 protoplasts) were transferred into 2 ml sterile tubes. The protoplast suspension was mixed regularly during the transfer of protoplasts into the tubes. Plasmid DNA was added to the protoplast aliquots according to the experimental design. The rack containing the tubes of protoplasts was slowly inverted 3 times for 1 minute each to mix the DNA and protoplasts. The protoplasts were incubated for 5 minutes at room temperature. Three hundred microliters of a polyethylene glycol (PEG 4000) solution (40% ethylene glycol (81240-Sigma Aldrich), 0.3 M mannitol, 0.4 M $CaCl_2$) was added to the protoplasts and the rack of tubes was mixed for 1 min and incubated for 5 min, with gentle inversion twice during the incubation. One milliliter of W5+ was slowly added to the tubes and the rack of tubes inverted 15-20 times. The tubes were then centrifuged at 350 g for 5 min and the supernatant removed without disturbing the pellet. One milliliter of WI media (4 mM MES 0.6 M mannitol, 20 mM KCl, pH 6.0) was added to each tube and the rack gently inverted to resuspend the pellets. The rack was covered with aluminum foil and laid on its side to incubate overnight at 23° C.
Measuring Transformation Frequency and Harvesting the Protoplasts
Quantification of protoplasts and transformation efficiencies were measured using a Quanta Flow Cytometer™ (Beckman-Coulter Inc). Approximately 16-18 hours post transformation, 100 μl from each replicate was sampled, placed in a 96 well plate and diluted 1:1 with WI solution. The replicates were resuspended 3 times and 100 μl was quantified using flow cytometry. Prior to submitting the samples for analysis, the samples were centrifuged at 200 g for 5 min, supernatants were removed and the samples were flash frozen in liquid nitrogen. The samples were then placed in a −80° C. freezer until processed for molecular analysis.

Example 5: Zinc Finger Nuclease Cleavage and Donor Integration

The designed ZFNs were transformed into soybean protoplasts using the above described transformation methodology. The cleavage efficiency for the FAD2 locus was assessed for the various ZFNs via a locus disruption assay as described in U.S. Patent Publication No. 20140298547. In addition, zinc finger nuclease-mediated integration of a donor sequence within the FAD2 loci was assessed via an in-out PCR assay and the resulting PCR amplicons were sequenced to characterize the donor integration within the soybean genome.

The experiments were comprised of treatment groups containing donor vector alone, ZFN vector alone or ZFN and donor vectors combined (Table 3). In addition, the experiments included negative control treatment groups of untransformed cells or cells transformed with a control vector, pDAB7221 (FIG. 6), comprising a GFP expression cassette driven by the CsVMV promoter and flanked by the AtuORF24 3′-UTR within a high copy number plasmid. The transformed samples were harvested approximately 18-24 hours after transfection. Experimental data demonstrated high activity of ZFN plasmid, pDAB115601 and this ZFN plasmid was used as a positive control in all subsequence experiments.

As detailed in Table 3, the transformation experiments contained a total of 80 μg of DNA, with plasmid pDAB7221 added as necessary to bring the total concentration of DNA to 80 μg. The ratio of donor vector to ZFN-expressing plasmid was approximately 10:1. Each experiment or treatment consisted of six experimental replicates which were processed and analyzed independently. Experiments evaluating the ZFNs were done in two sets of experiments, with the ZFN plasmid, pDAB115601 used in all final experiments as a positive control.

TABLE 3

Experimental design. The ZFN plasmids were evaluated in two sets (F2 ZFNs 1-3 and F2 ZFNs 4-7). Donor vectors appropriate for the ZFN plasmids were tested were used for the targeting experiments. Six replicates were done for each treatment.

| Sample IDs | Donor Plasmid | Amount of Donor Plasmid (μg) | ZFN Plasmid | Amount of ZFN Plasmid (μg) | Amount of pDAB7221 (GFP) |
|---|---|---|---|---|---|
| untreated | — | — | — | — | — |
| GFP control | — | — | — | — | 80 |
| donor 1 alone | pDAB115620 | 36 | — | — | 44 |
| donor 2 alone | pDAB115622 | 36 | — | — | 44 |
| F2 ZFN1_WT alone | — | — | pDAB115600 | 4 | 76 |
| F2 ZFN2_WT alone | — | — | pDAB115601 | 4 | 76 |
| F2 ZFN3_WT alone | — | — | pDAB115602 | 4 | 76 |
| F2 ZFN1_HF alone | — | — | pDAB115603 | 4 | 76 |
| F2 ZFN2_HF alone | — | — | pDAB115605 | 4 | 76 |
| F2 ZFN3_HF alone | — | — | pDAB115607 | — | — |
| donor1 + F2 ZFN1_WT | pDAB115620 | 36 | pDAB115600 | 4 | 40 |
| donor1 + F2 ZFN2_WT | pDAB115620 | 36 | pDAB115601 | 4 | 40 |
| donor2 + F2 ZFN3_WT | pDAB115622 | 36 | pDAB115602 | 4 | 40 |
| donor1 + F2 ZFN1_HF | pDAB115620 | 36 | pDAB115603 | 4 | 40 |
| donor1 + F2 ZFN2_HF | pDAB115620 | 36 | pDAB115605 | 4 | 40 |
| donor2 + F2 ZFN3_HF | pDAB115622 | 36 | pDAB115607 | 4 | 40 |
| untreated | — | — | — | — | — |
| GFP control | — | — | — | — | 80 |
| donor 1 alone | pDAB115620 | 36 | — | — | 44 |
| donor 2 alone | pDAB115622 | 36 | — | — | 44 |
| F2 ZFN2_WT alone | — | — | pDAB115601 | 4 | 76 |
| F2 ZFN4_HF alone | — | — | pDAB115609 | 4 | 76 |
| F2 ZFN5_HF alone | — | — | pDAB115608 | 4 | 76 |
| F2 ZFN6_HF alone | — | — | pDAB115606 | 4 | 76 |
| F2 ZFN7_HF alone | — | — | pDAB115604 | 4 | 76 |
| donor1 + F2 ZFN2_WT | pDAB115620 | 36 | pDAB115601 | 4 | 40 |
| donor2 + F2 ZFN4_HF | pDAB115622 | 36 | pDAB115609 | 4 | 40 |
| donor2 + F2 ZFN5_HF | pDAB115622 | 36 | pDAB115608 | 4 | 40 |
| donor1 + F2 ZFN6_HF | pDAB115620 | 36 | pDAB115606 | 4 | 40 |
| donor1 + F2 ZFN7_HF | pDAB115620 | 36 | pDAB115604 | 4 | 40 |

Analysis of Targeting

DNA samples from the targeting experiments were analyzed using a locus disruption assay to detect modifications at the FAD2 ZFN cleavage sites or assess targeting by NHEJ. A qPCR assay was designed to measure intact ZFN binding sites in the FAD2 targets. The ZFN mediated donor insertion or cleavage followed by NHEJ repair results in loss of the ZFN binding site and subsequent reduction in detectable qPCR signal. The ZFNs that possesses significant cleavage activity resulted in the production of amplicons with a reduced signal compared to the donor alone treatment. The primers and probes used in the locus disruption assay are provided in Table 4, and their relative positions on the FAD2 loci are shown in FIG. 7.

Results were compared to the signal obtained from intact FAD2 loci in untreated soybean cells. Treatment of protoplasts with the FAD2 2.3 ZFN2_WT ZFN (both experiments) and FAD2 2.6 ZFNs ZFN4_HF (one experiment) and F2 ZFN5 HF (both experiments) in the presence of the appropriate donor vectors resulted in a statistically significant lower signal compared to that obtained from an intact sequence (donor alone).

vector that are generated by ZFN cleavage undergo processing prior to integration within the FAD2 locus, and may result in imperfect end joining products. Confirmation of targeted integration at the target was performed based on an

TABLE 4

Primers and probes for disruption PCR

| Primer Name | Sequence | Probe (fluorophore/quencher) | Target ZFN |
|---|---|---|---|
| GMS116 SOY F | SEQ ID NO: 21 GTAATATGGGCTCAGAGGAATGGT | — | — |
| GMS116 SOY R | SEQ ID NO: 22 ATGGAGAAGAACATTGGAATTGC | — | — |
| GMS116 SOY | SEQ ID NO: 23 CCATGGCCCGGTACCATCTGGTC | HEX | — |
| MAS723 | SEQ ID NO: 80 CACGAGTGTGGTCACCATGCCTT | — | ZFN1 |
| MAS724 | SEQ ID NO: 81 TGAGTGTGACGAGAAGAGAAACAGCC | — | ZFN1 |
| MAS725_FAM | SEQ ID NO: 82 AGCAAGTACCAATGGGTTGATGATGTTGTG | FAM | ZFN1 |
| MAS727 | SEQ ID NO: 83 TGCAAGCCACTACCACCCTTATGC | — | ZFN2/ZFN7 |
| MAS728 | SEQ ID NO: 84 GGCAAAGTGTGTGTGCTGCAAATATG | — | ZFN2/ZFN7 |
| MAS729_FAM | SEQ ID NO: 85 CTAACCGTGAGAGGCTTCTGATCTATGTCTCTGA | FAM | ZFN2/ZFN7 |
| MAS731 | SEQ ID NO: 86 TGAGTGTGATGAGAAGAGAAGCAGCC | — | ZFN3 |
| MAS732_FAM | SEQ ID NO: 87 AGCAAGTACCCATGGGTTGATGATGTTATG | FAM | ZFN3 |
| MAS723 | SEQ ID NO: 80 CACGAGTGTGGTCACCATGCCTT | — | ZFN3 |
| MAS812 | SEQ ID NO: 88 TTGGTTTGGCTGCTATGTGTTTATGG | — | ZFN6 |
| MAS813 | SEQ ID NO: 89 TGTGGCATTGTAGAGAAGAGATGGTGAG | — | ZFN6 |
| MAS814_FAM | SEQ ID NO: 90 AGGGAGCTTTGGCAACTATGGACAGAGATTAT | FAM | ZFN6 |
| MAS824 | SEQ ID NO: 91 AGCCTTCAATGTCTCTGGCAGACCCT | — | ZFN4/ZFN5 |
| MAS818 | SEQ ID NO: 92 GGCATAGTGTGTGTGCTGCAGATATG | — | ZFN4/ZFN5 |
| MAS817_FAM | SEQ ID NO: 93 CAAATCGTGAGAGGCTTTTGATCTATGTCTCTGA | FAM | ZFN4/ZFN5 |

Locus Specific In-Out PCR

To confirm targeted donor insertion, DNA from all treatments was subjected to a locus-specific In-Out PCR assay. The donor vector in the experiments was designed to contain binding sites for all ZFNs that were being tested for targeted integration within the FAD2 locus. Co-delivery of the ZFN and donor into soybean cells results in cleavage of the ZFN binding site at the target and in the donor vector and subsequent integration of the donor into the cleaved FAD2 locus via non-homologous end-joining mechanism. The ends of the FAD2 chromosome site and the linearized donor "In-Out" PCR strategy, where the "Out" primer recognizes sequence at the native genomic locus and the "In" primer binds to sequence within the donor DNA. The In-Out PCR assay was performed on both the 5'- and 3'-ends of the insertion junction.

All of the tested ZFNs showed some evidence of targeting and integration of a donor fragment into the FAD2 soybean locus in at least one experiment as determined by a PCR product in the donor and ZFN samples. Results of donor integrated targeting using the following ZFNs; F2 ZFN2_WT, F2 ZFN2_HF and F2 ZFN4_HF were reproducible as PCR products were produced in at least 2 out of 6 experimental replicates at both the 5' and 3' ends (Table 5).

TABLE 5

Summary of NHEJ targeting at the FAD2 locus in soybean protoplasts. The number of replicates positive for In-Out PCR in independent targeting experiments is shown for the experiments or treatments.

| ZFN ID | F2 ZFN1-3A | F2 ZFN1-3B | F2 ZFN4-7A | F2 ZFN4-7B |
|---|---|---|---|---|
| ZFN 1 WT | 1/6 | 0/6 | — | — |
| ZFN 1 HF | 1/6 | 4/6 | — | — |
| ZFN 2 WT | 3/6 | 5/6 | 5/6 | 5/6 |
| ZFN 2 HF | 4/6 | 3/6 | — | — |
| ZFN 3 WT | 0/6 | 0/6 | — | — |
| ZFN 3 HF | 0/6 | 0/6 | — | — |
| ZFN 4 HF | — | — | 2/6 | 2/6 |
| ZFN 5 HF | — | — | 0/6 | 0/6 |
| ZFN 6 HF | — | — | 0/6 | 0/6 |
| ZFN 7 HF | — | — | 4/6 | 0/6 |

Sequencing of the In-Out PCR Products

Two of the amplicons (of expected size) from each of the In-Out PCR targeting experiments completed with pDAB1115620 and F2 ZFN2_WT or pDAB1115620 and F2 ZFN2_HF were cloned into a plasmid. The resulting plasmid was sequenced using the Sanger sequencing method. Sequences were aligned to a reference sequence in which the single-stranded 4 bp ends that are predicted to result from FokI cleavage were duplicated to represent all possible combinations of the ends. Ten unique sequence patterns were found from the 23 cloned sequences obtained (FIG. 8). All sequence patterns retained a portion of the FAD2 genomic reference sequence located between the ZFN binding sites (GAAATTTC), but the sequence patterns also possessed deletions relative to the FAD2 genomic reference sequence. Sequences 4WT1 and 4WT4 contained deletions that extended into the ZFN binding site on the 3' end of the GAAATTTC sequence. Two sequences, 1HF4 and 6HF4, had single-base insertions. The DNA sequence patterns observed demonstrate that targeting of the donor DNA into the soybean FAD2 locus occurred.

While certain exemplary embodiments have been described herein, those of ordinary skill in the art will recognize and appreciate that many additions, deletions, and modifications to the exemplary embodiments may be made without departing from the scope of the following claims. In addition, features from one embodiment may be combined with features of another embodiment.

What may be claimed is:

1. A soybean cell comprising a genetically modified FAD2 gene, the FAD2 gene comprising a mutation within any of SEQ ID NO: 14 to SEQ ID NO: 20 such that expression of the FAD2 gene is disrupted.

2. The soybean cell according to claim 1, wherein the FAD2 gene is a FAD2 2.3 gene, a FAD2 2.6 gene, or both.

3. The soybean cell according to claim 1, wherein the genetic modification is made using at least one nuclease comprising a cleavage domain or cleavage-half-domain and a DNA-binding binding domain that binds to a target site in any of SEQ ID NO:14 to SEQ ID NO:20.

4. The soybean cell according to claim 3, wherein the DNA-binding domain is selected from the group consisting of a meganuclease DNA-binding domain, a leucine zipper DNA-binding domain, a transcription activator-like (TAL) DNA-binding domain, a single guide RNA of an RNA-guided CRISPR-Cas9, a recombinase, a zinc finger protein DNA-binding domain, and chimeric combinations of any of the foregoing.

5. The soybean cell according to claim 3, wherein the cleavage domain or cleavage half-domain is selected from the group consisting of a cleavage half-domain from a type IIS restriction endonuclease, a cleavage half-domain from FokI endonuclease, a cleavage half-domain from StsI endonuclease, and a homing endonuclease.

6. The soybean cell according to claim 3, wherein the nuclease is a pair of zinc finger nucleases.

7. The soybean cell according to claim 6, wherein the zinc finger nuclease comprises first and second zinc finger nucleases, each zinc finger nuclease comprising a zinc finger protein comprising from three to six zinc finger domains, each zinc finger domain comprising a recognition helix region, wherein the zinc finger protein comprises the recognition helix regions ordered and shown in a single row of Table 2.

8. The soybean cell according to claim 2, wherein the some but not all copies of FAD2 2.3 and FAD2 2.6 are genetically modified.

9. The soybean cell according to claim 1, wherein the mutation comprises integration of an exogenous nucleic acid sequence.

10. The soybean cell according to claim 9, wherein the exogenous nucleic acid sequence interest encodes a protein.

11. The soybean cell according to claim 10, wherein protein provides insecticidal resistance, herbicide tolerance, is involved in nitrogen or water use, or is a selectable marker.

12. The soybean cell according to claim 9, wherein the nucleic acid sequence of interest comprises a DNA-binding domain binding site.

13. A transgenic soybean plant or seed, comprising the genetically modified cell of claim 1.

* * * * *

SEQUENCE LISTING

<160> NUMBER OF SEQ ID NOS: 130

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caagggttcc aaacacaaag cc                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
catcaatact tgttcctgta cc                                              22

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaagaagcct ctctcaaggg ttc                                             23

<210> SEQ ID NO 4
<211> LENGTH: 1100
<212> TYPE: DNA
<213> ORGANISM: Glycine max

<400> SEQUENCE: 4

```
ggaagaagcc tctctcaagg gttccaaaca caaagccacc attcactgtt ggccaactca      60
agaaagcaat tccaccacac tgctttcagc gctccctcct cacttcattc tcctatgttg     120
tttatgacct tcatttgcc ttcatttct acattgccac cacctacttc cacctccttc      180
ctcaacccctt ttccctcatt gcatggccaa tctattgggt tctccaaggt tgccttctca    240
ctggtgtgtg ggtgattgct cacgagtgtg gtcaccatgc cttcagcaag taccaatggg    300
ttgatgatgt tgtgggtttg acccttcact caacactttt agtcccttat ttctcatgga    360
aaataagcca tcgccgccat cactccaaca caggttccct tgaccgtgat gaagtgtttg    420
tcccaaaacc aaaatccaaa gttgcatggt tttccaagta cttaaacaac cctctaggaa    480
gggctgtttc tcttctcgtc acactcacaa tagggtggcc tatgtattta gccttcaatg    540
tctctggtag accctatgat agttttgcaa gccactacca cccttatgct cccatatatt    600
ctaaccgtga gaggcttctg atctatgtct ctgatgttgc tttgtttttct gtgacttact    660
ctctctaccg tgttgcaacc ctgaaagggt tggtttggct gctatgtgtt tatggggtgc    720
ctttgctcat tgtgaacggt tttcttgtga ctatcacata tttgcagcac acacactttg    780
ccttgcctca ttacgattca tcagaatggg actggctgaa gggagctttg gcaactatgg    840
acagagatta tgggattctg aacaaggtgt ttcatcacat aactgatact catgtggctc    900
accatctctt ctctacaatg ccacattacc atgcaatgga ggcaaccaat gcaatcaagc    960
caatattggg tgagtactac caatttgatg acacaccatt ttacaaggca ctgtggagag   1020
aagcgagaga gtgcctctat gtggagccag atgaaggaac atccgagaag ggcgtgtatt   1080
ggtacaggaa caagtattga                                               1100
```

<210> SEQ ID NO 5
<211> LENGTH: 1100
<212> TYPE: DNA
<213> ORGANISM: Glycine max

<400> SEQUENCE: 5

```
ggaagaagcc tctctcaagg gttccaaaca caaagccacc attcactgtt ggccaactca      60
agaaagcaat tccaccacac tgctttcagc gctccctcct cacttcattc tcctatgttg     120
tttatgacct tcatttgcc ttcatttct acattgccac cacctacttc cacctccttc      180
ctcaacccctt ttccctcatt gcatggccaa tctattgggt tctccaaggt tgccttctca    240
ctggtgtgtg ggtgattgct cacgagtgtg gtcaccatgc cttcagcaag taccaatggg    300
ttgatgatgt tgtgggtttg acccttcact caacactttt agtcccttat ttctcatgga    360
aaataagcca tcgccgccat cactccaaca caggttccct tgaccgtgat gaagtgtttg    420
tcccaaaacc aaaatccaaa gttgcatggt tttccaagta cttaaacaac cctctaggaa    480
gggctgtttc tcttctcgtc acactcacaa tagggtggcc tatgtattta gccttcaatg    540
tctctggtag accctatgat agttttgcaa gccactacca cccttatgct cccatatatt    600
ctaaccgtga gaggcttctg atctatgtct ctgatgttgc tttgtttttct gtgacttact    660
ctctctaccg tgttgcaacc ctgaaagggt tggtttggct gctatgtgtt tatggggtgc    720
ctttgctcat tgtgaacggt tttcttgtga ctatcacata tttgcagcac acacactttg    780
ccttgcctca ttacgattca tcagaatggg actggctgaa gggagctttg gcaactatgg    840
acagagatta tgggattctg aacaaggtgt ttcatcacat aactgatact catgtggctc    900
accatctctt ctctacaatg ccacattacc atgcaatgga ggcaaccaat gcaatcaagc    960
```
caatattggg tgagtactac caatttgatg acacaccatt ttacaaggca ctgtggagag   1020
aagcgagaga gtgcctctat gtggagccag atgaaggaac atccgagaag ggcgtgtatt   1080
ggtacaggaa caagtattga                                               1100

<210> SEQ ID NO 6
<211> LENGTH: 1100
<212> TYPE: DNA
<213> ORGANISM: Glycine max

<400> SEQUENCE: 6
ggaagaagcc tctctcaagg gttccaaaca caaagccacc attcactgtt ggccaactca     60
agaaagcaat tccaccacac tgctttcagc gctccctcct cacttcattc tcctatgttg    120
tttatgacct tcatttgcc ttcatttct acattgccac cacctacttc cacctccttc    180 ctcaacccctt ttccctcatt gcatggccaa tctattgggt tctccaaggt tgccttctca    240
ctggtgtgtg ggtgattgct cacgagtgtg gtcaccatgc cttcagcaag taccaatggg    300
ttgatgatgt tgtgggtttg acccttcact caacactttt agtcccttat ttctcatgga    360
aaataagcca tcgccgccat cactccaaca caggttccct tgaccgtgat gaagtgtttg    420
tcccaaaacc aaaatccaaa gttgcatggt tttccaagta cttaaacaac cctctaggaa    480
gggctgtttc tcttctcgtc acactcacaa tagggtggcc tatgtattta gccttcaatg    540
tctctggtag accctatgat agttttgcaa gccactacca cccttatgct cccatatatt    600
ctaaccgtga gaggcttctg atctatgtct ctgatgttgc tttgtttct gtgacttact    660 ctctctaccg tgttgcaacc ctgaaagggt tggtttggct gctatgtgtt tatggggtgc    720
ttttgctcat tgtgaacggt tttcttgtga ctatcacata tttgcagcac acacactttg    780
ccttgcctca ttacgattca tcagaatggg actggctgaa gggagctttg gcaactatgg    840
acagagatta tgggattctg aacaaggtgt tcatcacat aactgatact catgtggctc    900
accatctctt ctctacaatg ccacattacc atgcaatgga ggcaaccaat gcaatcaagc    960
caatattggg tgagtactac caatttgatg acacaccatt ttacaaggca ctgtggagag   1020
aagcgagaga gtgcctctat gtggagccag atgaaggaac atccgagaag ggcgtgtatt   1080
ggtacaggaa caagtattga                                               1100

<210> SEQ ID NO 7
<211> LENGTH: 1100
<212> TYPE: DNA
<213> ORGANISM: Glycine max

<400> SEQUENCE: 7
ggaagaagcc tctctcaagg gttccaaaca caaagccacc attcactgtt ggccaactca     60
agaaagcaat tccaccacac tgctttcagc gctccctcct cacttcattc tcctatgttg    120
tttatgacct tcatttgcc ttcatttct acattgccac cacctacttc cacctccttc    180 ctcaacccctt ttccctcatt gcatggccaa tctattgggt tctccaaggt tgccttctca    240
ctggtgtgtg ggtgattgct cacgagtgtg gtcaccatgc cttcagcaag taccaatggg    300
ttgatgatgt tgtgggtttg acccttcact caacactttt agtcccttat ttctcatgga    360
aaataagcca tcgccgccat cactccaaca caggttccct tgaccgtgat gaagtgtttg    420
tcccaaaacc aaaatccaaa gttgcatggt tttccaagta cttaaacaac cctctaggaa    480
gggctgtttc tcttctcgtc acactcacaa tagggtggcc tatgtattta gccttcaatg    540

```
tctctggtag acccuatgat agtttutgcaa gccactacca cccttatgct cccatatatt      600
```
(corrected)
```
tctctggtag acccuatgat agttutgcaa gccactacca cccttatgct cccatatatt       600
ctaaccgtga gaggcttctg atctatgtct ctgatgttgc tttgttttct gtgacttact       660
ctctctaccg tgttgcaacc ctgaaagggt tggtttggct gctatgtgtt tatggggtgc       720
ctttgctcat tgtgaacggt tttcttgtga ctatcacata tttgcagcac acacactttg       780
ccttgcctca ttacgattca tcagaatggg actggctgaa gggagctttg gcaactatgg       840
acagagatta tgggattctg aacaaggtgt tcatcacat aactgatact catgtggctc        900
accatctctt ctctacaatg ccacattacc atgcaatgga ggcaaccaat gcaatcaagc       960
caatattggg tgagtactac caatttgatg acacaccatt ttacaaggca ctgtggagag      1020
aagcgagaga gtgcctctat gtggagccag atgaaggaac atccgagaag ggcgtgtatt      1080
ggtacaggaa caagtattga                                                  1100

<210> SEQ ID NO 8
<211> LENGTH: 1100
<212> TYPE: DNA
<213> ORGANISM: Glycine max

<400> SEQUENCE: 8
ggaagaagcc tctctcaagg gttccaaaca caaagccacc attcactgtt ggccaactca       60
agaaagcaat tccaccacac tgctttcagc gctccctcct cacttcattc tcctatgttg      120
tttatgacct ttcatttgcc ttcattttct acattgccac cacctacttc cacctccttc      180
ctcaacccut ttccctcatt gcatggccaa tctattgggt tctccaaggt tgccttctca      240
ctggtgtgtg ggtgattgct cacgagtgtg gtcaccatgc cttcagcaag taccaatggg      300
ttgatgatgt tgtgggtttg acccttcact caacactttt agtcccttat ttctcatgga      360
aaataagcca tcgccgccat cactccaaca caggttccct tgaccgtgat gaagtgtttg      420
tcccaaaacc aaaatccaaa gttgcatggt tttccaagta cttaaacaac cctctaggaa      480
gggctgtttc tcttctcgtc acactcacaa tagggtggcc tatgtattta gccttcaatg      540
tctctggtag accctatgat agttutgcaa gccactacca cccttatgct cccatatatt      600
ctaaccgtga gaggcttctg atctatgtct ctgatgttgc tttgttttct gtgacttact       660
ctctctaccg tgttgcaacc ctgaaagggt tggtttggct gctatgtgtt tatggggtgc      720
ctttgctcat tgtgaacggt tttcttgtga ctatcacata tttgcagcac acacactttg      780
ccttgcctca ttacgattca tcagaatggg actggctgaa gggagctttg gcaactatgg      840
acagagatta tgggattctg aacaaggtgt tcatcacat aactgatact catgtggctc       900
accatctctt ctctacaatg ccacattacc atgcaatgga ggcaaccaat gcaatcaagc      960
caatattggg tgagtactac caatttgatg acacaccatt ttacaaggca ctgtggagag     1020
aagcgagaga gtgcctctat gtggagccag atgaaggaac atccgagaag ggcgtgtatt     1080
ggtacaggaa caagtattga                                                 1100

<210> SEQ ID NO 9
<211> LENGTH: 1101
<212> TYPE: DNA
<213> ORGANISM: Glycine max

<400> SEQUENCE: 9
cagaagaagc ctctctcaag ggttccaaac acaaagccac cattcactgt tggccaactc       60
aagaaagcca ttccaccgca ctgctttcag cgttccctcc tcacttcatt gtcctatgtt      120
gtttatgacc tttcattggc tttcattttc tacattgcca ccacctactt ccacctcctc      180
```

-continued

```
cctcacccct tttccctcat tgcatggcca atctattggg ttctccaagg ttgcattctt      240
actggcgtgt gggtgattgc tcacgagtgt ggtcaccatg ccttcagcaa gtacccatgg      300
gttgatgatg ttatgggttt gaccgttcac tcagcacttt tagtccctta tttctcatgg      360
aaaataagcc atcgccgcca ccactccaac acgggttccc ttgaccgtga tgaagtgttt      420
gtcccaaaac caaaatccaa agttgcatgg tacaccaagt acctgaacaa ccctctagga      480
agggctgctt ctcttctcat cacactcaca ataggggtggc ctttgtattt agccttcaat      540
gtctctggca gaccctatga tggttttgct agccactacc acccttatgc tcccatatat      600
tcaaatcgtg agaggctttt gatctatgtc tctgatgttg ctttgttttc tgtgacttac      660
ttgctctacc gtgttgcaac tatgaaaggg ttggtttggc tgctatgtgt ttatggggtg      720
ccattgctca ttgtgaacgg ttttcttgtg accatcacat atctgcagca cacacactat      780
gccttgcctc actatgattc atcagaatgg gattggctga ggggtgctttt ggcaactatg      840 gacagagatt atggaattct gaacaaggtg tttcaccaca taactgatac tcatgtggct      900
caccatcttt tctctacaat gccacattac catgcaacgg aggcaaccaa tgcaatgaag      960
ccaatattgg gtgagtacta ccgatttgat gacacaccat tttacaaggc actgtggaga     1020
gaagcaagag agtgcctcta tgtggagcca gatgaaggaa catccgagaa gggcgtgtat     1080
tggtacagga acaagtattg a                                               1101
```

<210> SEQ ID NO 10
<211> LENGTH: 1101
<212> TYPE: DNA
<213> ORGANISM: Glycine max

<400> SEQUENCE: 10

```
cagaagaagc ctctctcaag ggttccaaac acaaagccac cattcactgt tggccaactc       60
aagaaagcca ttccaccgca ctgctttcag cgttccctcc tcacttcatt gtcctatgtt      120
gtttatgacc tttcattggc tttcattttc tacattgcca ccacctactt ccacctcctc      180
cctcacccct tttccctcat tgcatggcca atctattggg ttctccaagg ttgcattctt      240
actggcgtgt gggtgattgc tcacgagtgt ggtcaccatg ccttcagcaa gtacccatgg      300
gttgatgatg ttatgggttt gaccgttcac tcagcacttt tagtccctta tttctcatgg      360
aaaataagcc atcgccgcca ccactccaac acgggttccc ttgaccgtga tgaagtgttt      420
gtcccaaaac caaaatccaa agttgcatgg tacaccaagt acctgaacaa ccctctagga      480
agggctgctt ctcttctcat cacactcaca ataggggtggc ctttgtattt agccttcaat      540
gtctctggca gaccctatga tggttttgct agccactacc acccttatgc tcccatatat      600
tcaaatcgtg agaggctttt gatctatgtc tctgatgttg ctttgttttc tgtgacttac      660
ttgctctacc gtgttgcaac tatgaaaggg ttggtttggc tgctatgtgt ttatggggtg      720
ccattgctca ttgtgaacgg ttttcttgtg accatcacat atctgcagca cacacactat      780
gccttgcctc actatgattc atcagaatgg gattggctga ggggtgctttt ggcaactatg      840 gacagagatt atggaattct gaacaaggtg tttcaccaca taactgatac tcatgtggct      900
caccatcttt tctctacaat gccacattac catgcaacgg aggcaaccaa tgcaatgaag      960
ccaatattgg gtgagtacta ccgatttgat gacacaccat tttacaaggc actgtggaga     1020
gaagcaagag agtgcctcta tgtggagcca gatgaaggaa catccgagaa gggcgtgtat     1080
tggtacagga acaagtattg a                                               1101
```

<210> SEQ ID NO 11
<211> LENGTH: 1101
<212> TYPE: DNA
<213> ORGANISM: Glycine max

<400> SEQUENCE: 11

| | | | | | |
|---|---|---|---|---|---|
| cagaagaagc | ctctctcaag | ggttccaaac | acaaagccac | cattcactgt | tggccaactc | 60 |
| aagaaagcca | ttccaccgca | ctgctttcag | cgttccctcc | tcacttcatt | gtcctatgtt | 120 |
| gtttatgacc | tttcattggc | tttcattttc | tacattgcca | ccacctactt | ccacctcctc | 180 |
| cctcacccct | ttttcctcat | tgcatggcca | atctattggg | ttctccaagg | ttgcattctt | 240 |
| actggcgtgt | gggtgattgc | tcacgagtgt | ggtcaccatg | ccttcagcaa | gtacccatgg | 300 |
| gttgatgatg | ttgtgggttt | gaccgttcac | tcagcacttt | tagtccctta | tttctcatgg | 360 |
| aaaataagcc | atcgccgcca | ccactccaac | acgggttccc | ttgaccgtga | tgaagtgttt | 420 |
| gtcccaaaac | caaaatccaa | agttgcatgg | tacaccaagt | acctgaacaa | ccctctagga | 480 |
| agggctgctt | ctcttctcat | cacactcaca | atagggtggc | ctttgtattt | agccttcaat | 540 |
| gtctctggca | gaccctatga | tggttttgct | agccactacc | accctatgc | tcctatatat | 600 |
| tcaaaccgtg | agaggcttct | gatctatgtc | tctgatgttg | ctttgttttc | tgtgacttac | 660 |
| ttgctctacc | gtgttgcaac | tatgaaaggg | ttggtttggc | tgctatgtgt | ttatggggtg | 720 |
| ccattgctca | ttgtgaacgg | ttttcttgtg | accatcacat | atctgcagca | cacacactat | 780 |
| gccttgcctc | actatgattc | atcagaatgg | gattggctga | ggggtgcttt | ggcaactatg | 840 |
| gacagagatt | atgggattct | gaacaaggtg | tttcaccaca | taactgatac | tcatgtggct | 900 |
| caccatcttt | tctctacaat | gccacattac | catgcaacgg | aggcaaccaa | tgcaatgaag | 960 |
| ccaatattgg | gtgagtacta | ccgatttgat | gacacaccat | tttacaaggc | actgtggaga | 1020 |
| gaagcaagag | agtgcctcta | tgtggagcca | gatgaaggaa | catccgagaa | gggcgtgtat | 1080 |
| tggtacagga | acaagtattg | a | | | | 1101 |

<210> SEQ ID NO 12
<211> LENGTH: 1101
<212> TYPE: DNA
<213> ORGANISM: Glycine max

<400> SEQUENCE: 12

| | | | | | |
|---|---|---|---|---|---|
| cagaagaagc | ctctctcaag | ggttccaaac | acaaagccac | cattcactgt | tggccaactc | 60 |
| aagaaagcca | ttccaccgca | ctgctttcag | cgttccctcc | tcacttcatt | gtcctatgtt | 120 |
| gtttatgacc | tttcattggc | tttcattttc | tacattgcca | ccacctactt | ccacctcctc | 180 |
| cctcacccct | ttttccctcat | tgcatggcca | atctattggg | ttctccaagg | ttgcattctt | 240 |
| actggcgtgt | gggtgattgc | tcacgagtgt | ggtcaccatg | ccttcagcaa | gtacccatgg | 300 |
| gttgatgatg | ttatgggttt | gaccgttcac | tcagcacttt | tagtccctta | tttctcatgg | 360 |
| aaaataagcc | atcgccgcca | ccactccaac | acgggttccc | ttgaccgtga | tgaagtgttt | 420 |
| gtcccaaaac | caaaatccaa | agttgcatgg | tacaccaagt | acctgaacaa | ccctctagga | 480 |
| agggctgctt | ctcttctcat | cacactcaca | atagggtggc | ctttgtattt | agccttcaat | 540 |
| gtctctggca | gaccctatga | tggttttgct | agccactacc | accctatgc | tcccatatat | 600 |
| tcaaatcgtg | agaggctttt | gatctatgtc | tctgatgttg | ctttgttttc | tgtgacttac | 660 |
| ttgctctacc | gtgttgcaac | tatgaaaggg | ttggtttggc | tgctatgtgt | ttatggggtg | 720 |
| ccattgctca | ttgtgaacgg | ttttcttgtg | accatcacat | atctgcagca | cacacactat | 780 |

```
gccttgcctc actatgattc atcagaatgg gattggctga ggggtgcttt ggcaactatg    840
gacagagatt atggaattct gaacaaggtg tttcaccaca taactgatac tcatgtggct    900
caccatcttt tctctacaat gccacattac catgcaacgg aggcaaccaa tgcaatgaag    960
ccaatattgg gtgagtacta ccgatttgat gacacaccat tttacaaggc actgtggaga   1020
gaagcaagag agtgcctcta tgtggagcca gatgaaggaa catccgagaa gggcgtgtat   1080
tggtacagga acaagtattg a                                             1101

<210> SEQ ID NO 13
<211> LENGTH: 1101
<212> TYPE: DNA
<213> ORGANISM: Glycine max

<400> SEQUENCE: 13
cagaagaagc ctctctcaag ggttccaaac acaaagccac cattcactgt tggccaactc     60
aagaaagcca ttccaccgca ctgctttcag cgttccctcc tcacttcatt gtcctatgtt    120
gtttatgacc tttcattggc tttcattttc tacattgcca ccacctactt ccacctcctc    180 cctcaccccct tttccctcat tgcatggcca atctattggg ttctccaagg ttgcattctt    240
actggcgtgt gggtgattgc tcacgagtgt ggtcaccatg ccttcagcaa gtacccatgg    300
gttgatgatg ttgtgggttt gaccgttcac tcagcacttt tagtccctta tttctcatgg    360
aaaataagcc atcgccgcca ccactccaac acgggttccc ttgaccgtga tgaagtgttt    420
gtcccaaaac caaaatccaa agttgcatgg tacaccaagt acctgaacaa ccctctagga    480
agggctgctt ctcttctcat cacactcaca ataggggtggc ctttgtattt agccttcaat    540
gtctctggca gacccctatga tggttttgct agccactacc cccttatgc tcccatatat    600 tcaaatcgtg agaggctttt gatctatgtc tctgatgttg ctttgttttc tgtgacttac    660
ttgctctacc gtgttgcaac tatgaaaggg ttggtttggc tgctatgtgt ttatggggtg    720
ccattgctca ttgtgaacgg ttttcttgtg accatcacat atctgcagca cacacactat    780
gccttgcctc actatgattc atcagaatgg gattggctga ggggtgcttt ggcaactatg    840
gacagagatt atgggattct gaacaaggtg tttcaccaca taactgatac tcatgtggct    900
caccatcttt tctctacaat gccacattac catgcaacgg aggcaaccaa tgcaatgaag    960
ccaatattgg gtgagtacta ccgatttgat gacacaccat tttacaaggc actgtggaga   1020
gaagcaagag agtgcctcta tgtggagcca gatgaaggaa catccgagaa gggcgtgtat   1080
tggtacagga acaagtattg a                                             1101

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agccatcgcc gccatcactc caacacaggt tcccttgac                             39

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 15
tctaccgtgt tgcaaccctg aaagggttgg tttggctgct atg        43

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gccttgcctc attacgattc atcagaatgg gactggctga a          41

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctgtgactta ctctctctac cgtgttgcaa ccctgaaagg g          41

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agccatcgcc gccaccactc caacacgggt tcccttgac             39

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ctgtgactta cttgctctac cgtgttgcaa ctatgaaagg g          41

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttcaatgtct ctggcagacc ctatgatggt tttgct                36

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtaatatggg ctcagaggaa tggt                                      24

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atggagaaga acattggaat tgc                                       23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
ccatggcccg gtaccatctg gtc                                       23

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Ser Ser Asp Leu Ser Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Lys Asp Ala Leu Val Ala
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ser Ala Asp Leu Thr Arg
1               5

<210> SEQ ID NO 27
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 27

Arg Ser Asp Asp Leu Thr Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ser Asp Ala Met Ser Gln
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Asn Ala Ser Arg Thr Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Arg Ser Asn Leu Ser Arg
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

His Lys Trp Leu Arg Asn Gln
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Ser Ser Asp Arg Lys Lys
1               5
```

```
<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Arg His His Leu Thr Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Ser Gly Thr Arg Lys Thr
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Asn Ala His Arg Lys Thr
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Ser Gly Asp Leu Thr Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Thr Ser Thr Leu Ser Lys
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38
```

```
Thr Ser Gly Ser Leu Ser Arg
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ser Asp His Leu Thr Gln
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Ser Asp Val Leu Ser Glu
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ser Ala Asp Leu Ser Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Thr Asp Ala Leu Arg Gly
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

His Arg Ser Ala Arg Lys Arg
1               5

<210> SEQ ID NO 44
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 44

Asp Arg Ser His Leu Thr Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Ser Gly Asn Leu His Val
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ser Asp His Leu Ser Ala
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ser Asn Leu Leu Val Ala
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ser Gly Ala Leu Ala Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Arg Ser Ala Leu Ala Arg
1               5
```

```
<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Ser Ser Asn Leu Ala Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Ser Ser Asp Leu Arg Arg
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ser Asp Thr Leu Ser Glu
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Ser Gly His Leu Ser Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ser Asp Val Leu Ser Thr
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 55

Gln Asn Ala His Arg Ile Lys
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Ser Asp Asn Leu Ser Gln
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Ser Asn Asp Arg Lys Lys
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Ser Asp Asn Leu Ser Thr
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Met Arg Gln His Leu Leu Asn
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Ser Asp Asn Leu Ala Arg
1               5

<210> SEQ ID NO 61
<211> LENGTH: 7
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 61

Gln Lys Lys Asp Arg Ser Tyr
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Ser Asp His Leu Ser Arg
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Arg Ser Asn Arg Lys Thr
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Ser Asp Thr Leu Ser Ala
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asp Lys Ser Thr Arg Thr Lys
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Thr Ser Gly Ser Leu Thr Arg
1               5
```

```
<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Ser Asp Ser Leu Ser Ala
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Ser Asp Ala Leu Ala Arg
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Arg Asp Ile Leu His Gln
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Arg Thr His Leu Lys Ala
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Arg Ser Thr Arg Thr Asn
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 72

Gln Ser Gly Asn Leu Ala Arg
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Trp Arg Ile Ser Leu Ala Ala
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Trp Lys Glu Ser Leu Gly Ala
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

His Arg Lys Ser Leu Ser Arg
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Tyr His Trp Tyr Leu Lys Lys
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Thr Ser Gly His Leu Ser Arg
1               5

<210> SEQ ID NO 78
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Thr Ser Gly Asn Leu Thr Arg
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Trp Trp Thr Ser Arg Ala Leu
1               5

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cacgagtgtg gtcaccatgc ctt                                          23

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tgagtgtgac gagaagagaa acagcc                                       26

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82
agcaagtacc aatgggttga tgatgttgtg                                   30

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tgcaagccac taccaccctt atgc                                         24

<210> SEQ ID NO 84
```

-continued

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ggcaaagtgt gtgtgctgca aatatg                                          26

<210> SEQ ID NO 85
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
ctaaccgtga gaggcttctg atctatgtct ctga                                 34

<210> SEQ ID NO 86
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tgagtgtgat gagaagagaa gcagcc                                          26

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
agcaagtacc catgggttga tgatgttatg                                      30

<210> SEQ ID NO 88
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ttggtttggc tgctatgtgt ttatgg                                          26

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
tgtggcattg tagagaagag atggtgag                                        28

<210> SEQ ID NO 90
<211> LENGTH: 32
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
agggagcttt ggcaactatg gacagagatt at                                32

<210> SEQ ID NO 91
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
agccttcaat gtctctggca gaccct                                       26

<210> SEQ ID NO 92
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ggcatagtgt gtgtgctgca gatatg                                       26

<210> SEQ ID NO 93
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 93
caaatcgtga gaggcttttg atctatgtct ctga                              34

<210> SEQ ID NO 94
<400> SEQUENCE: 94

000

<210> SEQ ID NO 95
<400> SEQUENCE: 95

000

<210> SEQ ID NO 96
<400> SEQUENCE: 96

000

<210> SEQ ID NO 97
<400> SEQUENCE: 97

000

<210> SEQ ID NO 98
```

```
<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109
```

000

<210> SEQ ID NO 110
<400> SEQUENCE: 110

000

<210> SEQ ID NO 111
<400> SEQUENCE: 111

000

<210> SEQ ID NO 112
<400> SEQUENCE: 112

000

<210> SEQ ID NO 113
<400> SEQUENCE: 113

000

<210> SEQ ID NO 114
<400> SEQUENCE: 114

000

<210> SEQ ID NO 115
<400> SEQUENCE: 115

000

<210> SEQ ID NO 116
<400> SEQUENCE: 116

000

<210> SEQ ID NO 117
<400> SEQUENCE: 117

000

<210> SEQ ID NO 118
<400> SEQUENCE: 118

000

<210> SEQ ID NO 119
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ttactctctc taccgtgttg caaccctgaa atttcagggt tgcaacacgg tagagagagt    60
aa                                                              62

<210> SEQ ID NO 120
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ttactctctc taccgtgttg caaccctgat cagggttgca acacggtaga gagagtaa    58

<210> SEQ ID NO 121
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ttactctctc taccgtgttg caaccctgaa agggttgcaa cacggtagag agagtaa     57

<210> SEQ ID NO 122
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ttactctctc taccgtgttg caaccctgag gttgcaacac ggtagagaga gtaa        54

<210> SEQ ID NO 123
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ttactctctc taccgtgttg caaccctgaa                                   30

<210> SEQ ID NO 124
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ttactctctc taccgtgttg caaccctgat ttcagggttg caacacggta gagagagtaa  60

<210> SEQ ID NO 125
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ttactctctc taccgtgttg caaccctgat tcagggttgc aacacggtag agagagtaa   59

<210> SEQ ID NO 126
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ttactctctc taccgtgttg caaccctatt cagggttgca acacggtaga gagagtaa          58

<210> SEQ ID NO 127
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ttactctctc taccgtgttg caaccctgat tcagggttgc aacacggtag agagagtaa         59

<210> SEQ ID NO 128
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ttactctctc taccgtgttg caaccctgaa tcagggttgc aacacggtag agagagtaa         59

<210> SEQ ID NO 129
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ttactctctc taccgtgttg caaccctgaa agggttgcaa cacggtagag agagtaa          57

<210> SEQ ID NO 130
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ttactctctc taccgtgttg caaccctctt tcagggttgc aacacggtag agagagtaa         59